US006752772B2

(12) United States Patent
Kahn

(10) Patent No.: US 6,752,772 B2
(45) Date of Patent: Jun. 22, 2004

(54) MANIPULATION DEVICE WITH DYNAMIC INTENSITY CONTROL

(76) Inventor: Rocky Kahn, 174 Santa Clara Ave., Oakland, CA (US) 94610

( * ) Notice: Subject to any disclaimer, the term of this patent is extended or adjusted under 35 U.S.C. 154(b) by 230 days.

(21) Appl. No.: 10/142,354

(22) Filed: May 9, 2002

(65) Prior Publication Data

US 2003/0212352 A1 Nov. 13, 2003

Related U.S. Application Data

(60) Provisional application No. 60/369,776, filed on Apr. 3, 2002.

(51) Int. Cl.[7] .............................................. A61H 15/00
(52) U.S. Cl. ......................... 601/98; 601/103; 601/108; 601/116
(58) Field of Search .............................. 601/55, 61, 86, 601/90, 98, 99, 100, 101, 102, 103, 108, 112, 113, 116, 117; 4/541.4; 5/670, 689

(56) References Cited

U.S. PATENT DOCUMENTS

| | | | | |
|---|---|---|---|---|
| 3,859,990 A | * | 1/1975 | Simon | 601/157 |
| 4,953,240 A | * | 9/1990 | Gardenier | 601/157 |
| 4,976,256 A | * | 12/1990 | Marlin et al. | 601/55 |
| 5,406,654 A | * | 4/1995 | Antoine | 4/541.4 |
| 6,027,464 A | * | 2/2000 | Dahlquist | 601/148 |
| 6,139,512 A | * | 10/2000 | Ricchio | 601/55 |
| 6,669,649 B2 | * | 12/2003 | Kahn | 600/529 |

* cited by examiner

Primary Examiner—Nicholas D. Lucchesi
Assistant Examiner—Quang D. Thanh
(74) Attorney, Agent, or Firm—Porter, Wright, Morris & Arthur, LLP.

(57) ABSTRACT

A device includes at least one manipulator located below the user to manipulate the user, a translator which moves the manipulator along the user, and a mechanism to change a pressure intensity of the manipulator while providing spatially uniform support to the user outside a contact patch of the manipulator. Various embodiments include adjusting tension of a membrane supporting the user above the manipulator, adjusting the vertical position of a membrane supporting the user above the manipulator, adjusting fluid pressure in a bladder located between the user and the manipulator, adjusting fluid pressure in a bladder containing the manipulator; adjusting emergence of the user in a liquid supporting the user, changing the level of liquid supporting the user relative by pumping the liquid or actuating valves which allow the liquid to flow, and injecting gas into liquid supporting the user to modifying its density.

75 Claims, 30 Drawing Sheets

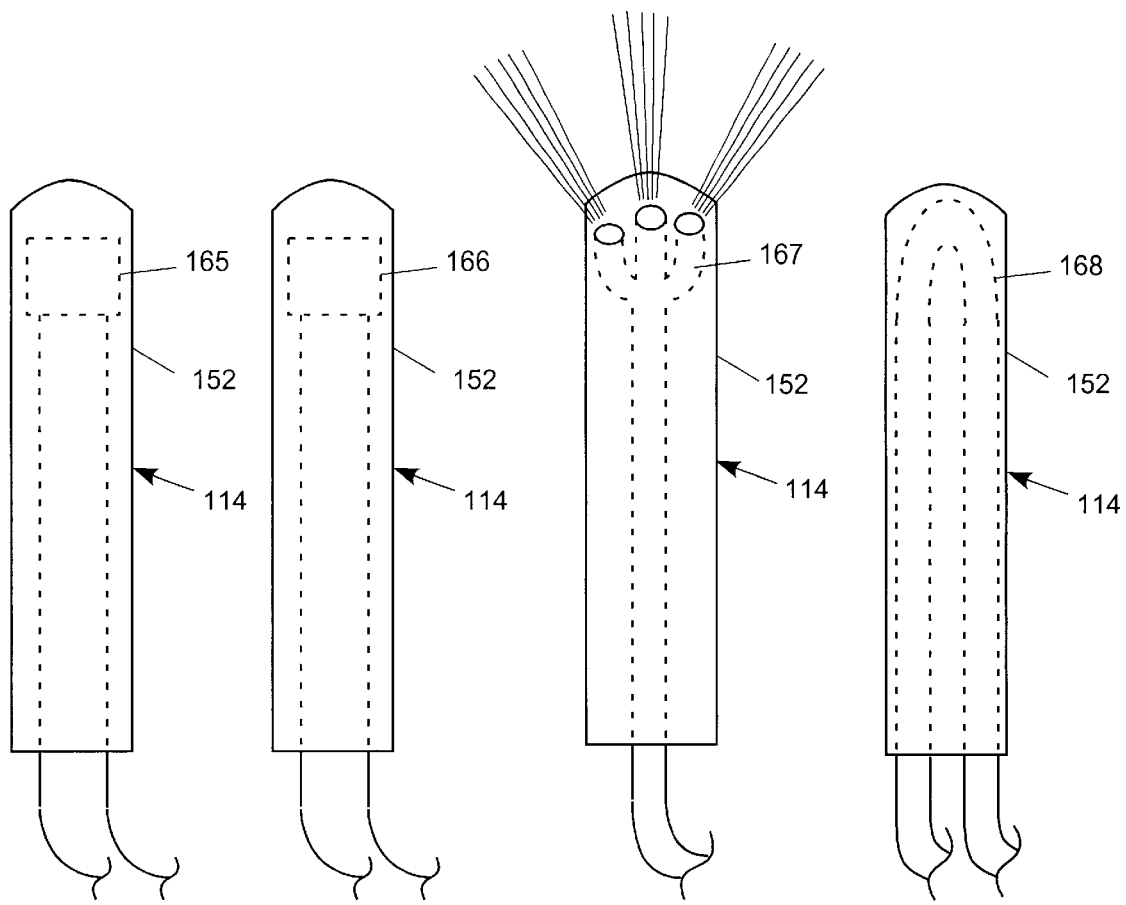

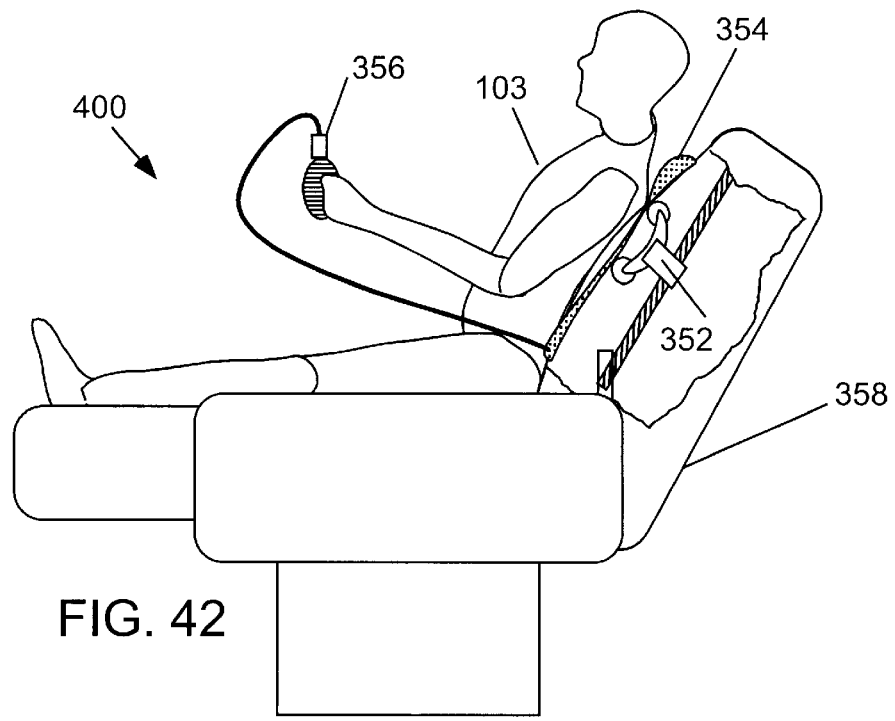
FIG. 42
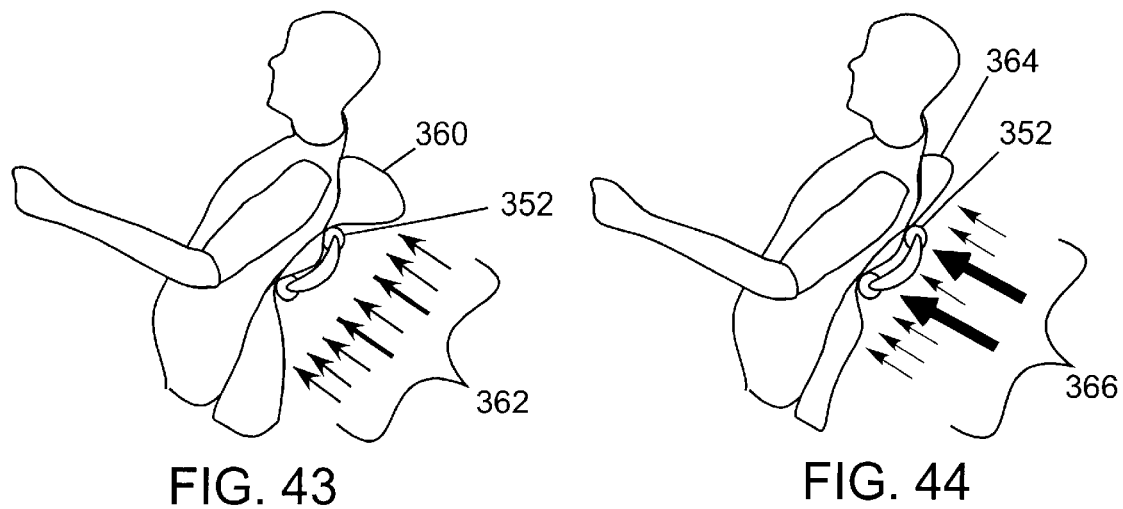
FIG. 43                    FIG. 44

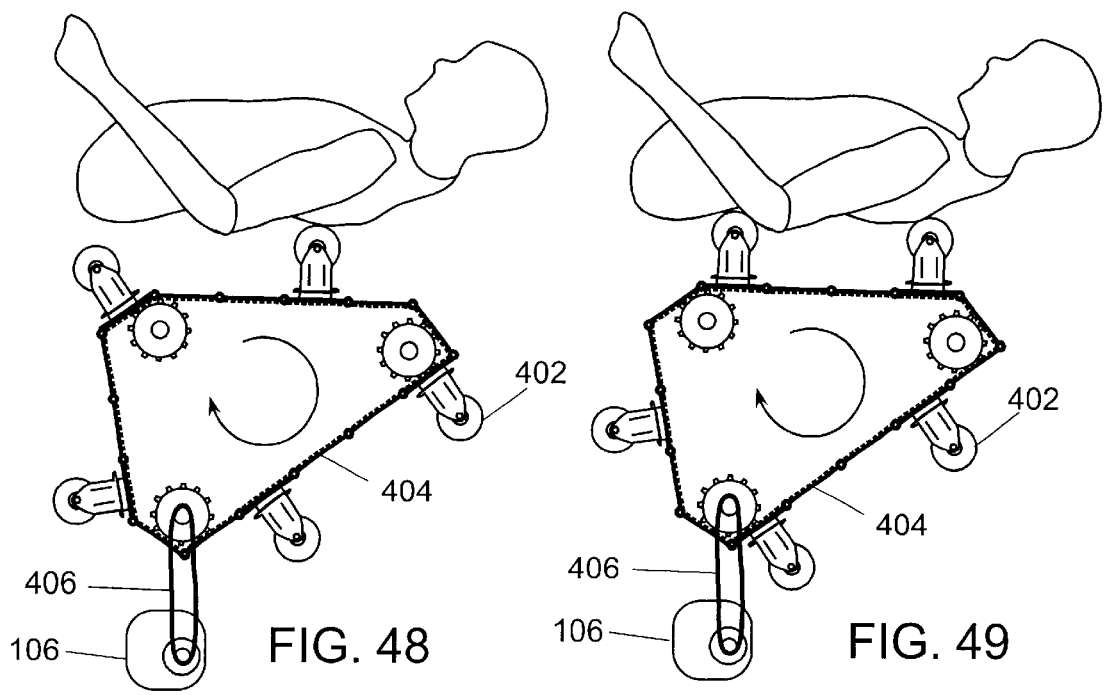
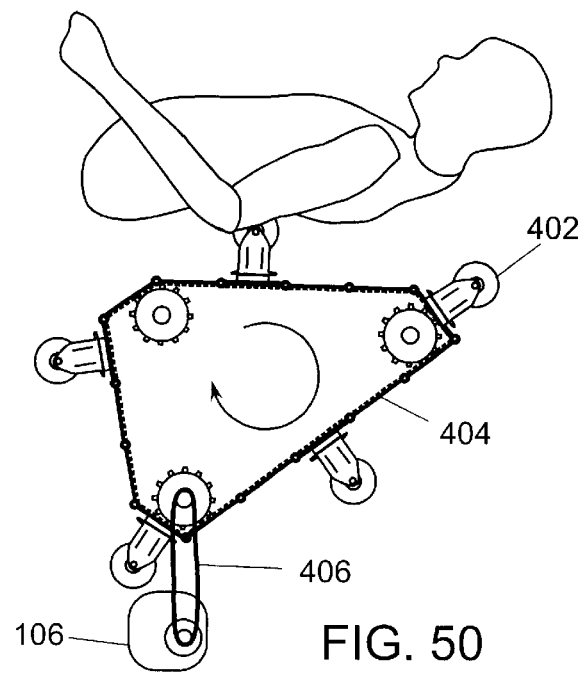

Standard lung volumes and capacities

MANIPULATION DEVICE WITH DYNAMIC INTENSITY CONTROL

CROSS-REFERENCE TO RELATED APPLICATIONS

This Application claims priority from U.S. Provisional Application No. 60/369,776 of the same title and filed Apr. 3, 2002.

STATEMENT REGARDING FEDERALLY SPONSORED RESEARCH

Not Applicable

REFERENCE TO MICROFICHE APPENDIX

Not Applicable

FIELD OF THE INVENTION

The present invention generally relates to manipulation devices and, more particularly, to (a) massage units and massage machines of the chair or bed types which comprise therapeutic fingers for massaging the affected part of the user to be treated, (b) water massaging machines such as hot tubs with massaging attachments; (c) automatic stretching machines; and (d) automatic bathing machines.

BACKGROUND OF THE INVENTION

Each of us seeks comfort, well-being, and insight through stimulating or soothing our senses. When we visit a gallery, listen to a symphony, recognize a fragrance, or enjoy a gourmet meal, we stimulate our senses. The sensory experience best suited to soothe discomfort is perhaps tactility: the most powerful sense in its ability to relax and heal. Touch relieves stress, improves mood, and releases constriction in movement. It also provokes emotional release and strengthens interpersonal connections.

Massage Chairs

Massage is perhaps the most well-recognized body therapy to address the aches, pains, and exhaustion of day-to-day life. State-of-the art massage chairs attempt to mimic the pressure applied by the hands of a skilled massage therapist. The location, frequency, and intensity of pressure is varied in part by automated massage strokes, namely, kneading, vibratory, and tapping strokes.

The most sophisticated massage chairs on the market today allow for dynamic control of only the location and frequency of pressure applied. The user can, for instance, determine the placement of a stroke by selecting a key on the control panel or the controller can choose a kneading stroke that automatically shifts pressure from place to place. Controllers can also change the tempo of such a stroke.

While tapping strokes percussively apply time-varying force, there are currently no massage chairs in which the controller can vary manipulation pressure in an automated fashion. The only way a user can alter the manipulation intensity in a massage chair today is to manually apply or remove padding to the machine. There have been proposals to automate pressure control but none has yet been produced because each design would compromise ease-of-use, disturb the industrial design and/or increase manufacturing costs.

Physical Therapy Devices

Physical therapy devices help to heal injuries by moving joints through ranges of movement and thereby lengthening and stretching muscles. In contrast, massage chairs manipulate muscles with a greater variety of modalities but do not manipulate joints. The benefits of integrating automated muscle manipulation with range-of-motion exercises have not been pursued, in part because the body supports required for range-of-motion therapy interfere with muscle manipulation. The large, broadly supportive pads used to position users' limbs in physical therapy devices make it impossible to provide the localized muscle manipulation provided by a massage chair. However, were one to construct a massage chair with rollers that attempted to reposture users through ranges of motion, the rollers would apply excessive and painful levels of pressure through part of the movement. To make these therapies compatible, one must devise a method of controlling the force exerted by the rollers as they reposture the user.

Hydrotherapy

Hot water soaking has been shown to relieve the symptoms of arthritis, among other ailments. Hydrotherapy products claim to provide heat, buoyancy, and massage as therapy. Immersion in hot water raises the body temperature and causes blood vessels to dilate increasing the body's circulation. The buoyancy of the water reduces body weight by 85 to 90 percent and relieves pressure on joints and muscles. The jet stream of the hot tub, however, does not provide the benefits of conventional massage. The pressure of a hot tub jet varies to such an extent, temporally and spatially, that the sensation is closer to abrasion than massage, over stimulating the surface of the skin while ignoring deeper musculature. Massage chairs offer much better massage than hot tub jets.

Massage Theory and Practice

It has been known for a long time that massage techniques have beneficial effects on the human body for improving blood circulation, for eliminating fat or cellulite, for relieving pain or stiffness, for reabsorbing edemas, and for improving muscular performance. These techniques were originally manual, but machines have been developed to satisfy the increasing demand for this practice and for ensuring that treatment can be made available regularly, inexpensively, and over a long period of time as a replacement for the hand of the masseur, whose training is lengthy and specialized, who is usually available only by prior arrangement and/or in a suboptimal location, and who can be available for only one person at a time.

Various massage machines or devices are known for pressing or stimulating the shoulders, waist or other parts of the human body to remove stiffness. Such devices can be divided into the chair type, bed type and handy (handheld) type. With respect to the mode of action on the affected part, these devices resort to mechanical pressure (steady, sliding, rolling, or vibratory) or water jets. Massage can be applied while the user is dry or immersed in water Limited Dorsal-Ventral Motion in Dry-Type Manipulators Dry mechanical pressure massage and bathing devices typically operate by applying force using a roller or post-type manipulator which rolls or slides tangent to the skin (lateral-medial and rostral-caudal axes) and periodically pushes into the skin (dorsal-ventral axis). This dorsal-ventral movement has limited dynamic range because it is typically generated by a rotational actuator using an off-center cam as in the Family Corp. FMC-300 massage chair.

Force Dynamism

Very few automatic manipulation devices provide the capability for a controller to dynamically vary the intensity of manipulation during the session. For example, the Family Corp. FMC-300 massage chair is not capable of delivering a light massage which slowly increases in intensity. The prior art which has this capability, typically implements it in one of a number of means which this invention improves upon. These typical means include: (a) A piston or scissor-jack pushing a manipulator into the user wherein the piston or jack extension may be adjusted to deliver more or less manipulation pressure; (b) A water jet striking user through a membrane wherein the pump supplying water may be adjusted to provide more or less flow; and (c) A clamping frame pushing user onto a manipulator wherein the clamping force may be adjusted to press the user with more or less force.

Determinants of Force Applied

In dry chair and bed-type massager/cleaners where the manipulators are under the user, the force applied by a manipulator is the weight of the user minus the weight supported by the non-therapeutic area of the chair or bed divided by the number and area of the manipulators. A chair massager supports most of the user's weight with the immobile and non-therapeutic parts of the chair. Only a fraction of the user's weight is supported by the manipulators which protrude through a channel in the back region. One may increase this force by moving this manipulator higher or by disengaging other manipulators.

In dry chair and bed-type massager/cleaners where the manipulators are above the user, the mechanism itself determines the pressing force. This configuration has a greater potential to entrap or injure the user and is rarely used.

Handy type massagers typically apply pressure by the user manually pressing the device into the user. This configuration is fairly safe but requires constant user attention. This lack of automatic control of force applied constitutes a key drawback of conventional manipulator machines.

Bathing Machines

Also known in the art are bathing machines which wash and rub the user with brushes, cloths or sponges as they massage the user. For example, Japanese patent publication number 2001-128880, "Scurf Rubbing and Washing Tool" filed by Misao in 2000 describes a machine which scrubs a standing or lying down human body while applying "finger pressure massage" with brushes, sponges, and towels. Japanese patent publication number 2000-167015, "Washer-Massager for Bathroom" filed by Hiroyuki in 1998 describes a chair which "scrubs and massages a user's back with a towel wound around rollers." The drawback of this invention is that it cannot moderate the intensity of the towel rollers except by adjusting the angle of chair's recline.

Wet massagers typically use water jets to apply therapy. As the human body is largely buoyant, humans weigh on average only 10% of their out-of-water body weight. Hence, a manipulator can apply only a small amount of pressure. Additionally, the user will float horizontally away from the manipulator unless restrained. For this among other reasons, "wet" manipulators (including water jets) apply negligible amounts of force to the user. Hot tubs provide neither therapeutic massage nor assisted movement.

Tilting/Reclining to Control Massage Force

Japanese patent publication number 10-057440, for a "Massage Machine", filed by Kikai in 1996, describes a bed, upon which the user is strapped, which tilts from vertical to horizontal. The bed has a manipulating device (2) and the degree of tilt determines the force this manipulating device applies to the user. This method accomplishes the ability to automatically control the normal force (the force applied by the manipulator) but requires a clamping device (the chest strap) and creates a tangent force inversely proportional to the normal force. When a light manipulation is desired, the user will be mostly vertical and a large amount of weight will be uncomfortably supported by the chest strap.

Conventional dry massage chairs provide for reclining to take advantage of tilting the user back upon manipulators to increase the force thereby applied. For example, Family Corp. FMC-300 Massage Chair allows the back portion to tilt back. In this position, the massaging action is more forceful as more of the user's weight is supported by the manipulators and less of the user's weight is supported by the seat part of the chair. Reclining therefore offers a reasonable method to vary the force applied without requiring a clamping force. This method is limited because users may wish to choose their posture (sitting vs. laying back) independently from the massaging force. Additionally, there is no provision for dynamically varying the tilt angle as the massage device operates.

U.S. Pat. No. 5,587,933 for a "Support Enhancing Device and Associated Method", awarded in 1996 to Gross, describes a chair, bed, shoe, etc. which can be made to conform to an arbitrary user by correctly pressurizing each of a number of inflatable pockets in the appliance.

U.S. Pat. No. 5,792,082 for a "Chair-type Air Massage Device", awarded in 1998 to Yamanaka, describes a chair-type air massage device which has inflatable and deflatable air bags for massaging a user's body part by air pressure causing an expansion and contraction of the air bags. The manipulation intensity is controlled with the same parameter which controls the position control (whose range of movement is inherently limited by the design). For this reason, the intensity has a small dynamic range and has to be chosen to be of low to medium intensity so as not to adversely affect users who cannot accept deeper manipulation.

Japanese patent publication number 2000-279470 for a "Massage Machine" describes a posture correcting device which uses an air piston to pull the user's shoulders backwards towards a chair. This is an example of a "clamping frame" which can induce a sense of vulnerability and/or claustrophobia.

U.S. Pat. No. 5,088,475 for a "Chiropractic Massage Table", awarded in 1992 to Steffensmeier, describes a chiropractic massage table for applying a uniform pressure along the entire length of the spine. The rollers are also mounted so as to float upwardly and downwardly against resistance thereby adjusting the pressure of the rollers to conform to the cervical, thoracic, lumbar and sacral curvatures of the patient's spine. The lifting action is generated by a scissor jack (54) and is controlled by the user with electronic controls.

U.S. Pat. No. 5,792,080 for a "Massaging Apparatus Having Self-adjusting Constant Strength and Non-adjust Strength Modes", awarded in 1998 to Ookawa, describes a massage chair with an automatically controllable cam to control the distance the manipulator projects forwardly (Z-axis) towards the user from the massage carriage while the carriage translates in X and Y axes. In addition, the manipulators are fitted with force sensors whereby the Z-axis position of the manipulators may be dynamically adjusted to maintain a constant application of force on the user. However, adjusting the massage intensity by controlling the amount to which the manipulator protrudes through a stationary chair deforms the user in undesirable ways. In addition, if there are several manipulators, each manipulator must be fitted with this elaborate Z-axis motion actuator and force feedback system.

Pressurized Air to Control Massage Pressure

Japanese patent publication number 2000-342652 for a "Massager Device", filed by Matsushita Electric in 1999, describes a massage chair which uses a bellows-type air piston to push a ball into the user's back. By this means, no driving force exceeding the air pressure is applied to the user. This mechanism has means to control force intensity but not to control position. That is, the pistons will extend until the pressure in the air supply and the reactive force from the user equalize. These pistons also do not have the capability of translating over the user's body.

U.S. Pat. No. 5,741,218 for a "Vertically Reciprocating Pairs of Massage Rings", awarded in 1998 to Fujji, improves upon JP2000-342652 by adding translation capabilities. However, as the air bladder is mounted behind the manipulator, this device also generates undesirable user deformation and requires separate Z-axis motion actuators and force feedback systems for each manipulator if they are to apply force to different areas of the user with individual intensity control.

U.S. Pat. No. 4,976,256 for a "Body Massage Apparatus", awarded in 1990 to Marlin, describes a dry hydromassage table where the user is supported by a tensioned waterproof membrane sealed to the upper part of a box containing upward-facing hydrojets. The box is provided with a fan in order to "slightly pressurize the air within the chamber during use of the massage apparatus to slightly inflate the sheet to enhance the feeling of support to a user laying on the sheet and at the same time to maximize conformity of the sheet to the body of the user." This invention provides for a changeable pressurized support but this does not affect the massage intensity since the impact of the water transmitted through the membrane is unaffected by the air pressure in the chamber. The only effect is to reduce the curvature of the supportive membrane which the author claims would "enhance the feeling of support". This invention also does not anticipate the water buoyancy ideas this disclosure claims. In fact, the author explicitly states that the "massage liquid provides essentially no weight bearing support of the user."

Water Buoyancy

Japanese patent publication number 2001-182347 for a "Warm Bath Facility", filed by Tec in 1999, describes a pool with a floor on which the user stands capable of moving up and down. This "movable floor . . . fluctuates in the domain whose depth of water is 0.3–1.1 m". The therapeutic benefit of this movement is not clear. While this invention automatically controls the user's buoyancy, it does not provide any manipulation.

Japanese patent publication number 08-191872 for a "Jet Bath", filed by Daiichi in 1995, describes a jet bath wherein a person taking a bath is floated in the liquid ejected from a set of nozzles angled upwards from the bottom of the tub in such a way that they do not touch the floor or side walls of the tub.

Japanese patent publication number 2001-198168 for a "Massage Device and Knockdown Bathtub", filed by Osaka Gas Co. in 2000, describes a bathtub with chair type massager "which can perform bathing and massage simultaneously." According to a Japanese-to-English machine translation, it notes that ". . . in order that buoyancy may act on a bathing person's field, it is easy to double with a motion of a massage member and to adjust a bathing person's posture. . . . According to this characteristic feature configuration, the pressure of a massage member can be eased by operation of buoyancy, the soft feeling of a massage can be obtained, and weight can perform the massage."[Means ¶0012] This Japanese publication appears to describe an advantage of massage in water due to buoyancy because this massage device can massage the user without generating pain on the user's massage area/body.

Diving Neutral Buoyancy Balancer

U.S. Pat. No. 5,997,216 for a "Neutral Buoyancy Balancer" awarded in 1998 to Kawashima describes a cylinder worn by a diver which stabilizes diving depth. Increased water pressure associated with an increased diving depth causes water to enter into the cylinder and displace air, increasing density. Decreased water pressure associated with decreased diving depth causes air in the cylinder to inflate, forcing some water to exit the cylinder, decreasing density. While this device makes use of changes in water pressure correlating to the user's respiration cycle, it is not designed as a respiration sensor and has no means to drive other devices which synchronize off the user's breadth. Additionally, it requires the user to immersed at significant depth and to wear a respirator mask. Additionally, this device would react to stabilize the user's depth when perturbed by other forces such as water currents, etc.

U.S. Pat. No. 6,139,512 for a "Method and Apparatus for Water Therapy", awarded in 2000 to Ricchio, describes a person buoyantly supported in a reclining or prone position on a top membrane of a enclosure which contains heated water, and air. A water pump recirculates the water which is drawn out of the enclosure through outlets and associated piping and which is then reintroduced into the interior of the enclosure through venturi air intake as water jets which are mixed with air. The air enriched water jets drive through a layer of water and impinge on the underside of the top membrane to produce massage effects on the person.

The Interactive Health HTT-9C and HTT-10CRP motorized massage chairs move rollers along a curved track so that the massage action can be made to conform to the user's back. The technology Interactive Health uses in their more expensive chairs such as their RMS-11 are rollers mounted in a seesaw configuration, presumably on a straight track. Spring-loading the seesaw mechanism allows the rollers to follow the contours of the body while adapting to users of different heights but tend to apply disproportionate pressure to "outcroppings" such as the user's butt where the change in "elevation" overwhelms the seesaw range-of-motion.

Conventional massage chairs allow the user to adjust the angle of seat back recline both to change posture and to control the weight the user applies to the seat back and hence the massage pressure. However, if the user wants a light massage while fully-reclined, the chair is unable to accomplish this. Solutions mentioned in the prior art suffer from significant drawbacks. One solution is removable upholstered pads, but these pads cannot change through the massage. The pads require manual user intervention and may confuse the user. The pads also clutter the look of the chair. Another solution has been massage manipulators with adjustable force such as described in JP2000-342652, "Massager Device" filed by Matsushita Electric in 1999 which control neither the position of the user nor the supportive force the user receives but instead control the force with which the manipulator actively presses into the user. This requires a complex suspension system with separate piston or bellows for each manipulator. This also requires that all supportive force which is not applied by the manipulator is supplied by the passively supportive chair. This requires the active massage aperture to be small in order to support smaller users around the periphery.

Respiratory-Synchronized Manipulation

Japanese Patent publication number 08-117300 for a "Massaging Machine, awarded in 1996 to Hitoshi et al., describes a massaging machine similar to a massage chair which applies massage synchronously with the user's respiration breathing period. The breadth sensor appears to be a force sensor attached to the massage roller. The invention appears to be a one-sided (non-clamping) Bert-style stethograph and suffers from typical deficiencies of such sensors vulnerability to changes in pressure due to shifting user weight.

U.S. Pat. No. 6,141,590 for a "System and Method for Respiration Modulated Pacing", awarded in 2000 to Renirie et al., discloses a cardiac pacing system that modulates heart rate based on the phases of the patient's respiration. The system includes a respiration sensor, which determines whether the patient is inhaling or exhaling, sensors for right ventricular blood pressure and volume, and a means for producing signals that are delivered to the patient's heart as in conventional cardiac pacing.

U.S. Pat. No. 5,951,500 discloses a device which measures an audio source and varies a vibration massaging unit's intensity to the amplitude of the audio source. This invention does not mention breath sounds as a possible input and would have no obvious means to differentiate between inhalation and exhalation. Nor is it necessarily relevant to modulate the massage intensity to the loudness of breath— the phase is more therapeutically relevant.

U.S. Pat. No. 5,266,070 discloses a device which measures the degree of relaxation of a user and delivers various refreshing stimulus in response to the measurement. In this invention the sensor called out is an electrocardiogram and the time scale of the measurements would be 3 seconds. It calls for an overall measurement of relaxation and not a breath cycle specific sensing. This does not account for the inhalation and exhalation of the user and the corresponding desired modifications to the massaging stroke and intensity.

U.S. Pat. No. 5,395,301 for a "Kinesthetic system for Promoting Rhythmic Breathing by Tactile Stimulation" describes an invention that strokes a patient on a ventilator in rhythm with the ventilator in order to facilitate harmonious assisted breathing. When the device is disconnected from the ventilator it is only used as a breath coach to achieve a desired breathing pattern. When the device is attached to the ventilator and the stroking is in time to the user's breathing, that breathing is a function of the ventilator and not of the user.

U.S. Pat. No. 6,251,048 for an "Electronic Exercise Monitor" describes an exercise sensor that provides motivation for completing an exercise routine by producing verbal encouragement. One of the exercise sensors described is a breathing sensor. While the various devices described above may adequately perform their intended purposes to some degree, they have many disadvantages as noted. Accordingly, there is a need in the art for an improved device and method for manipulating a user.

SUMMARY OF THE INVENTION

In accordance with one aspect of the present invention, a device for manipulating a user, includes a manipulator, a translator for moving the manipulator along at least one axis to apply a manipulation to the user, and means for changing an intensity of the manipulator while providing spatially uniform support to the user outside a contact patch of the manipulator.

From the foregoing disclosure and the following more detailed description of various preferred embodiments it will be apparent to those skilled in the art that the present invention provides a significant advance in the technology and art of massage or manipulation devices. Particularly significant in this regard is the potential the invention affords for providing a high quality, reliable, low cost device which provides a pleasurable experience for the user. Additional features and advantages of various preferred embodiments will be better understood in view of the detailed description provided below.

BRIEF DESCRIPTION OF THE DRAWINGS

These and further features of the present invention will be apparent with reference to the following description and drawings, wherein:

FIGS. 11 to 14 are elevational views of the manipulator of FIG. 4 wherein the manipulator is heated or cooled by means of an electrical resistance heater, a Peltier device, a nozzle, and a circulation loop respectively;

FIG. 42 is an elevational side view of a manipulation device according to a fourth embodiment of the present invention having a massage chair wherein the force of the massage is regulated by an adjustable air pad;

FIG. 43 is a diagrammatic view of the air pad of FIG. 46 showing the air pad in a highly inflated state and the resulting supportive force distribution on a back;

FIG. 44 is a diagrammatic view of the air pad of FIG. 43 showing the air pad in a lesser inflated state and the resulting force distribution;

FIGS. 48, 49, and 50 are elevational views of a tracked kneading manipulator which can be utilized with each of the embodiments of the present invention;

DESCRIPTION OF THE PREFERRED EMBODIMENTS

Within the specification and claims, terms have the following meanings. The term "ventral" means toward the belly or front. The term "dorsal" means toward the back. The term "rostral" means toward the nose. The term "caudal" means toward the tail. The term "superior" means toward the top of the body. The term "inferior" means away from the top of the body. The terms "lateral" and "distal" mean away from the middle. The terms "medial" and "proximal" mean toward the middle. The term "bilateral" means on both sides. The term "ipsilateral" means on the same side. The term "contralateral" means on the opposite side. The term "supine" means lying on the back or with the face upward. The term "prone" means a position with the front of the body turned toward the supporting surface. The term "fluid" means a gas, liquid, or mixture thereof. For example, a bladder may be filled with water and air, water and gel, or some other combination. The term "working fluid" is any fluid used to pressurize a membrane or bladder and/or to provide buoyant support. All pressures noted in units of "psi" shall be construed to be relative to the atmosphere ("psig"). The term "therapeutic physical manipulation" shall mean massage, physical therapy, water massage, water dance (such as assisted submersion or dunking), assisted stretching or any related form of therapy supplying tactile stimulation, skeletal muscle manipulation, and joint range-of-motion exercises.

Figure 1:
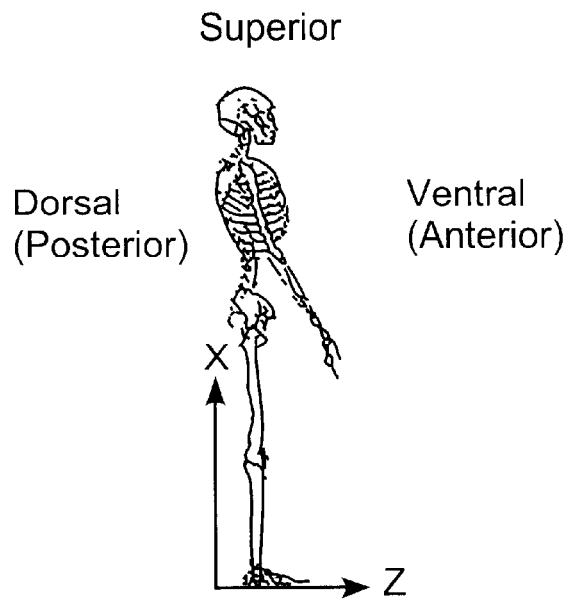
FIGS. 1 and 2 are diagrammatic views of a human body human body.
Figure 2:
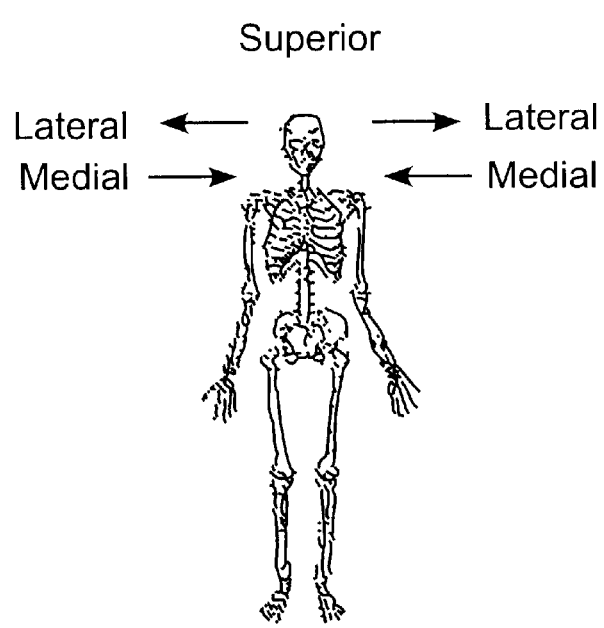

As best shown in FIGS. 1 and 2, within the specification and claims the term the "X-axis" shall mean an axis extending along the superior to inferior axis of the user's body, increasing in the superior direction. If the user's body is bent (e.g. at the knees and hips), the X-axis shall follow the user's dorsal profile from feet to head along this curvilinear path, increasing in the head direction. The term the "Y-axis" shall mean an axis extending along the lateral to medial axis of the user's body, bilaterally increasing in the lateral direction with an origin at the user's centerline. The term the "Z-axis" shall mean an axis extending along the dorsal to ventral axis of the user's body, increasing in the ventral direction.

Figure 3:
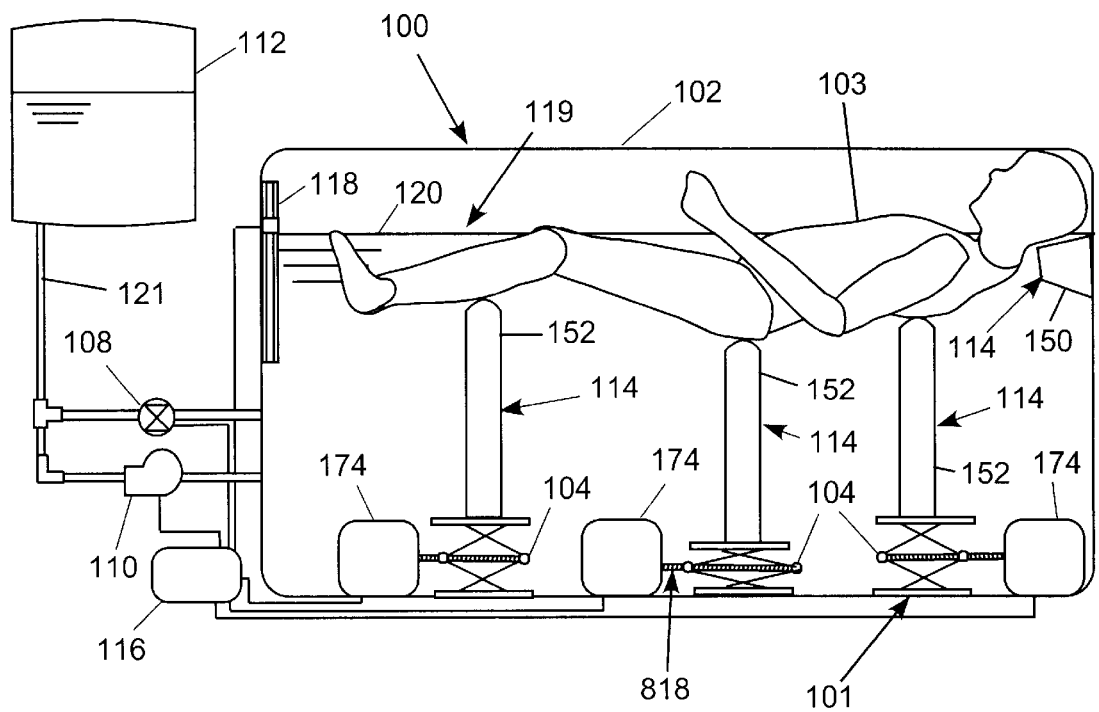
FIG. 3 is an elevational view of a manipulation device according to a first embodiment of the present invention having a tank which changes the user's level of buoyant support by either raising or lowering the user in the water or by raising or lowering the water level of the tank.

FIG. 3 illustrates a therapy and/or manipulation device 100 having dynamic intensity control according to the present invention. The illustrated manipulation device 100 includes a massage tank or tub 102 containing a working fluid 119, a plurality of manipulators 114 adapted to engage a user 103; means 101 for changing a pressure intensity of the manipulators 114 while providing spatially uniform support to the user 103 outside contact patches of the manipulators 114 to selectively vary the pressure intensity at which the manipulators 114 engage the user 103, a translator 800 (FIG. 15) for moving the manipulators 114 along at least one axis to move the manipulators along a surface of the user 103 to apply a manipulation to the user 103, and a controller 116 for operating the pressure intensity changing means 101 and the translator 800. The illustrated tank 102 has a bottom wall and four side walls upwardly extending from the edges of the bottom wall to form a sealed enclosure having an open top. The 102 tank is preferably sealed liquid tight to contain the working fluid 119. The working fluid 119 is preferably a liquid such as, for example, water and the working fluid 119 is preferably warm to hot, that is in the temperature range of about 98° to about 108° Fahrenheit.

Figure 15:
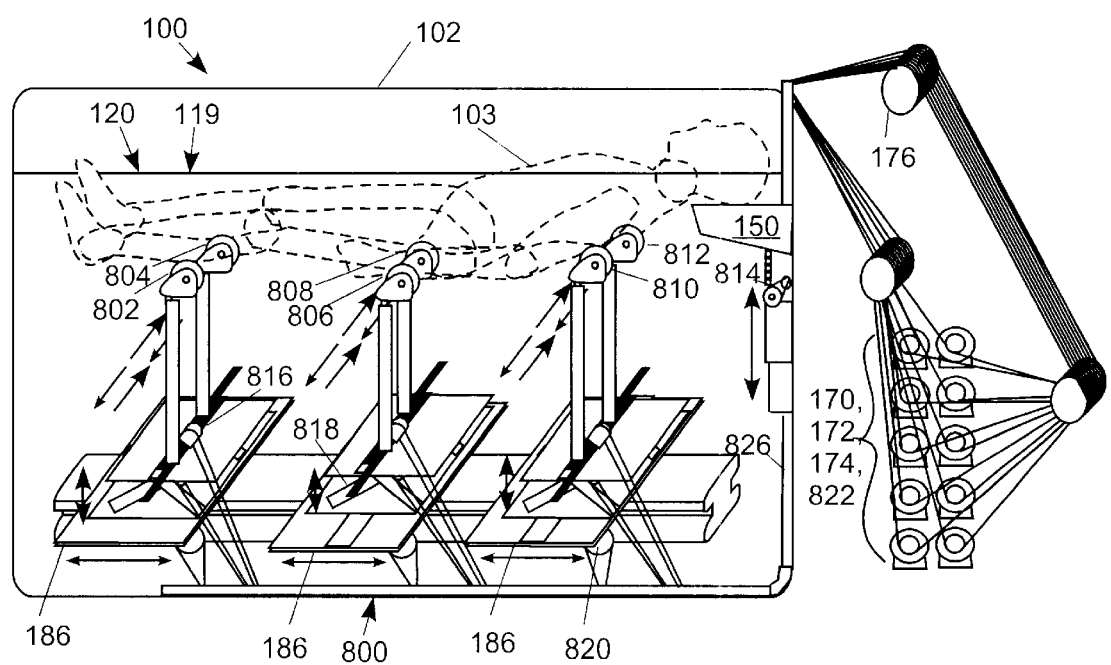
FIG. 15 is an elevational side view of the device of FIG. 3 showing a translator in the form of a cable drive system.

The illustrated manipulation device 100 includes seven manipulators 114, a head support 150 and three pairs of posts 152, located within the tank 102 below the user 103 and typically within the working fluid 119. The posts 152 initially support a reclined user 103 behind each calf, each gluteus, and each shoulder. The head support 150 forms a pillow for the user 103. The manipulators 114 are preferably positioned so the user 103 is partially submerged in the working fluid 119 such that the ventral part of the head and torso of the user 103 are above the working fluid 119 and the rest of the body of the user 103 reclines in a comfortable posture. The posts 152 are grouped in three pairs referred to as a "leg pair" 802, 804 (FIG. 15), a "gluteus pair" 806, 808 (FIG. 15), and a "torso pair" 810, 812 (FIG. 15). It is noted, however, that the manipulators 114 can move from their nominal or initial position—e.g. the gluteus pair can join the torso pair in manipulating muscles of the back of the user 103.

Figure 4:
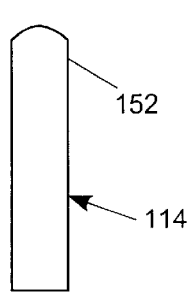
FIG. 4 is an elevational view of a manipulator of the device of FIG. 3 wherein manipulator is in the form of a post having zero degrees of rotational freedom.
Figure 5:
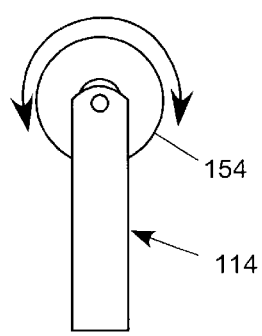
FIG. 5 is an elevational view similar to FIG. 4 but showing an alternative manipulator having a roller with one degree of rotational freedom.
Figure 6:
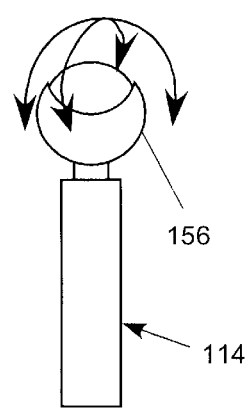
FIG. 6 is an elevational view similar to FIGS. 4 and 5 but showing another alternative manipulator having a track ball with two degrees of rotational freedom.
Figure 7:
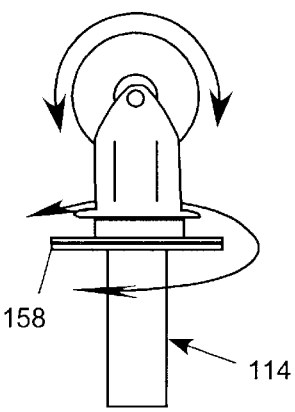
FIG. 7 is an elevational view similar to FIGS. 4 to 6 but showing yet another alternative manipulator having a caster with two degrees of rotational freedom.
Figure 8:
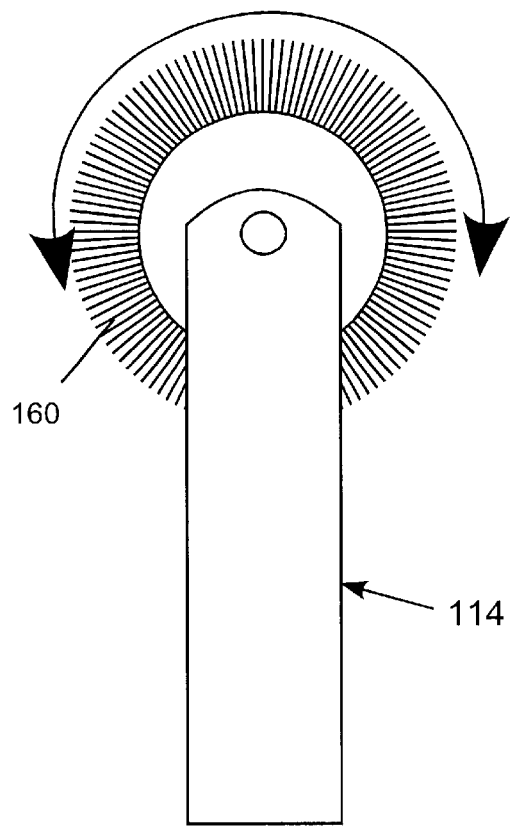
FIG. 8 is an elevational view similar to FIGS. 4 to 7 but showing yet another alternative manipulator having a brush roller with one degree of rotational freedom.
Figure 9:
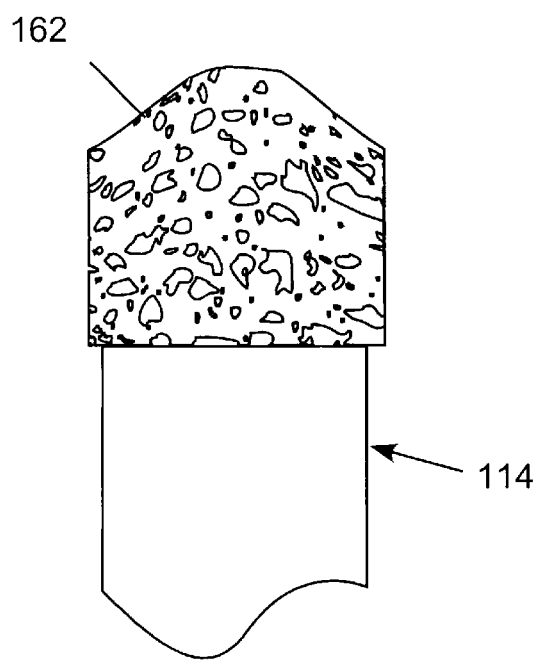
FIG. 9 is an elevational view similar to FIGS. 4 to 8 but showing yet another alternative manipulator having a sponge-tip with no degrees of rotational freedom.
Figure 10:
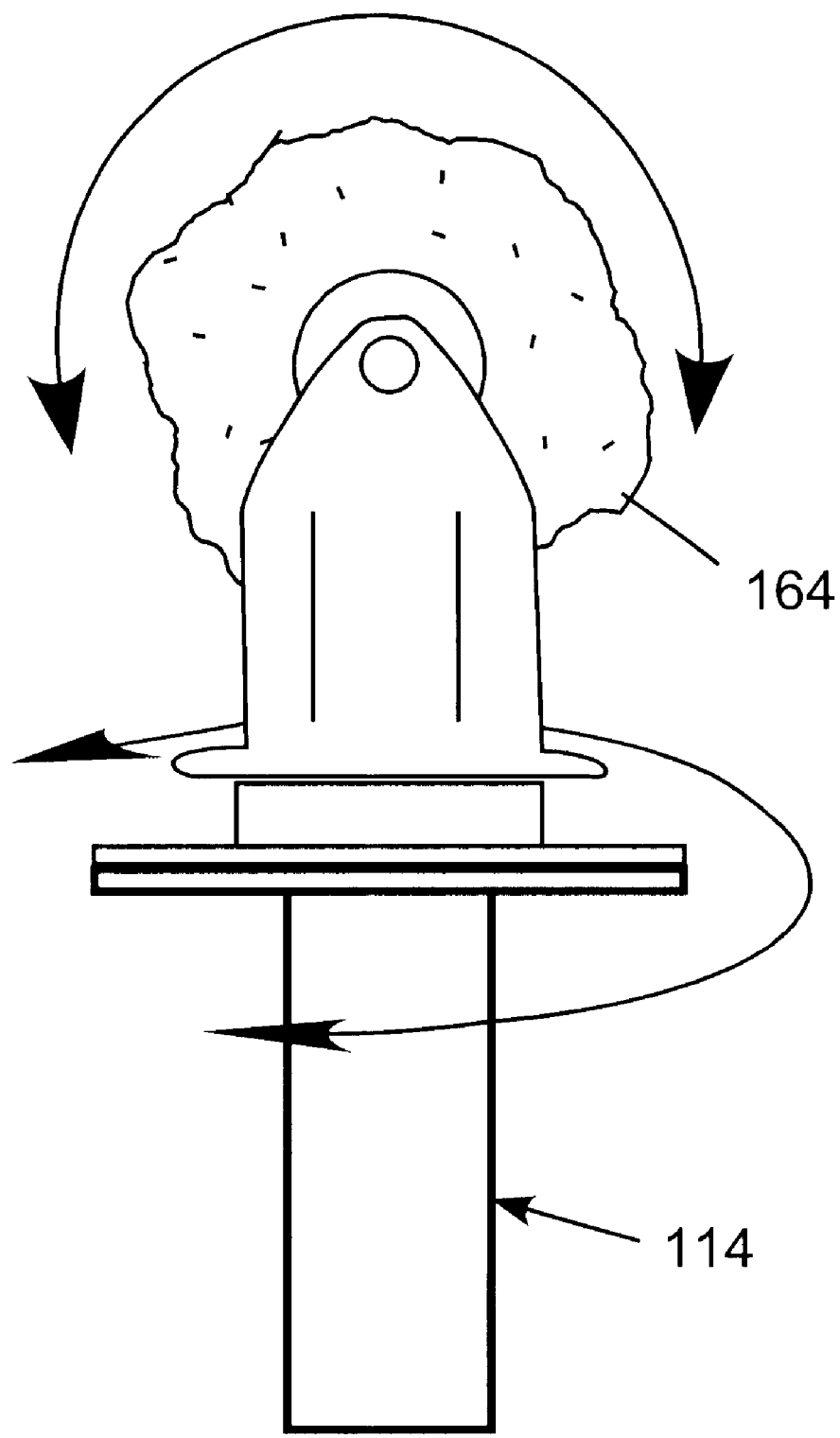
FIG. 10 is an elevational view similar to FIGS. 4 to 9 but showing yet another alternative manipulator having a towel-clad wheel with two degrees of rotational freedom.

FIG. 4 illustrates one of the manipulators 114 in the form of the post 152 having zero degrees of freedom. FIGS. 4 to 10, illustrate that the posts 152 can be configured in many ways such as, for example, the post 152 can be provided with a roller 154 having a single degree of freedom, that is, rotatable about an axis (FIG. 5), the post 152 can be provided with a trackball 156 having three degrees of freedom, that is, rotatable about three axes (FIG. 6), the post 152 can be provided with a caster 158 having two degrees of freedom, that is, rotatable about two axes (FIG. 7), the post 152 can be provided with a brush roller 160 having a single degree of freedom, that is, rotatable about one axis (FIG. 8), the post 152 can be provided with a sponge-tip 162 having zero degrees of freedom (FIG. 9), and the post 152 can be provided with a towel caster 164 having two degrees of freedom, that is, rotatable about two axes (FIG. 10). The sponges, brushes, and other implements of bathing can be used as contact elements for the manipulators 114 to apply both pressure and a rubbing/scrubbing action to remove grime, exfoliate the skin of the user 103, and invigorate the user's tactile senses. The manipulators 114 can rotate or pivot in zero, one, two, or more axes. The manipulators 114 can be rigid such as formed of a hard plastic, flexible such as formed of a soft rubber, or conformable such as formed by an inflatable bladder. The contact surface of the manipulators 114 can be smooth or rough and can be capable of cleaning a user such as, for example, provided with a brush, sponge, or towel.

As best shown by FIGS. 11 to 14, the manipulators 114 may be heated or cooled by means of an electrical resistance heater 165 (FIG. 11), a Peltier heater or cooler 166 (FIG. 12), a nozzle 167 for ejection of heated or cooled fluid (FIG. 13), a fluid circulation loop 168 for circulation of heated or cooled fluid (FIG. 14), and or the like. While the heating and cooling means are illustrated with respect to the post 152 having zero degrees of freedom, each can be utilized with the post 152 in any other configuration and/or any other type of manipulator 114.

It is noted that a fewer or greater number of manipulators 114, as long as there is at least one manipulator 114, can be utilized and that different combinations of types of manipulators 114 can be utilized. For example, the manipulators 114 can consist of a head support 150 and six posts 152 (FIG. 3). These posts 152 are preferably constructed of a lubricous plastic and slide along the user 103. The manipulators 114 can consist of a head support 150 and six rollers 154 (FIG. 15). Preferably, the rollers 154 initially support a reclining user 103 (FIG. 15) and translate in three dimensions—X, Y, and Z—rolling along the user 103 to apply massage, to control the user's posture for purposes of assisted stretching, and to govern the user's eminence above the working fluid level 120. The manipulators 114 can consist of a head support 150 and six trackballs 156. The manipulators consist of a head support 150 and six sponge-tipped posts 162. The sponge tipped posts 162 slide along the user's body. The manipulators 114 can consist of a head support 150 and six posts 152 supporting a reclining user through a membrane, as described in more detail hereinafter. The post 152 and membrane materials are specified to minimize friction there between, allowing the posts 152 to easily slide beneath the membrane. Rollers 154 and trackballs 156 may also be made to apply manipulations through the membrane. Other quantities and combinations of the manipulators will be apparent to those skilled in the art given the benefit of this disclosure.

The illustrated means 101 for changing the pressure intensity of the manipulators 114 includes components which raise and lower the user 103 relative to the surface level 120 of the working fluid 119. At least some of the manipulators 114, all six of the posts 152 in the illustrated embodiment, are carried by Z-axis actuators 818 which selectively raise and lower the manipulators 114 toward and away from the user 103 to selectively raise and lower the user 103 relative to the working fluid level 120. The illustrated Z-axis actuators 818 are in the form of scissor-type jacks 104. Motors 174 are operatively connected to screw shafts 190 (FIG. 16) of the scissor-type jacks 104 and independently control movement of the scissor-type jacks 104 to raise and lower the manipulators 114. In the illustrated embodiment each scissor-type jack 104 carries a pair of the manipulators 114 but each jack 104 can alternatively carry a fewer or greater number of the manipulators 114. It is noted that other suitable types Z-axis actuators and other suitable types of jacks can be utilized to raise and lower the manipulators 114 such as, for example, telescoping devices, piston/cylinder devices and ratchet devices. The user 103 lies within the tank 102 upon the upper end of the manipulators 114 so that the user 103 is partially supported by the manipulators 114 and partially supported by the working fluid 119. As the manipulators 114 are raised and lowered by the scissor-type jacks 104, the user 103 is raised and lowered relative to the surface level 120 of the working fluid 119.

The manipulation device 100 automatically and dynamically varies the extent to which the user 103 is submerged in the working fluid 119 and consequently controls the user's buoyancy, the user's apparent weight, and hence the force applied by the manipulators 114 to the user 103. The Archimedes Principle states that the buoyant force on a submerged object is equal to the weight of the fluid that is displaced by the object. When the user 103 is fully submerged in the working fluid 119, the buoyant force is maximized as the user 103 displaces a maximal amount of working fluid 119. When the user 103 is suspended fully above the working fluid 119, displacing no working fluid 119, the buoyant force is minimized.

The manipulators 114, which move under the control of the controller 116, vertically move the user 103 such that a greater or lesser portion of the user 103 is submerged in the working fluid 119. Lifting a greater portion of the user 103 out of the working fluid 119 reduces the buoyancy effect and increases the force applied by the manipulators 114 onto the user 103. Contrariwise, descending the manipulators 114 and allowing a greater portion of the user 103 to submerge into the working fluid 119 increases buoyancy and reduces the force applied by manipulators 114 onto the user 103. The minimum amount of force the manipulators 114 apply to the user 103 depends on how much of the user 103 must remain above the working fluid 119 for comfort reasons and the relative densities of the user 103 and the working fluid 119. The relevant typical densities in kilograms per liter of bone is 1.80; muscle is 1.05; fat is 0.94; water is 1.00; and air is 0.00. These combine to a density for an average person of slightly less than the density of water. Muscular people and skinny people have high densities and are poor floaters. Woman typically contain more fat than men—they have lower densities—and are good floaters. For example, allowing all but a small area around the mouth and nose of the user 103 to submerge may reduce the supportive force to about one pound when lungs are inflated. If breathing comfort of the user 103 requires the full head of the user 103 to be out of the working fluid 119, the user 103 might require about twenty pounds of supportive force from the manipulators 114. Lifting part of the user's torso out of the working fluid 119 in addition to the user's head may increase the supportive force to about forty pounds. Denser or more massive users 103 may require support in addition to the manipulators 114.

Instead of using the manipulators 114 to vertically move the user 103 relative to the surface level of the working fluid 119, the manipulators 114 can alternatively remain stationary and the surface level 120 of the working fluid 119 can be moved relative to the user 103. Thus, the means for changing the pressure intensity of the manipulators 114 can comprise components which change the working fluid surface level 120 in the massage tank 102. Changing the surface level 120 of the working fluid 119 can be accomplished by pumping and/or using gravity and valves to transfer the working fluid into and out of the portion of the massage tank 102 supporting the user 103, that is, changing the volume of working fluid 119 within the tank 102. In the illustrated embodiment, a fluid holding tank 112, located vertically higher than the massage tank 102, is connected to the massage tank 102 via conduits 118 having a valve 108 and a pump 110 respectively. When the valve 108 is opened, working fluid 119 flows by gravity from the higher holding tank 112 to the massage tank 102 to raise the working fluid level 120 in the massage tank 102. When the pump 110 is activated, working fluid 119 flows from the massage tank 102 to the holding tank 112 to lower the working fluid level 120 in the massage tank 102. It is noted that alternatively, the holding tank 112 could be positioned lower than the massage tank 102 so that the working fluid 119 is transferred to the holding tank 112 by gravity and transferred from the holding tank 112 by pumping. It is also noted that the working fluid 119 could also be transferred in both directions by either pumping or gravity. The micro-controller 116 is operatively connected to the valve 108, the pump 110, and a working fluid level sensor 118 to control the level of the working fluid 120 relative to the manipulators 114.

The translator 800 moves each of the manipulators 114 in at least one axis generally parallel to a surface of the user 103, that is an axis other than the Z-axis, to move the manipulators 114 to different contact locations along the surface of the user 103 to manipulate the user 103 in the form of a massage. Preferably, the translator 800 moves the manipulators 114 in both the X-axis and the Y-axis, that is each axis perpendicular to the Z-axis, and cooperates with the Z-axis actuators 104. As best shown in FIG. 15, the illustrated translator 800 includes an X-axis actuator 820 and a Y-axis actuator 818 which cooperate with the Z-axis actuator 104 for each of the post type-manipulators 114 and a head rest linear actuator 814 for the head 150. Each pair of manipulators 114 move together as a unit in the same direction along the X-axis (that is along the users centerline), move together but in opposite directions in the Y-axis (transverse to the user's centerline), and move together as a unit in the same direction along the Z-axis. The headrest 150 is fixed in both the X-axis and the Y-axis but can move up and down toward and away from the user 103 in the Z-axis to accommodate postural changes of the user 103 due to movement of the other manipulators 104.

Figure 16:
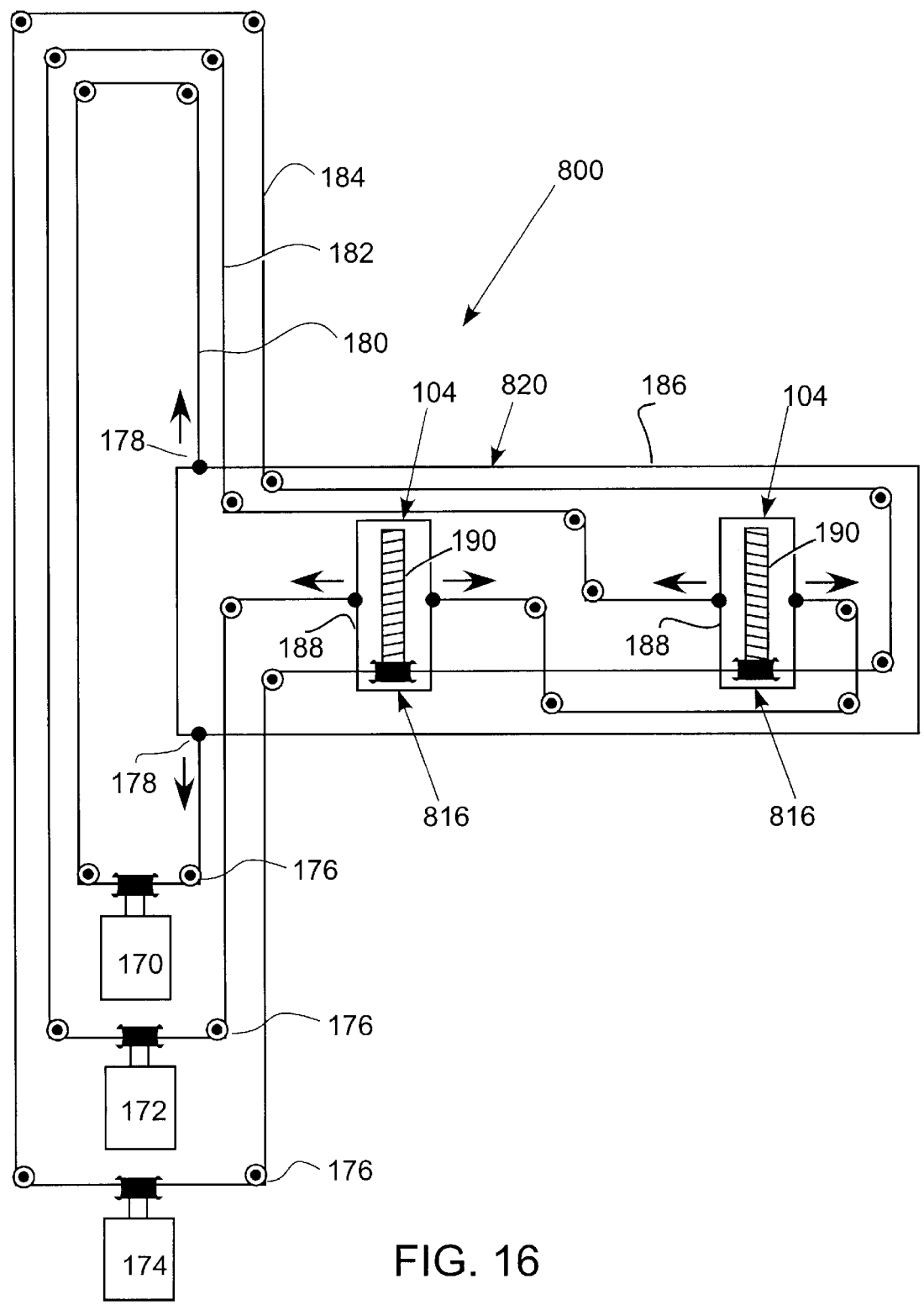
FIG. 16 is a schematic view of a portion of the cable drive system of FIG. 15 for a pair of the manipulators.

As best shown in FIGS. 15 and 16, the illustrated X-axis actuator 820 includes three X-axis linear motion carriages 186 which are of the rack and pinion type. The illustrated Y-axis actuator 816 includes six Y-axis linear motion carriages 188 which are of the ball and screw type. The illustrated Z-axis actuator 818 includes six of the scissor-type jacks 104. The three pairs of manipulators 114 plus the headrest 150 of the illustrated embodiment utilize ten motors 822, three motors 170, 172, 174 for each pair of manipulators 114 and one motor 822 for the head rest 150. The motors 170, 172, 174, 822 are preferably positioned outside of the tank 102 superior to the user's head and drive the manipulators 114 via cable linkages as described hereinafter. The cables 180, 182, 184 preferably extend into and out of the tank 102 through the open top and along the inner surface to the bottom of the tank 102. Preferably, suitable guide housings 826 are provided for the cables 180, 182, 184. Each jack 104 is capable of applying the maximum force which users find comfortable for that particular type of manipulator 114 which is being adjusted. For example, the force for a roller 154 having a size of about one inch in width and three inches in diameter is approximately thirty pounds force. The motors 170, 172, 174, 822 preferably provide sufficient torque to move the manipulators 114 at least one or two inches per second. While additional actuators would be desirable to control the roller 154 direction, in order to reduce the number of actuators, the rollers 154 are mounted on passive swivels with encoders to allow the controller 116 to know their direction. To reorient the roller 154, the controller 116 rolls the roller 154 along a curved path on the user 103. An even less expensive solution is to provide no encoder but to use knowledge of prior movements to determine the likely orientation of the roller.

FIG. 16 illustrates a preferred drive arrangement for one of the three pairs of manipulators 114. The motors 170, 172, 174 preferably drive the manipulators 114 via cable drive. The X-axis motor 170 drives the X-axis carriage 186 via a cable 180 guided by free spinning pulleys 176 and anchored to the carriage 186 at fixed anchor points 178. The X-axis motor 170 moves the carriage 186 by pulling directly in the positive X-axis direction and pulling through one of the pulleys 176 mounted inferior to the user's feet for the negative X-axis direction. The Y-axis motor 172 drives the Y-axis carriages 188 in opposite directions via a cable 182 guided by free spinning pulleys 176 and anchored to the carriage 186 at fixed anchor points 178. The Y-axis cable 182 passes through series of the pulleys 176 to move the pair of manipulators 144 laterally or medially to the user 103. When the X-axis carriage 186 moves, the Y-axis motor 172 must move at the same rate to keep the Y-axis carriages 188 stationary. It is the relative motion of the X-axis and Y-axis motors 170, 172 that cause the manipulators to move in the Y-axis. The Z-axis motor 174 moves the scissor-type jack 104 via a cable 184 guided by free spinning pulleys 176. The Z-axis cable 184 rotationally drives a screw drive 190 of the scissor jacks 104. The Z-axis motor 174 must be synchronized to both the X-axis and Y-axis motion as it is the relative motion of the Z-axis motor to the X-axis and Y-axis motors 170, 172 that cause the manipulators 114 to move in the Z-axis. Together, the three pairs of manipulators 114, preferably translate in three degrees of freedom, move along the user 103 to apply massage, control the posture of the user 103 for purposes of assisted stretching, and govern eminence of the user 103 above the working fluid surface level 120 for buoyancy control. Preferably, end-of-travel switches and rotational encoders mounted on each motor 170, 172, 174, 822 provide position feedback to the controller 116. It is noted that the translator 800 can alternatively utilize other types of drive systems such as, for example, when electrical safety allows, some or all of the motors 170, 172, 174, 822 can be mounted closer to the manipulators 114 in the tank 102 and drive the manipulators 114 directly or via belts or gears. Additionally, pneumatic or hydraulic actuators may be alternatively used.

Figure 17:
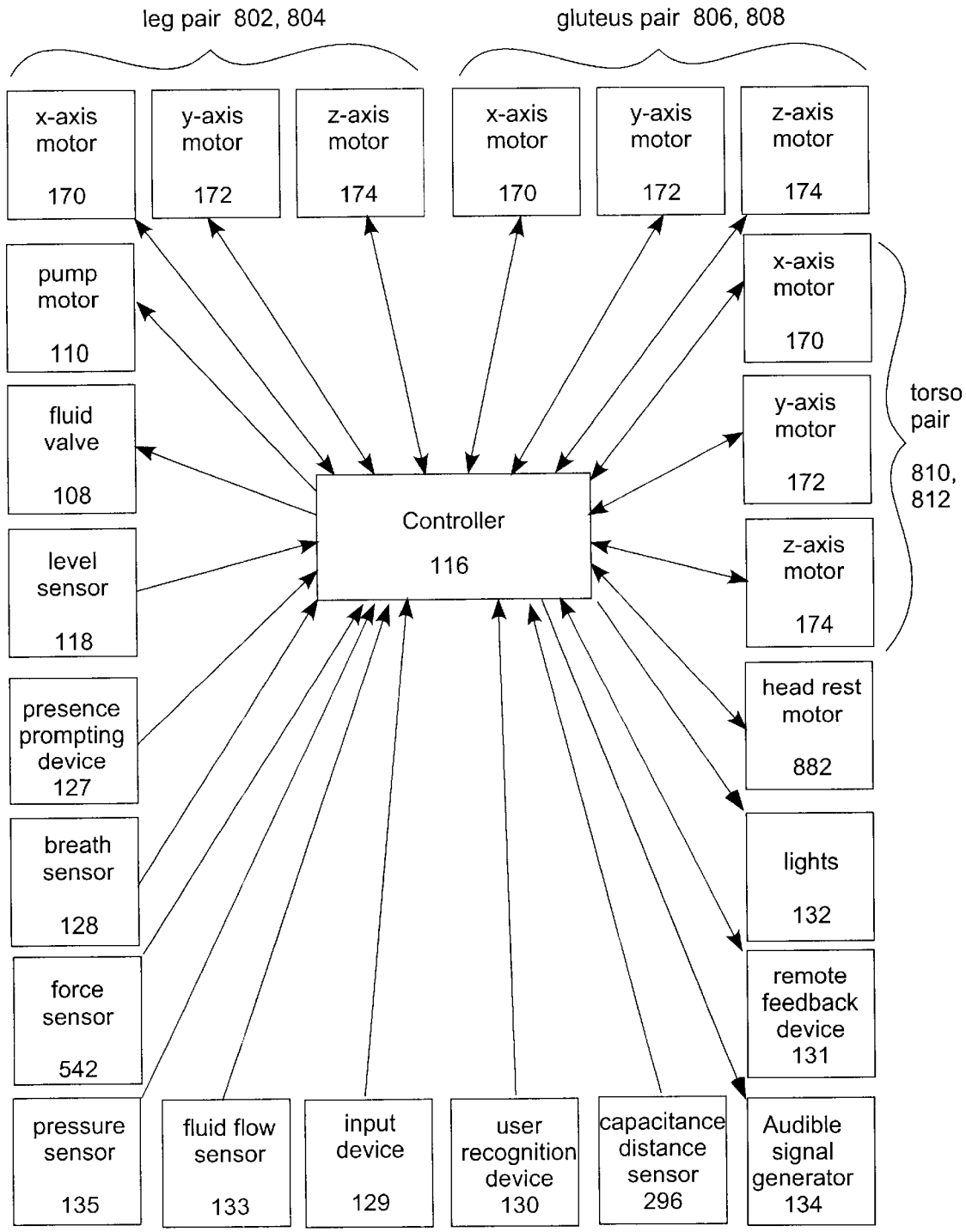
FIG. 17 is schematic view of a control system of the device of FIG. 3.

The micro-controller 116 is preferably a programmable system, such as a computer, but alternatively can be an embedded system or a combination. As best shown in FIG. 17, the controller 116 communicates with various components of the device 100 as part of a control system. The controller 116 is operatively connected to the motors 170, 172, 174, 882 to control movement of the actuators 816, 818, 820 and thus movement of the manipulators 114. The controller also is operably connected to other components to control and synchronize motions of the fluid pressure or level, and/or tensioning as discussed hereinafter. Depending on the hardware configuration, the controller 116 may control electric, pneumatic, hydraulic, or other motors to move the manipulators along linear or curvilinear paths to approximate kneading and tapping strokes and shiatsu static pressure points. Some motions may require coordinating multiple actuator axes such as the X-axis and the Y-axis to produce circular kneading strokes. Alternatively, a single actuator may be used to produce such non-linear stroking at the cost of reducing the generality of the system. To make the system most general (able to produce arbitrary manipulation motions), each manipulator 114 preferably has a separate actuator for each axis of motion. However, in order to reduce cost, different manipulator motions may be controlled by the same actuator. For example, manipulators 114 are paired so a single actuator controls the X-axis of both manipulators (they move together in the X-axis) and a single actuator controls the Y-axis of both manipulators as discussed above with reference to the illustrated embodiment.

It is noted that the controller 116 can maintain a desired manipulation pressure by utilizing a force sensor 542 such as, for example, the "RDP Group Model 31 Precision Miniature Tension/Compression Load Cell" located under the manipulator 114 in order to control the Z-axis position of the manipulator 114 or the support pressure in an air bladder, tensioned membrane, or buoyancy water level. This set point may change under computer control as the manipulator 114 moves to achieve firmer manipulation in more muscular, less-sensitive areas than in bonier, more-sensitive areas. Alternatively, a pressure sensor 135 measuring the fluid pressure in the air bladder may be utilized to determine manipulation intensity when used with an air pad or pressurized enclosure. The controller 116 may alternatively maintain desired manipulation pressure by utilizing a fluid flow sensor 133. In this case, the controller 116 would integrate the flow measurement to determine fluid volume in a fluid-filled bladder. The controller 116 could periodically reset its calculated volume by using the compressor in suction mode to pump down the fluid-filled bladder. The controller 116 may alternatively maintain desired manipulation pressure by utilizing a capacitance distance sensor 296 to measure the distance between any two membranes in a fluid-filled bladder.

The controller 116 and other components can be configured to perform many different types of manipulations on the user 130. For example, the pairs of manipulators 114 can act symmetrically across the user's centerline as described above. Alternatively, the pairs of manipulators 114 can act independently, allowing torsion stretches (twisting along centerline) by engaging upper manipulators to one side of the centerline more prominently than the other side and counteracting tendency to fall off by more strongly engaging the opposite side of hip/leg pair of manipulators 114.

Also, the controller 116 can be adapted to raise at least some of the manipulators 114 to a loading position when the device 100 is unoccupied or an occupation is anticipated in the near future. This anticipation may be triggered by a user key press, a motion sensor, or some other suitable presence prompting device 127. With the manipulators 114 raised to the loading position, the user 103 may more easily seat or repose herself upon the manipulators 114. When the user's presence is detected upon the manipulators 114 or at the commencement of the manipulation, the manipulators 114 are descended into an operating position. At the conclusion of the manipulation session, the manipulators 114 may automatically ascend to the loading position to help the user 103 egress from the device 100.

When the user 103 is at least partially supported by the buoyant working fluid 119, the user 103 may perform exercises, using body weight as the resistance force and with the ability to modify this body weight by varying the buoyant effect. For example, a user 103 partially immersed in a working fluid 119 and lying supine on manipulators 114 can perform exercises such as abdominal curls using the user's torso as the moving weight. Since the user's torso is partially immersed, it weighs less than it would without the buoyant support. By moving the working fluid level 120 relative to the user 103 (or moving the user 103 relative to the working fluid level 120), exercise effort may be adjusted. Exercises with small range-of-motion such as isometric exercises, such as isometric contractions are particularly well-suited to this type of configuration.

Isometric contractions refer to contractions in which the length of muscle remains the same (neither lengthening or shortening). Pushing against a wall or statically flexing a muscle are examples of isometric contractions. Isometric exercises can increase strength but only at the specific range of motion that the muscle was position in during the contraction. This limits the use of isometrics for sport specific applications; however, they are still used clinically and can be used by the general population as an adjunct to a resistance training program. However, if isometric contractions are performed at multiple positions through a range of movement, strength may be increased through the range of movement. Manipulators 114 such as those depicted in FIG. 3 may be used to move the user 103 to various positions and an audio signal generated by the controller 116 can prompt the user 103 to initiate a specific isometric contraction. The working fluid level 120 can adjust the force required by the user 103 to hold that contraction.

The controller 116 can be adapted to control the manipulators 114 may make use of the viscosity of the working fluid 119 by "dropping" and then "catching" the user 103. In order to "drop" the user 103, the manipulator 114 is moved down faster than the user's body falls. The more viscous the working fluid 119, the slower the user 130 falls. The manipulator 114 can "catch" the user 103 by descending slower than the user 103 is falling.

When the manipulator 114 contacts the user 103 again on the same patch of skin or same location, the drop-catch action can provide a form of tapping massage and/or allow tension in the user's skin to recover after a kneading stroke. By "recover", it is meant that a post-type manipulator 152 (FIG. 4) dragging along the user's skin in the X-axis and/or Y-axis will build up a fold of flesh ahead of the manipulator's travel path. If the relative friction is too great, this fold will eventually cause a painful pinching sensation. To allow this fold of flesh to relax while continuing the desired travel path of the manipulator 114, the controller 116 can momentarily disengage the manipulator from the user's skin. Additionally, the manipulator 114 can move in the X-axis and/or the Y-axis while that portion of the user's body is in free fall, allowing the manipulator 114 to move without contacting the user 103. Furthermore, the manipulator 114 can stay in partial contact with the user 103 throughout a fall and make use of the fall to temporarily reduce the user's apparent weight.

The controller 116 is preferably adapted to control the massage based at least in part on feedback from a user's breath patterns to adjust the massage on short and long time scales. Professional masseuses are trained to monitor their subjects breathing and modify the massage accordingly. Breathing is a unique body function since it is under voluntary as well as involuntary control, and of untapped value as an automatic massager control input. Breath has been described as a bridge between the conscious and unconscious mind, a window into the state of a persons being. Preferably, a user 103 can direct the style and intensity of the manipulation with each breath, consciously or unconsciously, as the user 103 relaxes into the massage.

Figure 55:
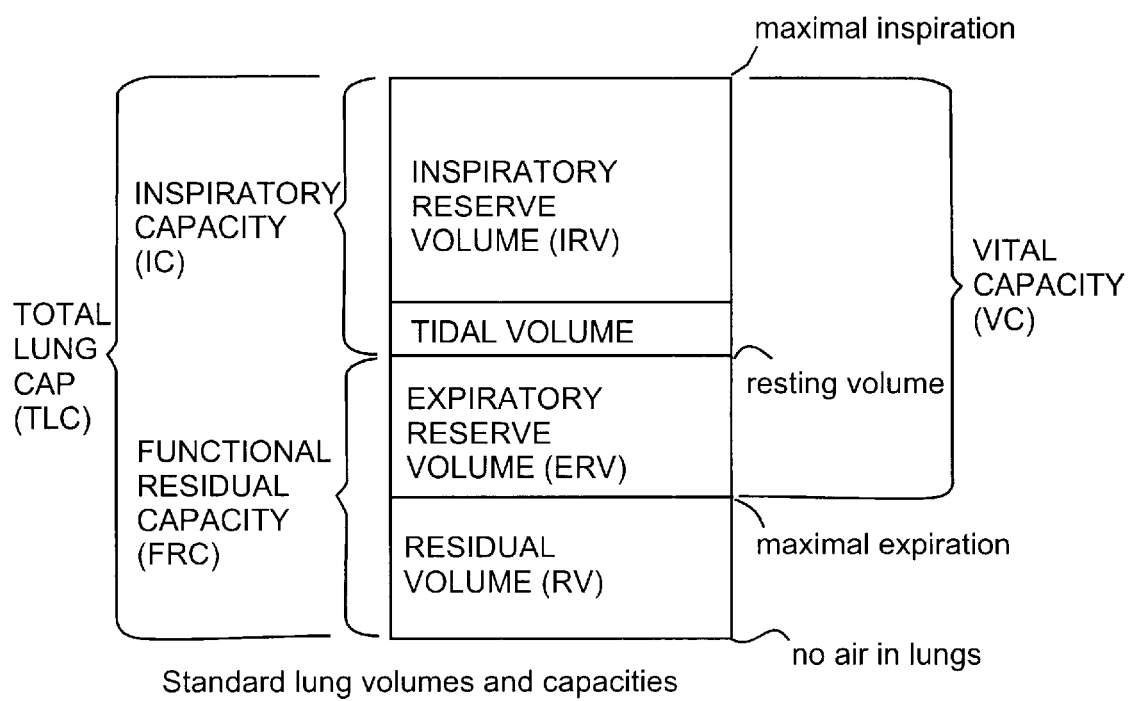
FIG. 55 is diagram showing standard lung capacities.

FIG. 55 illustrates that the standard lung capacity (TLC) is the difference between the volume of air at maximal inspiration into the lungs and no air in the lungs. The TLC is the product of inspiratory capacity (IC) and functional residual capacity (FRC). The IC is the product of inspiratory reserve volume (IRV) and tidal volume. The FRC is the product of expiratory reserve volume (ERV) and residual volume (RV). Thus, the RV is the volume at maximal expiration. Resting volume is the product of ERV and RV, that is, equal to the FRC. Vital capacity (VC) is the TLC less the RV, that is the product of the IC and the ERV.

Figure 56:
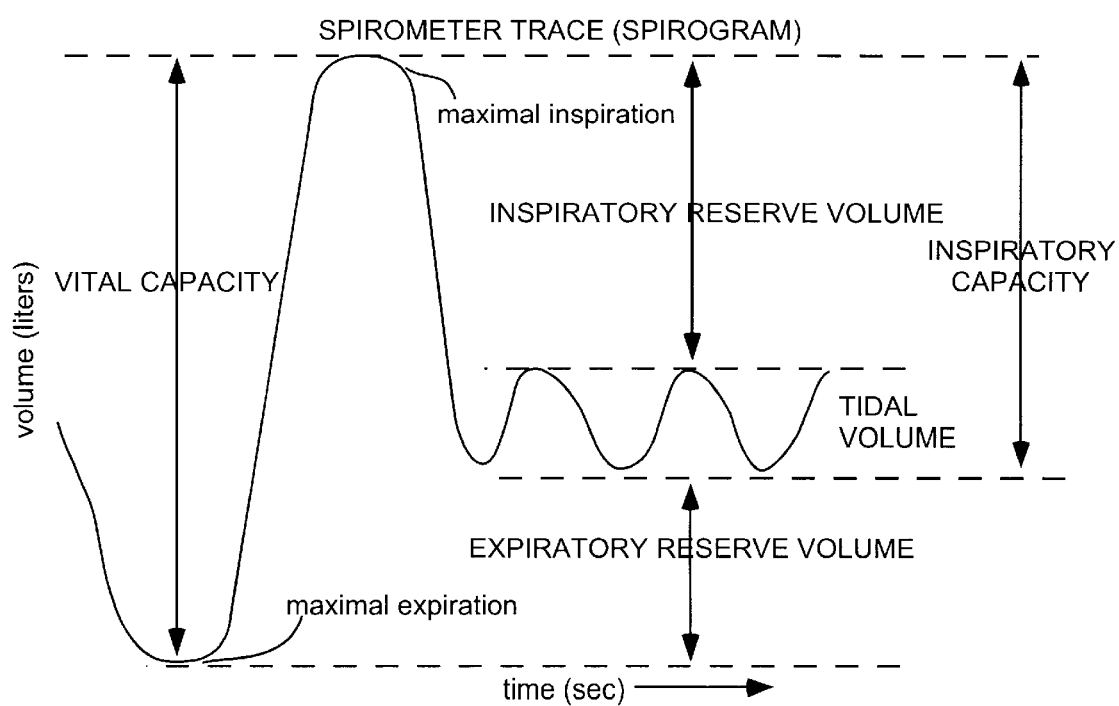
FIG. 56 is a graph showing lung volume over time in the form of a spirogram.

FIG. 56 shows a spirometer trace (spirogram) which illustrates these relationships. As can be seen in the spirograph, the VC 586 is equal to the volumetric difference between maximal inspiration 588 and the maximal expiration 590. The IC 592 is equal to the VC 586 less the ERV 594, that, is the sum of the IRV 596 and the tidal volume 598. The tidal volume 598 is the normal breathing volume as represented by the wave in the spirogram. The IRV 596 is the equal to the volumetric difference between maximum inspiration 588 and the maximum volume defining the tidal volume 598. The ERV 594 is equal to the volumetric difference between the minimum volume defining the tidal volume 598 and the maximal expiration 590.

Figure 18:
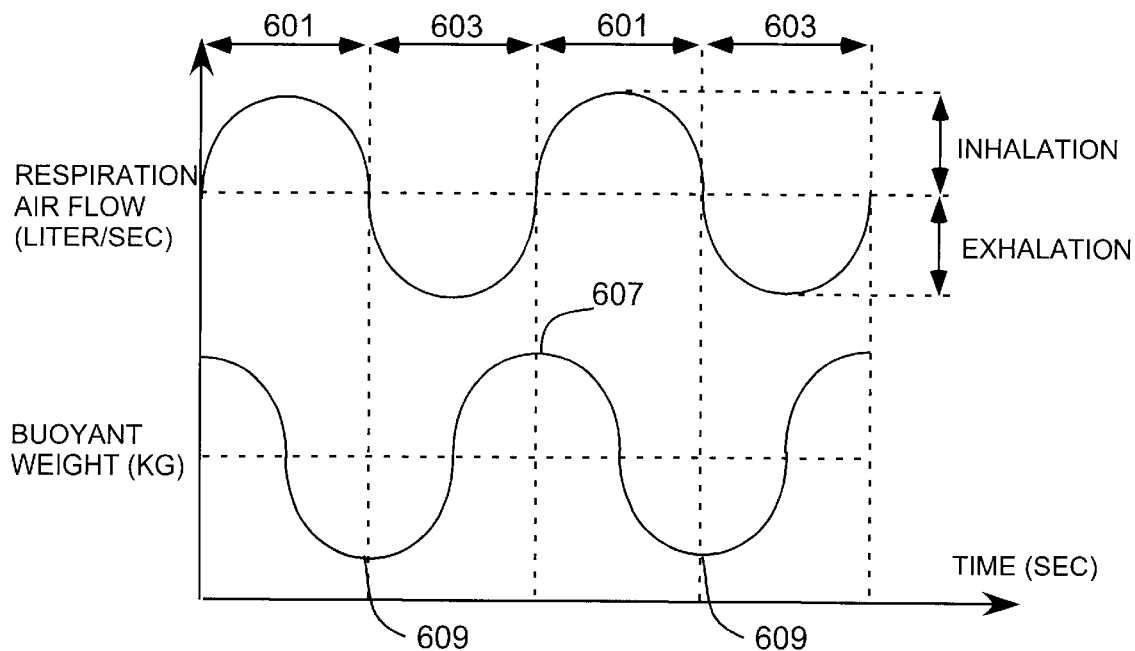
FIG. 18 is a graph showing breath inhalation and exhalation phases and buoyant weight over time.

There are several known methods to detect the breathing phase of a human which can be utilized such as, for example, a mask or mouthpiece pneumotachograph, a non-mask nasal pneumotachograph, a heated thermistor anemometry, and an abdominal or chest respiratory movement detection device (stethograph). A chest strap type breathing sensor such as the "Piezo Respiratory Effort Sensor" model #1460 from Pro-Tech Services can be utilized. A signal from the breath sensor 128 is fed into the controller 116 which processes the respiration data, calculates a desired massaging response, and subsequently drives the manipulators 114. The microprocessor of the controller 116 preferably includes detection, evaluation, and control segments of computer code. As shown in FIG. 18, evaluating breath data for inhale, exhale, or command states consists of monitoring small voltage signals output by the sensor 128 and computationally detecting the peaks (corresponding to maximum inhale of the user) and the valleys (corresponding to the maximum exhale of the user 103) of the more-or-less sinusoidal respiration signal.

Figure 19:
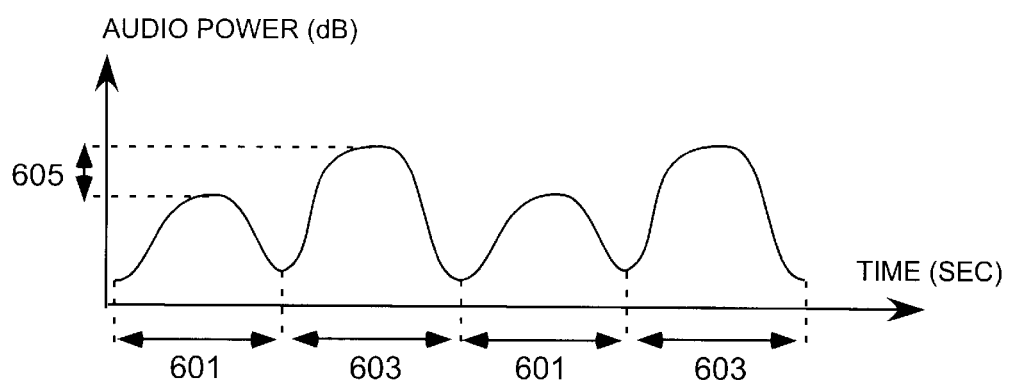
FIG. 19 is a graph showing audio power over time of a respiration cycle.

These detecting methods are somewhat invasive in that they each require the user 103 to wear something over their mouth or nose or to strap bands around their torso. Two alternative means which cause less user irritation: are "Acoustic Detection (Auscultation)" and "Buoyant Density Measurement". Moussavi et al in their paper "Automated Detection of Respiratory Phases by Acoustical Means" (University of Manitoba, Winnipeg, Canada), describe techniques to ascertain the detection of respiratory phases by use of contact accelerometers (EMT25C Siemens) placed at various sites on the user's chest. They found that by measuring the power of the sounds recorded in a bandpass of 150–450 Hz, exhalation sounds are consistently more powerful than inhalation sounds. This allows one to determine when a user is inhaling and when a user is exhaling. Their study found that "the greatest difference in power between respiratory phases is about 10 dB for the best recording site". When contact accelerometers are mounted in a supportive membrane, the user 103 comes into contact with the sensors 128 when reposing on the membrane. The controller 116 processes the signal first to apply a bandpass to the signal in the range of about 150–450 Hz. Then the signal is converted to power content in appropriate time slices. As shown in FIG. 19, the resulting plot shows humps of power alternating from small and large intensity 601, 603 (inhalation and exhalation, respectively). By identifying the differences 605 between neighboring, the controller 116 identifies the inhalation and exhalation respiration phases 601, 603.

Figure 20:
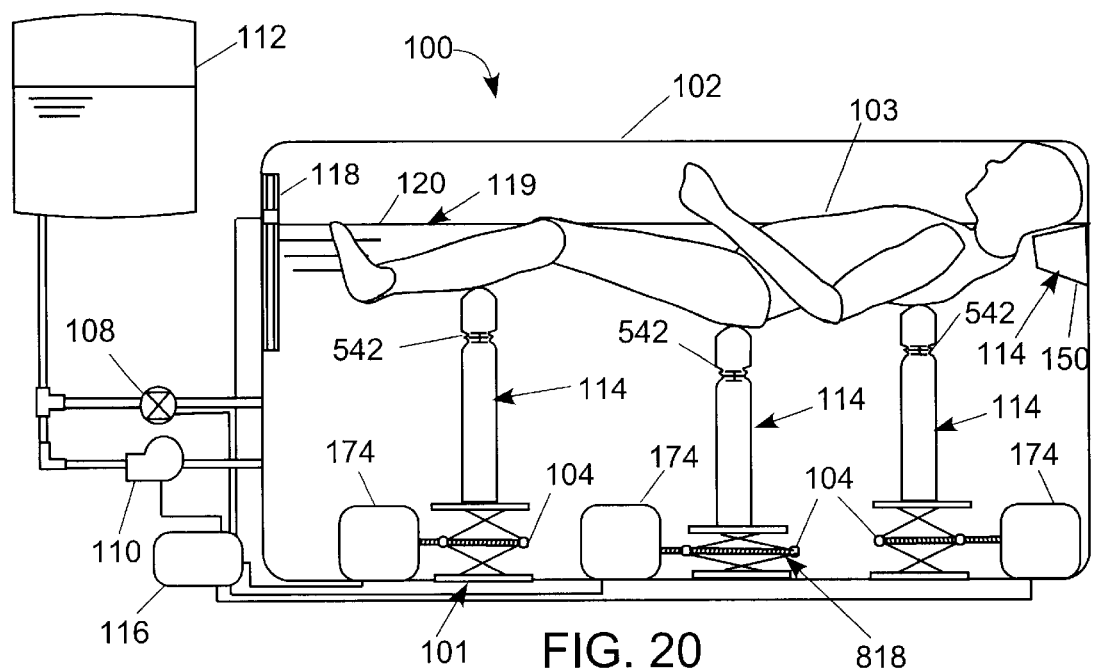
FIG. 20 is an elevational view of a variation of the device of FIG. 3, wherein the device has massage posts with attached force sensors.

As best shown in FIG. 20, another means of detecting the breath phase of the buoyantly supported user 103 is to mount a force sensor 542 or other type of weight sensor on at least one manipulator 114 and note changes in the user's weight. Assuming the lung area of the user's torso is at least partially submerged and the manipulators 114 are supporting at least part of the user's weight, the user 103 exerts more weight on the manipulators 114 when the lungs are deflated and less weight when the lungs are inflated. The average tidal volume of an adult human is 0.5 liters. This results in a tidal displacement of 0.5 liters or 0.5 kg of water. Experiments with a lean 1.8 meter subject immersed to his armpit demonstrate a buoyant weight of 12 kg and a tidal fluctuation in buoyant weight of 0.5 to 1.0 kg. As best shown in FIG. 18, the user's weight varies in a cycle similar to the breath inhalation and exhalation phases 601, 603 with some distortion as the user's posture relative to the working fluid level 120 changes and with a −90 degree phase offset. The user's minimum buoyant weight 609 occurs at the end of the inhalation phase and the user's maximum buoyant weight 607 occurs at the end of the exhalation stage. There may be an additional phase offset due to the viscosity of the working fluid 120. However, the postural and viscosity-based distortions can be accounted for statistically by measuring them for a characteristic population of users.

The manipulation stroke position and/or intensity can be synchronized with the user's respiratory phase 601, 603. For example, the manipulators 114 can apply more intensity during the exhalation phase 603 and less intensity during inhalation phase 601. Alternatively, manipulation intensity may be synchronized with user's respiratory frequency (e.g. slower breathing may trigger more intense manipulation) or tidal volume (e.g. deeper breathing may trigger more intense manipulation). Additionally, the controller 116 is preferably operably connected to an audible signal generator 134 such as, for example, a speaker, so that the controller can provide audible signals or commands to the user which the user can understand as a signal leading the user through breathing, stretching, and/or strengthening exercises. Preferably, the signals or commands are synchronous with the user's breathing. The controller 116, therefore, can act as a coach to lead the user.

Figure 21:
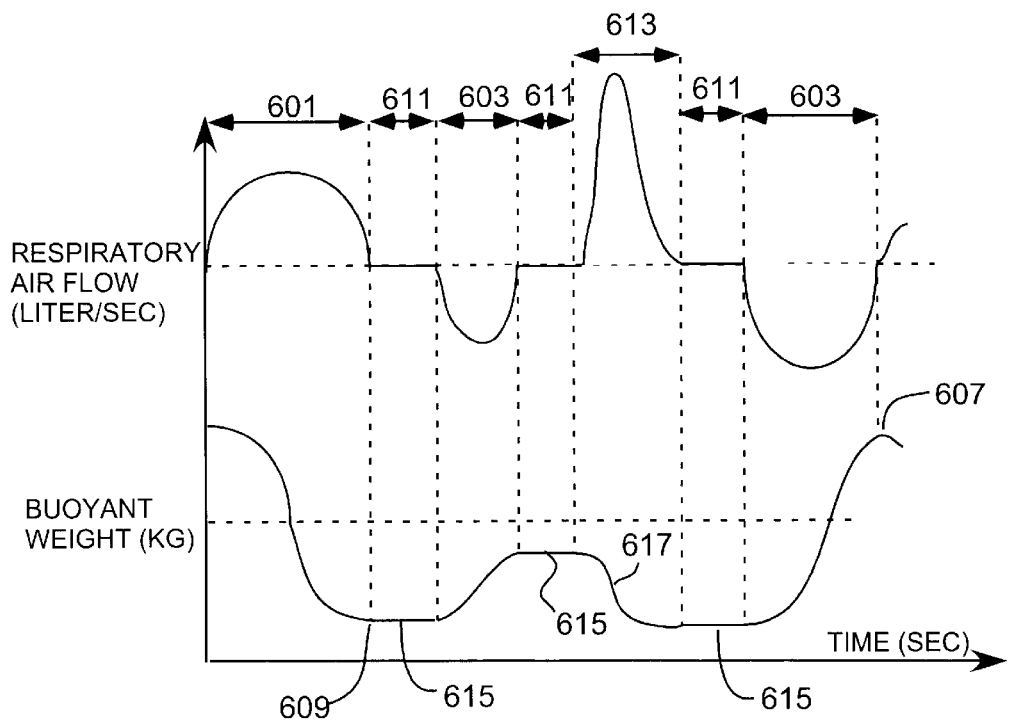
FIG. 21 is a graph showing respiration aberrations and buoyant weight over time.

A deep tissue massage often involves approaching but not reaching or surpassing the pain threshold of the user 103. In order to apply this level of pressure, the manipulation device 100 can utilize a combination of physiological info (e.g. knowing that the neck is more sensitive than the shoulder) and individual preferences. These preferences differ by person, location, type of massage, and current status of the area (e.g. an injury might make an area more sensitive). These preferences could be determined either by asking the user 103 to dial in a desired pressure or by trial-and-error— ramping up the pressure in a given area until the recipient feels pain and then backing off the force by a set or proportional amount. As best shown in FIG. 21, the controller 116 can automatically detect the pain sensation by monitoring the breath and noting aberrations such as the user 103 holding her breath or quickly inhaling. No change in air flow or a plateau 615 in the user's buoyant weight indicates a breath hold 611. A rapid or spiked inhalation or a sharp drop in buoyant weight 617 indicates pain. 613 A knowledge of a particular person's pain thresholds in various locations can help correlate that person's preferences with other users. This means that if the controller 116 knows how much pressure the user 103 likes on the user's back and neck, it is able to classify the user 103 as someone who likes a particular class of massage. This method doesn't require conscious input from the user 103 and is hence preferred to more manual feedback solutions. This preference can be stored for future use so crossing the pain threshold will occur less frequently.

During a massage, it is occasionally necessary for the user 103 to adjust characteristics of the massage such as speed, style, and force of the manipulation. If a human is applying the massage, these adjustments are typically requested verbally. With the manipulation device 100 applying the massage, the user 103 can open his or her eyes to examine the control panel and press the appropriate button or other manual input device. However, the use of speech or eye-hand coordination engages higher-brain functions and makes relaxation difficult. The ability to non-verbally adjust the stroke of a mechanical massaging system allows the user 103 to relax more thoroughly. When a user 103 is able to select various types and styles of massage with breath patterns or volitional breath commands then he or she is able enjoy a more relaxed state for a greater period of time. This is particularly true if the breath patterns are chosen so the breath patterns are intuitive for a given request. For example, the controller 116 may interpret three quick exhales to stop the massage and three quick inhales to change the massage style.

The control system preferably includes the programmable controller 116, a feedback or manual input device 129 for the user 103 or other party to manually provide instructions to the controller 116, and various sensors for providing desired information to the controller 16 regarding conditions of the device 100 and/or the user. The controller 116 is preferably adapted so that user 103 can choose whether the manipulators 114 are moved manually by direction of the input device 129 or automatically by automated control of the controller 116. The input device 129 can include a remote pointer device, such as a joystick, trackball, or spaceball, located on the frame of the tank 102 or other support assembly so that the device 129 can be easily operated by the user 103 or by another party in or near the manipulation device 100. The input device 129 can alternately be located away from the tank 102 for input by another party who may be located some distance from the device. It is noted that the input device 129 can alternately include other devices such as a keyboard, or connection to a computer network such as an intranet or the Internet.

Automatic control by the controller 116 preferably controls positions of the manipulators 114 according to one or more of several methods. The manipulators 114 can following a pre-recorded pattern stored in memory of the controller 116. This pattern can be based on absolute dimensional offsets from an origin (e.g. ten inches above and three inches to the "right" of an origin) or the pattern can be based on relative or proportional offsets (e.g. 10% of body length above and 40% of hip width to the "right" of an origin). Additionally, the manipulators 114 can be moved randomly by the controller 116 within certain constraints. Furthermore, the manipulators 114 can be moved based on the controller 116 interpreting" a music or video stream by converting tempo, pitch, volume, image features, or some combination of these into characteristic massage jet patterns The controller is 116 also preferably adapted for a novel the method of specifying the massage pattern, that is, to specify the location, speed, and intensity of the manipulators 114. The specification and evolution of these massage patterns is a technology which can be described as "evolving preferences". One method of specifying these preferences is to describe the entire manipulation session in detail as a motion profile. This method is used to describe the motion of a milling machine in Computer Aided Manufacture (CAM). Computers are well-suited for quantifiable directives such as these. However, humans are not so good at specifying a complex pattern so rigidly—we are more qualitative. Therefore, the massage patterns can evolve over time as a specific user 103 uses the device 100. The controller 116 can include massage patterns algorithms which evolve the massage patterns based on automated "experiments" and incremental subjective user feedback. Put simply, the controller 116 can try out various massage patterns, receive user feedback—"I liked that or didn't like it"—and use the feedback to adjust or bias long-term preferences for that specific user Preferably, the controller 116 is pre-programmed with a number of basic patterns such as linear stroking, circles, and pulsing. When a new user 103 begins a session, the controller 116 "calibrates" itself by explicitly identifying a number of key locations such as around the shoulder blades and the erector spinae muscle group and explicitly ask a few questions so the user 103 receives a decent massage before "evolving". Upon entering the device 100, the user 103 might identify herself and select either a relaxation or invigoration mode. The controller 116 would then follow a massage pattern whose basic patterns rely on a set of user-specific variables. In its simplest mode of operation, a single value would represent each of these parameters and the massage pattern would follow them strictly—"central value" adaptation method. These variables describe the user's preferences: manipulator pressure, knead speed, knead direction (up or down), duration of focus on each body area, and a host of other such parameters. Initially, these variables are set to defaults but after subsequent uses, the controller 116 adapts the massage pattern to the specific user 103 by reacting to feedback of prior massages. For example, during the massage the controller 116 can verbally ask if the manipulator intensity should increase, decrease, or remain the same and prompt the user 103 to respond using the feedback devices 129, respectively. If the user 103 specifies that the manipulator 114 intensity should be increased, the central value for this parameter would be biased upwards by either a set amount or by an amount inversely proportional to the number of interactions with this particular user 103 (preferably the controller 116 learns more quickly with new user 103).

Alternatively, the parameters of the massage pattern can be described with probability distributions defined by a central value and a measure of allowable deviation. Manipulator pressure, for example, can randomly vary around the central value within tolerances defined by the deviation limits. This "probability distribution" adaptation method is robust insofar is it only infrequently produces an unacceptable outcome but it requires significant understanding of which variables influence the massage quality. The advantage of probability distribution over the central value method is that the extra variability makes the device 100 seem less mechanical and hence more enjoyable.

To produce even more massage pattern variation, the controller 116 can employ a "genetic algorithm" (GA) approach using evolutionary techniques—reproduction, crossover, and mutation. GA is well-understood in the field of machine learning and requires little understanding of what factors make some massages better than others. However, because it is evolutionary, it is prone to producing "monsters" (unacceptable massage patterns) when trained with small data sets. Unfortunately, large data sets require either long training periods and/or pooling results from many similar therapy devices, perhaps via Internet connectivity.

The subtleties of the feedback mechanism are preferably established as the controller 116 is trained. Each user 103 develops a personal vocabulary with which to communicate with the manipulation device 100 that would be different from other users' vocabularies. This may be accomplished by providing means for the device to verbally ask the user 103 to do whatever feedback pattern the user wants to represent, for example, "reduce massage intensity". This pattern would then trigger a control routine which reduces the manipulation intensity. Neural nets can be utilized for this sort of learning behaviour or some other trainable system. Each user 103 is automatically recognised upon entry into the device 100 by a user recognition device 130 which can be some combination of body shape (or shape of a portion of the body), hand shape, fingerprint, voice recognition, unique way in which the user 103 manipulates the feedback mechanisms, or a manual selection mechanism such as pressing button(s). Upon recognition of the user 103, the controller 116 loads the evolved massage pattern established for that particular user 103 and proceeds.

The controller 116 and control system is preferably upgradeable either with additional manipulators, sensors (feedback mechanisms, position encoders, microphones, cameras, temperature or pressure sensors), or computing power (processor speed, memory, software upgrades) while retaining the education it has acquired. With an initial revision of the hardware and proper training, it is capable of attaining a certain level of manipulation ability. At that point, it is no longer capable of advancing because it's computational unit lacks the complexity required. It is possible at that point to increase the controller's complexity while retaining the training the controller 116 has developed.

The controller 116 is preferably removable from the manipulation device 100 for connection to a personal computer for occasional connectivity or could be permanently connected either to a local network (such as an intranet) or a global public network (such as the Internet). These connections may be wired or wireless. The preferred method for connectivity is to incorporate a cellular packet transceiver into the controller 116 which enables bi-directional data exchange without requiring a telephone socket or wired connection. Any of these connectivity options allow the controller 116 to obtain software upgrades and exchange massage programs with other users. Another desirable feature is for a particular user's preferences to be "portable", that is, to be able to use the same evolved training and vocabulary for multiple manipulation devices 100, perhaps at geographically distant sites. This is accomplished either by transferring this information via a computer network or by storing them on removable media such as, for example, flash memory.

Preferably, the control system includes a remote feedback device 131. If a remote operator is controlling the manipulation device 100, he or she typically requires feedback from the user 103 being manipulated. This feedback might take the form of audio, video, and/or tactile signals. For example, a camera and microphone might be pointed on the user 103 and this audio-visual signal transmitted to the operator. In addition, signals from the user 103 input device 129 (joysticks, spaceballs, etc.) is fed back to the remote operator and converted to audio, visual, and/or tactile feedback. Biofeedback can be transmitted to inform the operator of the user's excitement, pleasure, or pain sensations.

Preferably, lights 132 are provided which guide the user 103. When user approaches the manipulation device 100, the lights preferably make steps and/or handrails illuminate. Once the user 103 is present, the feedback or input device 129 illuminates so that the input device 129 may more easily be grasped and the more relevant buttons and switches are more brightly illuminated than others, cueing the user 103 to interact with the control panel in certain ways. Once the user 103 is fully situated, the lights 132 can pulse along with music and/or manipulation intensity.

Figure 22:
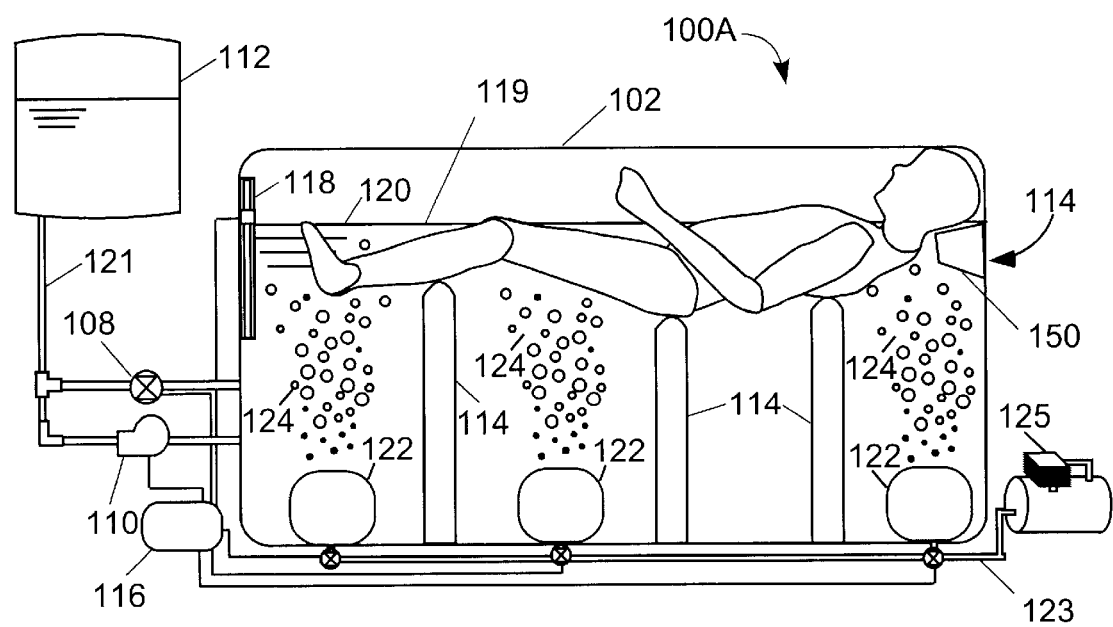
FIG. 22 is an elevational view of variation of the device of FIG. 3 wherein bubbles are generated to change the density of the working fluid.

As best shown in FIG. 22, a device 100A according to a variation of the device 100 of FIG. 3 utilizes another method of changing the user's buoyancy or assisting to change the user's buoyancy is to change the density of the working fluid 119. This may be accomplished by diffusing a gas such as, for example, air into the working fluid 119, to form rising bubbles 124, essentially leavening the working fluid 119. Thus, the means for changing the pressure intensity of the manipulators 114 can comprise components which change the density of the working fluid 119. The illustrated embodiment includes a plurality of diffusers 122 such as, for example, air stones and a compressor 125 for supplying pressurized air to the diffusers 122 via conduits 123. By making the bubbles 124 small, the bubbles 124 remain suspended in the working fluid 119 for a longer period of time. Larger bubbles 124 stimulate the skin of the user 103 more as they rise to the surface of the working fluid 119. A suitable diffuser 122 is the DAD6 ceramic oxygen diffuser available from Dryden Aqua Co. in Edinburgh, Scotland. This diffuser 122 has a pore size of 0.3 um, causing the gas to go more easily into solution.

It is noted that a combination of vertically moving the manipulators 114, changing the working fluid level 120, and/or diffusing gas into the working fluid 119 can be implemented. For example, FIG. 3 shows a device 100 where the manipulators 114 may be vertically moved and/or the working fluid level 120 may be raised or lowered and FIG. 22 shows a device 100A where the working fluid level 120 may be raised or lowered and/or gas may be diffused into the working fluid 119.

Figure 23:
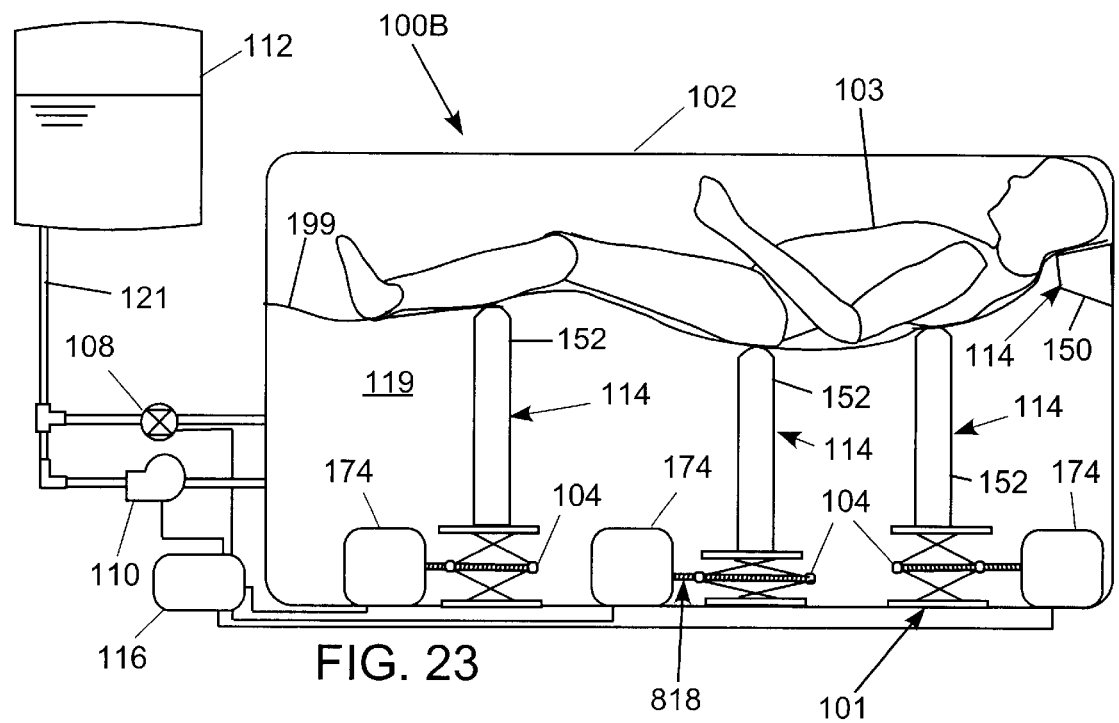
FIG. 23 is an elevational view of a variation of the device of FIG. 3 wherein a membrane is located between the user and the manipulators.

FIG. 23 illustrates a manipulation device 100B according to another variation of the device of FIG. 3. The device 100B utilizes a membrane 199 through which the manipulators 11 engage the user 103 rather than the manipulators 114 directly contacting the user 103. The illustrated membrane 199 covers the entire aperture of the massage tank 102 but the membrane 199 may support only part of the user 103 allowing a mix of manipulation contact styles to be utilized. For example, the head support 150 may be an area covered by the membrane 199 while the remainder of an aperture exposing the working fluid 119 is uncovered. Thus, the device 100B allows working fluid 119 on both sides of the membrane 199 and the user 103 becomes wet. The membrane 199 can be permeable or impermeable to the working fluid 119. When the membrane 199 is permeable, the working fluid 119 is on both sides of the membrane 199 regardless of whether the membrane 199 completely closes the aperture or not. When the membrane 199 is impermeable, covers the entire aperture, and is sealed along the aperture perimeter, the user 103 may remain dry even while lifted or lowered into the buoyancy working liquid 119. For this reason, the word "submerged" as used in this specification and claims shall mean "causing to displace working fluid 119 and generating a buoyant force" without requiring the user to be fully under the working fluid 119 or to have direct contact with the working fluid 119. The membrane 199 may be provided with lifting/lowering means controlled by the controller 116 so that the membrane 199 can rise under automatic control between a partially or fully submerged position to a partially or completely above the working fluid position. Located in the above the working fluid position, the membrane 199 becomes a safety and thermal insulating layer when the device 100B is not in use. The membrane 199 is preferably removable attached so that the membrane 199 may be installed and removed by the user 103 to allow flexibility in the character of the massage while also providing a safety and thermal barrier.

Figure 24:
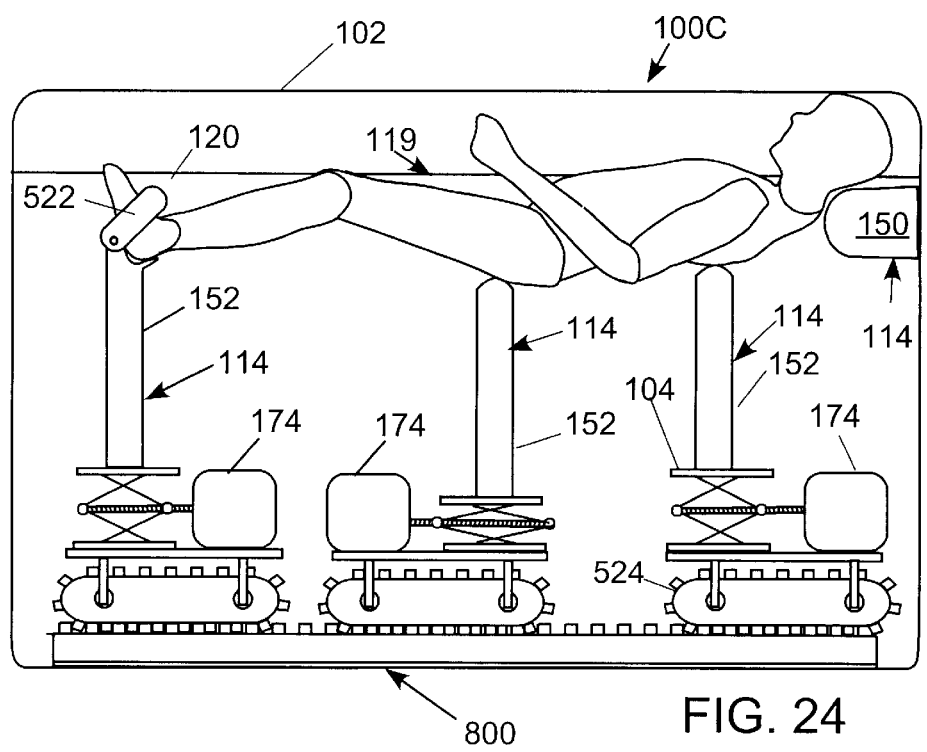
FIG. 24 is an elevational view of a variation of the device of FIG. 3, wherein the device has a foot stirrups which retain legs in position.

FIG. 24 illustrates a manipulation device 100C according to another variation of the device 100 of FIG. 3. The device 100C includes means for maintaining the user's limbs in appropriate positions such as hand and/or feet into receptacles 522 which prevent the limbs from "falling off" the manipulators 114. Foot receptacles 522 are ideally actuated to move in the X-axis towards the user's head to aid entry into and egress from the device 100C. The foot receptacles 522 then move in the X-axis away from the user's head, stretching out the user 103. The receptacles 522 can be part of the therapy by using the receptacles 522 to adjust the user's posture.

Figure 25:
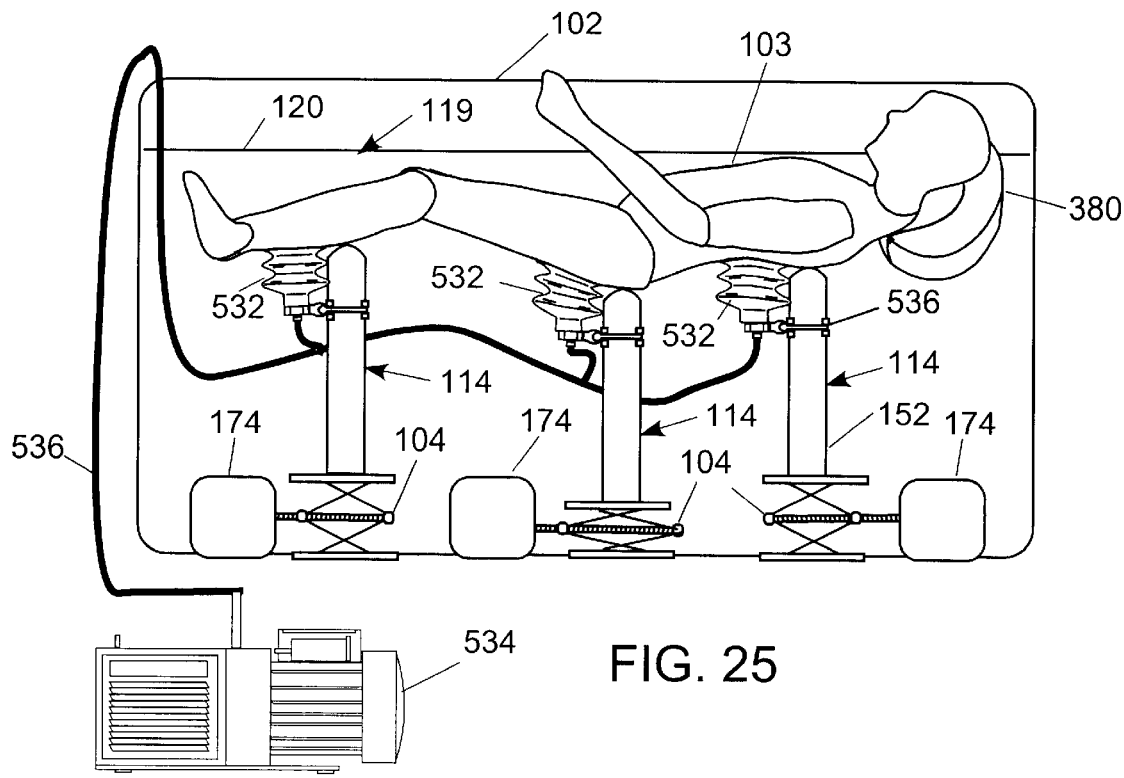
FIG. 25 is an elevational view of a variation of the device of FIG. 3 having a suction restraint system.
Figure 26:
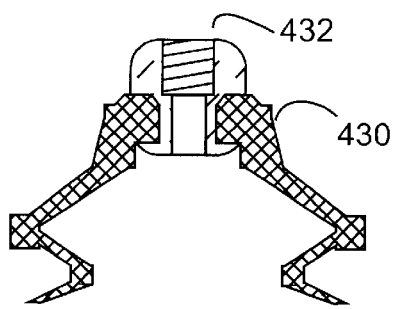
FIG. 26 is a cross-sectional view of suction restraint in the form of a vacuum cup which can be utilized with each of the embodiments of the present invention.

Foot stirrups, seat belts, and other "clamping systems" achieve the goal of holding the user 103 in place so that manipulation can be applied to a known part of the user 103. However, these clamping systems require user interaction and limit freedom of movement and interaction, reducing the desirability of a therapy device. As shown in FIGS. 25 and 26, suction can be used to hold the user 103 in place without a clamping frame. One means of applying such suction is by use of vacuum cups 532 which use gentle suction to hold the user 103 in place, counteracting the force of the manipulation. Vacuum cups 532 differ from standard suction cups in that they are connected to a suction source such as a vacuum pump 534 so the vacuum cups 532 actively attach to surfaces instead of requiring pressure to mate the two surfaces. In addition, vacuum continually withdraws the working fluid 119 which leaks between the vacuum cup 532 and the membrane or user 103. This is important because it's very hard to seal a standard suction cup against human skin due to the flexibility and variability of the underlying flesh. The illustrated vacuum cups 532 include a flexible cup 430 provided with a vacuum hose fitting 432 for connecting the vacuum pump 534 via a vacuum hose.

Most skin areas on the user 103 comfortably withstands about 2 psi of negative pressure. When 25 pounds of positive pressure in the form of manipulator intensity to a fully buoyant user 103, suction must apply a matching restraining force. With about 2 psi of negative pressure, about 12.5 square inches are needed (a 3.5"-by-3.5" area). With a larger area (i.e. the entire back area of a chair) less negative pressure can be used which provides additional comfort. To maximize comfort, the magnitude of suction may be controlled to be proportional to the degree of positive force applied. This feedback signal may be obtained by: (a) coordinating with the massage program controller 116 (e.g. when a powerful massage manipulator engages, the suction force increases); (b) measuring pressure in vacuum cups; (c) measuring flow rate through vacuum lines such that when more leakage occurs the suction pressure is increased; and (d) measuring displacement of the user 103.

Suction restraints 532 may be particularly important when used in conjunction with breath-synchronized submergence. In this case, the suction restrains 532 can pull the user 103 under water in phase with the user's exhalation. Since the user 103 is buoyant, without the ability to actively pull the user 103 under water, they may instead just float. The use of a clamping frame to pull the user 103 under the working fluid 119 is more likely to induce fear in a user 103 as it has a greater risk of drowning the user 103 in case of malfunction. The suction restraint 532, on the other hand, can be designed to generate suction pressures insufficient to hold the user 103 under the working fluid 119 if the user 103 pushes away from the restraint.

Suction may also be applied as a therapeutic modality in its own right. Chinese acupuncturists recognize the application of suction to specific locations on the body (Ba Guan) to promote, maintain, restore or improve health, to prevent a disorder, imbalance or disease or to alleviate pain. The same vacuum cups 532 described above may be applied automatically using the same mechanisms. Dragging a vacuum cup 532 over the user's body may deform the cup 532 and prevent it from sticking to the user. Using the drop-catch method described hereinabove, the cups 532 may be made to move over the user's body without contact. Buoyancy may be used to control the supportive force exerted by the vacuum cup 532.

It has been found that periodic submergence of the user 103 ("dunkee") by another human ("dunker") can induce a state of relaxation in the dunkee. It is thought that this relaxation derives from the sense that the dunker is sensitively attuned to the dunkee's respiratory cycle. A human-administered breath-synchronized submergence therapy called "Waterdance" has been developed at Harbin Hot Springs in Middletown, Calif. With an interest in achieving a similar relaxation and trust in the sensitivity of a machine, the controller 116 can be adapted to cause the mouth and nose part of the user 103 to at least occasionally be submerged in the working fluid 119 in synchrony with the user's exhalation. In order to prevent working fluid 119 from entering the user's nose, the user can be provided with a nose clip or mask which covers at least the nose. Synchronizing submersal with the user's exhalation requires a sensor capable of respiratory phase detection, preferably in a non-intrusive fashion. A mask which covers the user's nose and mouth or only the user's nose can be fitted with a pneumotachograph which would simultaneously prevent water from entering the nose and detect the exhalation of air. The mask may be fitted with a check valve to allow air to enter when above water and the user inhales but prevents water from entering when submerged. The submergence can be independent or in addition to water buoyancy manipulation. Preferably, some or all manipulators 114 are capable of applying static suction pressure to the user 103 in order to actively pull the user into the working fluid 119 more quickly and/or more deeply than the user 103 would move without such pulling. Suction is also good to maintain the user's position and prevent them from falling off the manipulators 114.

Figure 27:
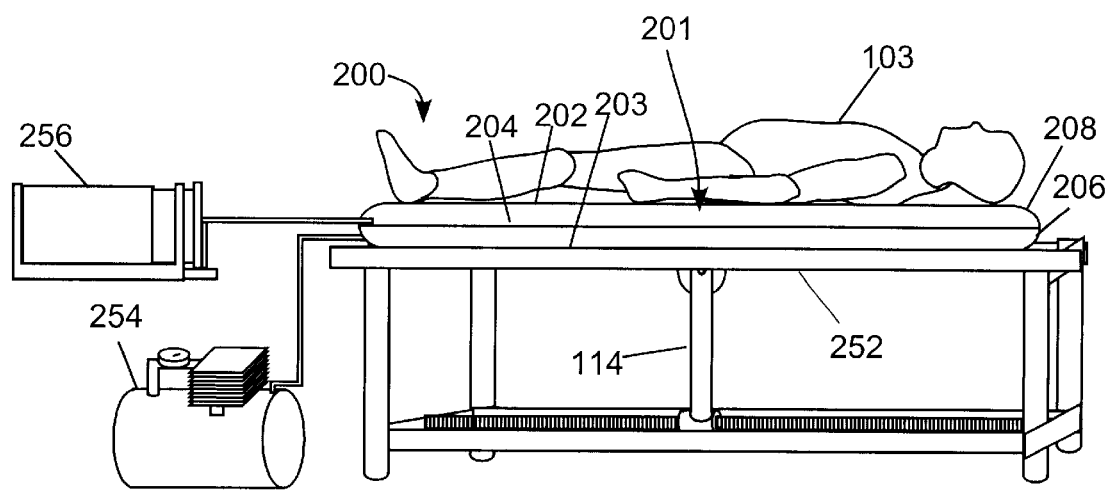
FIG. 27 is an elevational view of a manipulation device according to a second embodiment of the present invention having an open frame bed that supports a water mattress upon an air mattress, pressurizing devices for respective fluids, and a massage roller which acts upon the bottom surface of the lower mattress.
Figure 28:
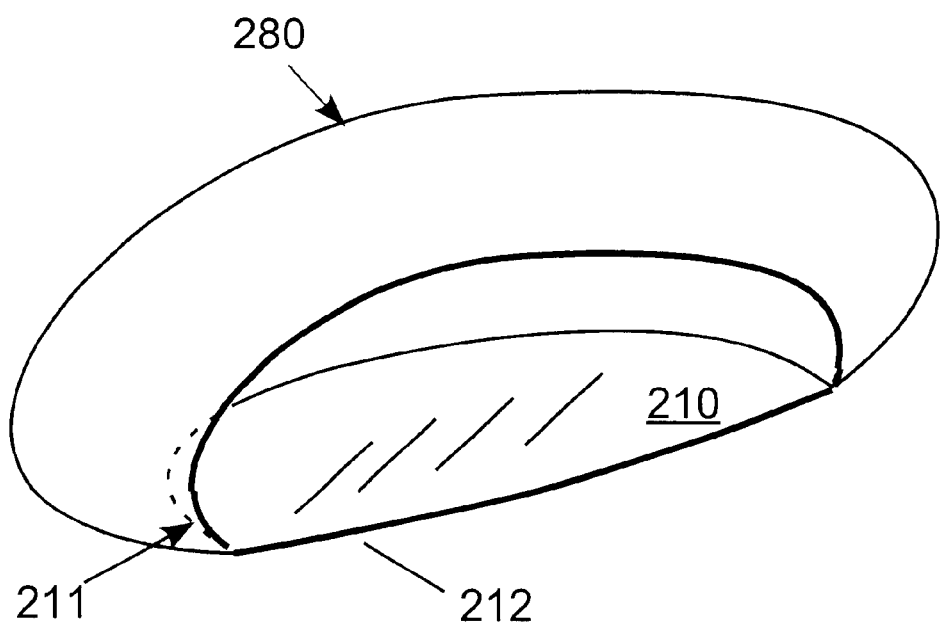
FIG. 28 is a perspective cutaway view of one of the mattresses of FIG. 27 wherein the mattress is unrestrained.

FIG. 27 illustrates a manipulation device 200 having dynamic intensity control according to a second embodiment of the present invention. The illustrated device 200 includes at least one manipulator 114 adapted to engage the user 103 through a membrane 201; a translator for moving the manipulator 114 along at least one axis to apply a manipulation to the user 103; and means for changing a pressure intensity of the manipulator 114 while providing spatially uniform support to the user 103 outside a contact patch of the manipulator 114 to selectively vary the pressure intensity at which the manipulator 114 engages the user 103. The illustrated membrane 201 is a three layer membrane having upper, lower, and intermediate layers 202, 203, 204 with the perimeters of the layers 202, 203, 204 sealed to each other to encapsulate two discrete volumes, a lower volume 206 and an upper volume 208. It is noted that the membrane 201 may alternatively have one or more layers. When more than one layer is used, such as the illustrated embodiment, space between each layer 202, 203, 204 is preferably filled with a pressurized or unpressurized working fluid. The lower volume 206 is preferably filled with a working fluid such as, for example, a gas like air which is pressurized. A suitable operating pressure for the gas is about 0.2 psi. The pressure of the gas in the lower volume 206 is preferably adjusted by a compressor 254 controlled by the controller 116. The upper volume 208 is preferably filled with a working fluid such as, for example, a liquid like water which is pressurized. A suitable operating pressure for the liquid is about 0.2 psi. The pressure of the liquid in the lower volume 208 is preferably adjusted by a hydraulic cylinder 256 controlled by the controller 116. It will be apparent to those skilled in the art that other particular combinations of working fluids and pressures can be utilized and that a multiple volume membrane results in a better feel than a single-volume membrane. The manipulator 114 is located below the lower layer 203 and the user 103 is located above the upper layer 202 so that the manipulator engages the user 103 through the membrane 201. The controller 116 automatically adjusts the operating pressures in the membrane 201, such as in the illustrated upper and lower volumes 206, 208, to dynamically change the pressure intensity of the manipulator 114 while providing spatially uniform support to the user 103 outside a contact patch of the manipulator 114.

Figure 29:
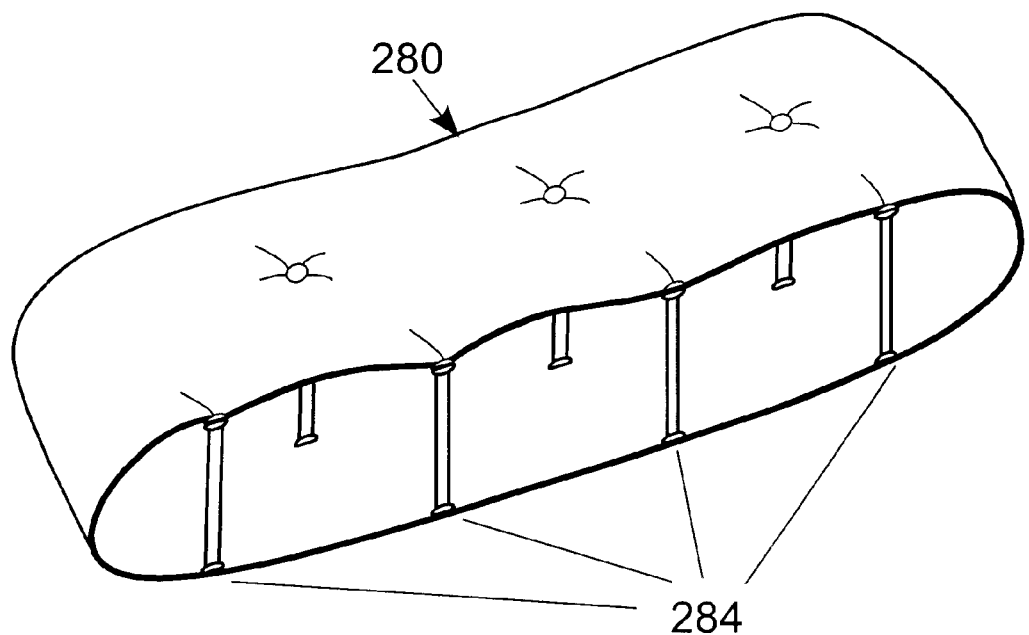
FIG. 29 is a perspective cutaway view similar to FIG. 28 but wherein the mattress is restrained with webbing.
Figure 30:
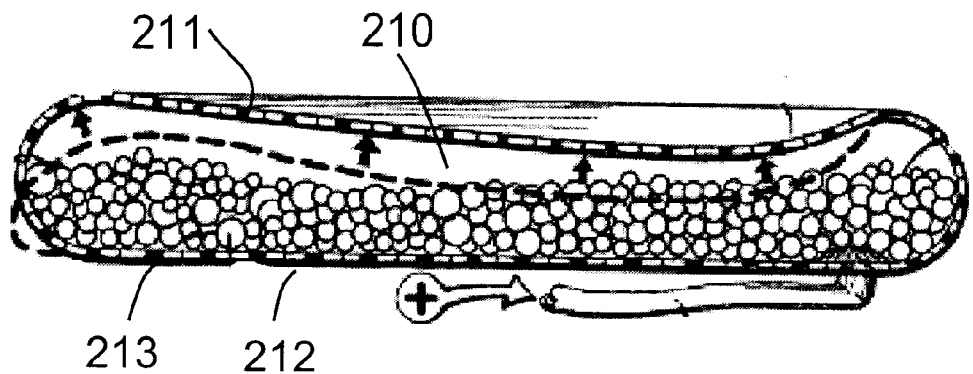
FIGS. 30 to 32 are elevational views, in cross-section, showing a prior art mattress which can be utilized with the present invention wherein the mattress is restrained with support fill.

FIG. 13 illustrates a membrane 201 in the form of an unrestrained air pad 280 having a single volume 210 formed by upper and lower layers 211, 212. When this encapsulated volume 210 is pressurized with a gas such as air, the pad 280 forms a spheroid constrained only by the elasticity and shape of the membrane layers 211, 212. When unloaded (user not present), the upper layer 211 bows upward. This may be acceptable for some applications but in other applications it is desirable for the upper layer 211 to remain approximately flat when unloaded. In those applications a restraint system may be used to prevent the layers from moving apart (delaminating) more than a predetermined distance. The delamination restraint may consist of open-celled foam laminated between the layers 211, 212 as used in ThermaRest camping pads made by Cascade Designs Inc. FIG. 29 illustrates that alternatively the layers 211, 212 may be fastened together by a plurality of restraints or webs 284. These webs 284 are used in Aerobeds made by Aero Products International Inc. The use of an intermediate or internal layer or layers may avoid enclosing any new volumes by not enclosing pockets such as columns connecting the top and bottom layers or by making the internal layers perforated or porous to allow pressurized fluid to equalize with the rest of the volume.

The delamination restraint can also be in the form of firm foam such that when the volume is maintained at atmospheric pressure or unsealed, manipulation pressure will be slight. In order to increase manipulation pressure, a suction (partial vacuum) could be applied to the volume to compress the foam and reduce the inter-membrane distance.

Figure 31:
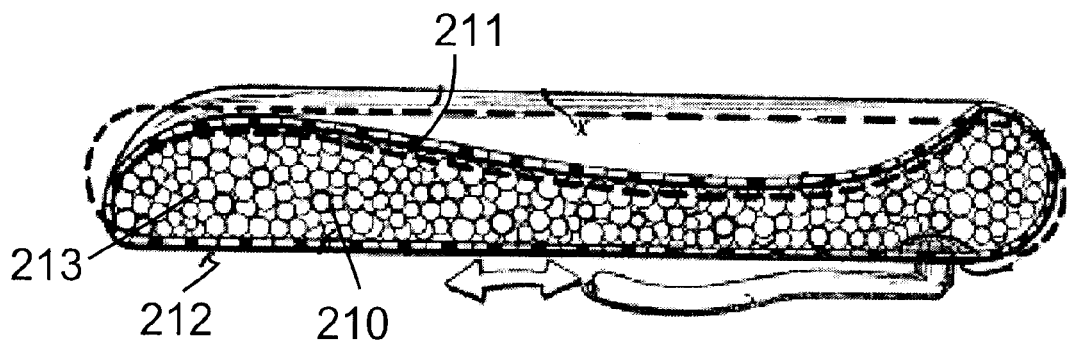
Figure 32:
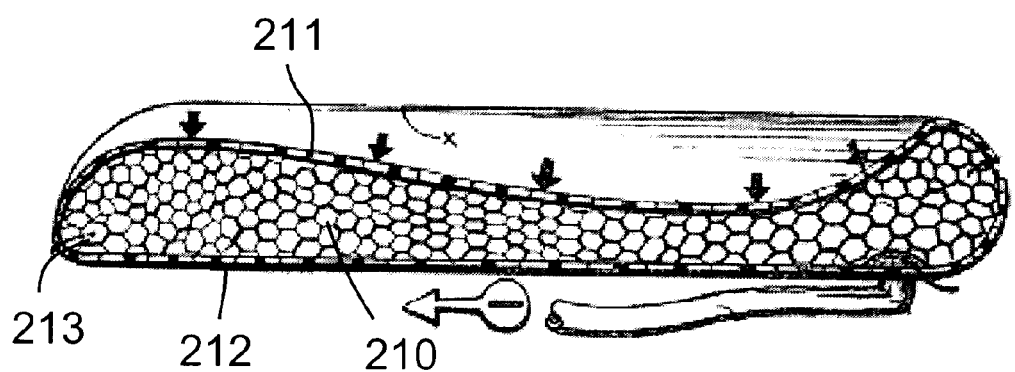

As shown in FIGS. 31 to 32, the delamination restraint can be in the form of a supportive fill material 213 such as, for example, loose beads placed in the encapsulated volume 210. U.S. Pat. No. 4,114,214, the disclosure of which is expressly incorporated herein in its entirety, describes such a system. When the volume 210 is pressurized, the upper layer 211 rides above the fill material 213 in a "floatative" manner. When the volume 210 is "neutrally" pressurized, the upper layer 211 rides on the fill material 213 without compressing it. In this case, the fill material 213 shifts under load to fill the volume 210 without supporting the load. When the volume 210 is insufficiently pressurized or left unsealed, the fill material 213 shifts and compresses to the load's "contour" and supports the load.

Figure 33:
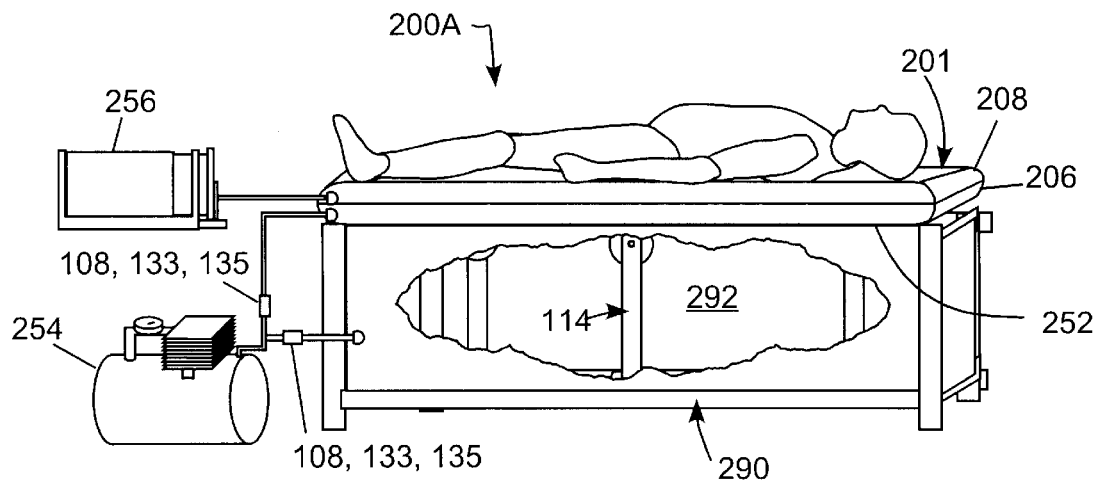
FIG. 33 is an elevational view of a variation of the device of FIG. 27, wherein the device has a pressurized enclosure for the manipulator and the massage manipulator acts through the air mattress and the water mattress.
Figure 34:
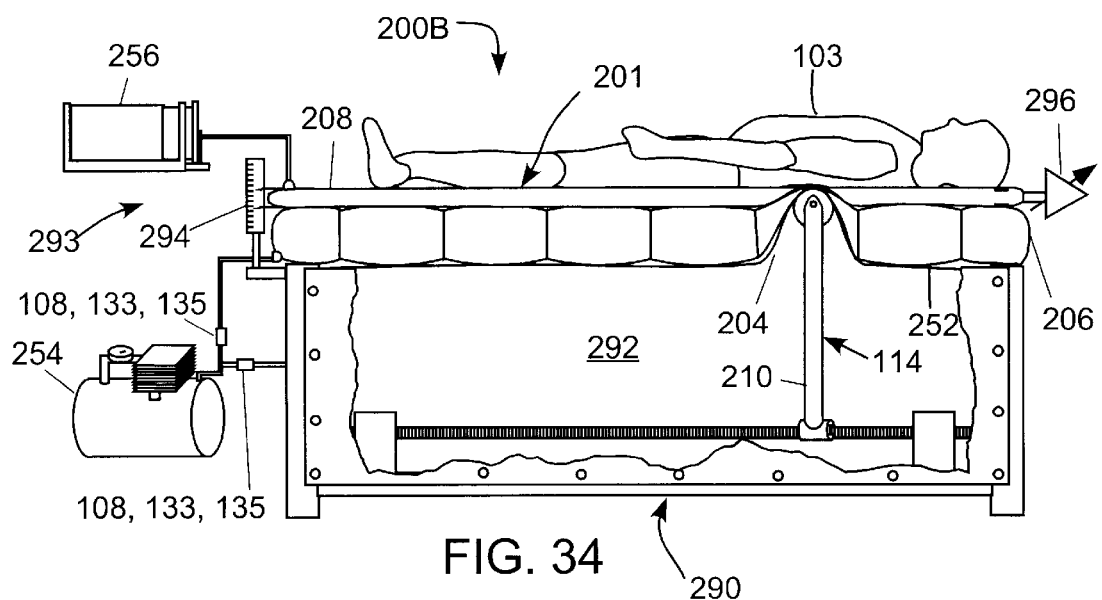
FIG. 34 is an elevation view of a variation of the device of FIG. 33 wherein a capacitance distance sensor and calibrator are attached to the water mattress.

FIGS. 33 and 34 illustrate manipulation devices 200A and 200B according to variations of the device of FIG. 27. The manipulator 114 is encapsulated in a pressurized enclosure 290. The illustrated enclosure 290 is a bed formed by a box having a rigid, closed bottom and sides and an open top 252 forming a massage aperture through which the manipulator 114 engages the user 103 through the membrane 201. The open top 252 is covered and sealed around the perimeter with the membrane 201 which is impermeable to a working fluid located within the enclosure 290 to form a sealed volume. This volume is the "manipulator volume" 292.

Preferably, the manipulator volume 292 is filled with a pressurized gas such as air, the membrane lower volume 206 is filled with a gas such as air at a pressure lower than the manipulator volume 292, and the membrane upper volume 208 is filled with pressurized liquid such as water without restraints. The manipulator volume 292 uses few or no restraints to allow unimpeded freedom of movement for the manipulator 114. The membrane lower volume 206 softens the feel of the supportive surface of the membrane upper volume 208 and may require restraints to avoid bulging. The membrane upper volume 208 provides the buoyancy effect and its weight acts down on the manipulator volume 292 to prevent the bowing-upwards effect when the user is not present. Because liquid such as water is dense and seeks out a low elevation, the upper layer 211 will preferentially bow downwards. The pressures of the manipulator volume 292 and upper volume 208 may be matched to maintain both as approximately flat sheets. The upper volume 208 may be unpressurized, that is at atmospheric pressure, in some configurations.

As shown in FIG. 34, a position-detecting system 293 comprising a calibration sensor 294 and/or a capacitance distance sensor 296 may be used to determine the elevation or relative distances between the membrane layers 202, 203, 204. For example, a conductive film may be applied to the upper and intermediate layers 202, 204 (or parts thereof) and wired to a capacitive measurement circuit having the capacitance distance sensor 296. By measuring capacitance through a known dielectric such as water or air, the distance between the layers 202, 204 may be determined. The controller 116 may make adjustments to the pressures in either the manipulator volume 292 and/or the membrane upper volume 208 to maintain flatness as the user 103 loads the device or the manipulator 114 pushes into the membrane layers 202, 203, 204. It is noted that alternatively the volume pressures may be calibrated and applied "open-loop", that is, without position feedback (as shown in FIG. 33). The controller 116 may control the fluid valve 108 using a feedback loop based on measurements from the pressure sensor 135 and/or the fluid flow sensor 133.

The dielectric constant may vary due to the use of water with varying mineral content or the addition of water purification chemicals. If the dielectric constant of the fluid varies in time or space with a magnitude of uncertainly too great to maintain flatness adequately, the dielectric constant may be accurately and dynamically determined by an associated device which measures the capacitance of the fluid with a fixed displacement.

Figure 35:
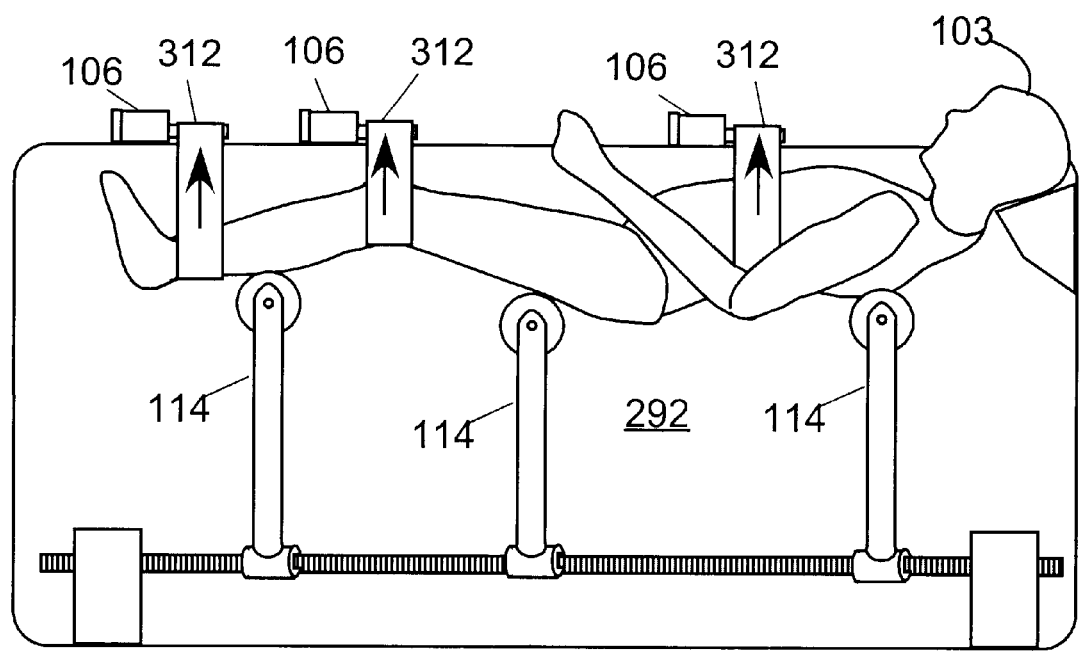
FIG. 35 is an elevational side view of a variation of the device of FIG. 27 having tensioned membranes supporting a user above manipulators.
Figure 36:
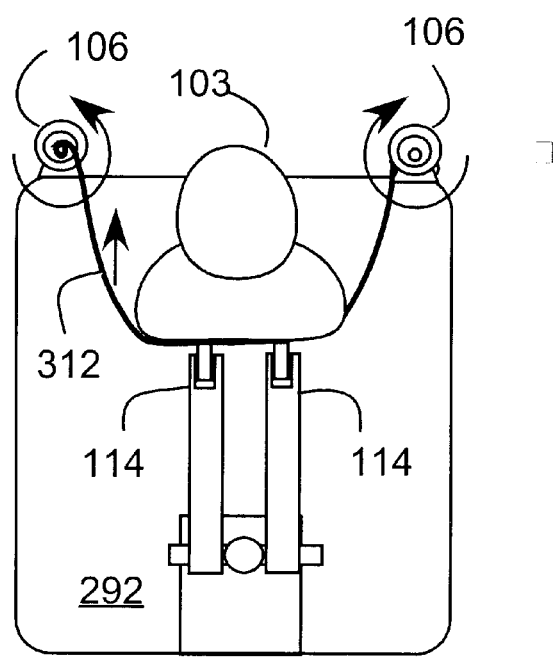
FIG. 36 is an elevational end view of the manipulation device of FIG. 35.

FIGS. 35 and 36 illustrate a single membrane or multiple discrete membrane segments 312 may be used without pressurizing the manipulator volume 292. Tension and/or height adjustments applied to the perimeter of the membrane segments 312 vary the support the user receives from the membrane segments 312 and hence the intensity of the manipulator 114. These adjustments may be made to vary across the length of the surface so more support is provided to the user 103 in some areas and less in others. Note that increasing the tension on a given membrane segment 312 will lift and flatten the membrane segment 312, causing more support to be applied by the membrane segment 312 and less by the manipulator 114. In contrast, adjusting the height of the membrane segment 312 will lift but will not flatten the membrane segment. A suitable tensioning mechanism can include motorized rollers 106 on opposite sides of the membrane segments 312. In the illustrated embodiment, one pair of the rollers 106 tensions the membrane segment 312 supporting the user 103 below the knees, another pair of the rollers 106 tensions the membrane segment 312 between the knees and the lumbar, and another pair of the rollers 106 tensions the membrane segment 312 between the lumbar and the neck. The rollers 106 can be configured to pull symmetrically so the user 103 does not get pulled to one side as the membranes 312 are tensioned. Alternatively, the rollers 106 are configured in a push-pull configuration where the roller 106 on one side of the user 103 releases the membrane segment 312 while the roller 106 on the other side of the user 103 takes up this slack. The rollers 106 then exchange functions causing the user 103 to shake from side to side. This side-to-side motion can relax the user 103 while the manipulators 114 preferably remain static or move sympathetically.

By varying the height of membrane segments 312 along the perimeter, the user 103 may be repositioned into different postures. The membrane 312 would be stretched and contorted by adjusting the X-axis, the Y-axis, and the Z-axis positions of the membrane supports. These postures can help relax certain muscles, helping the efficacy of manipulator massage. For example, if the user 103 lays on her back atop the membrane 312, actuators can lift the perimeter membrane supports at the sides of her calves, knees, and thighs in such a way as to flex the hip and knee joints. This relaxes the user's back muscles, permitting a deeper, more therapeutic manipulation of these back muscles. These motions may be accomplished with pairs of height adjustable rollers 106.

Figure 37:
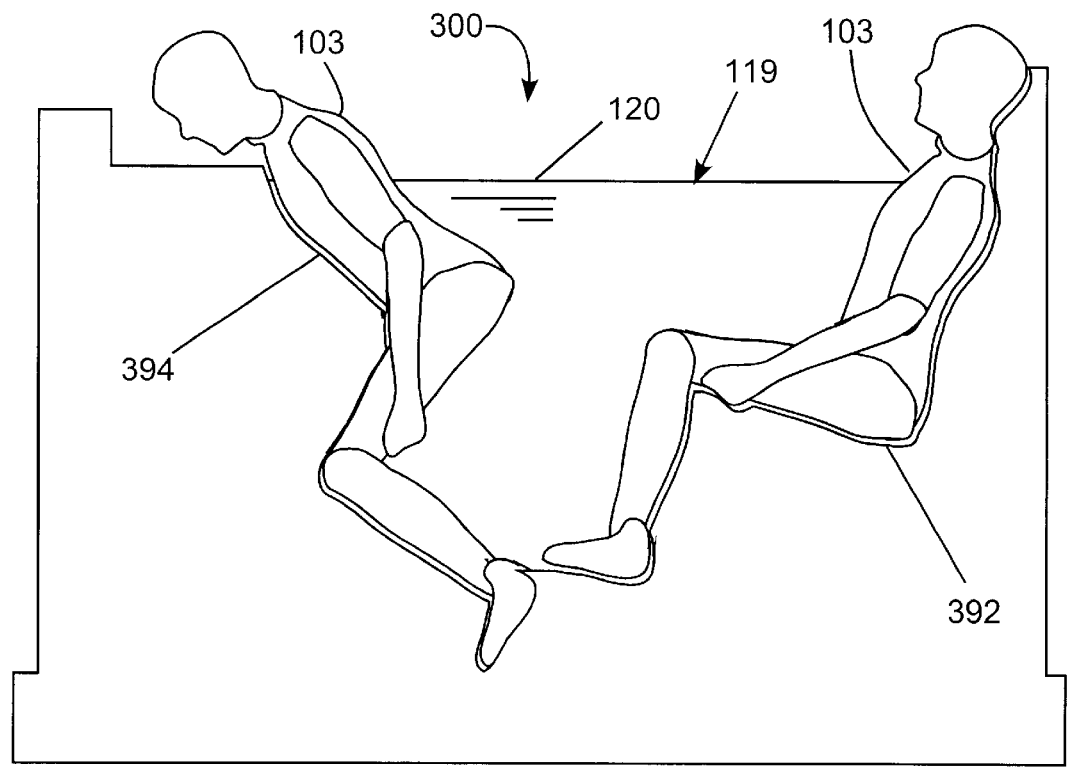
FIG. 37 is an elevational view of a manipulation device according to a third embodiment of the present invention having turnover manipulation means.
Figure 38:
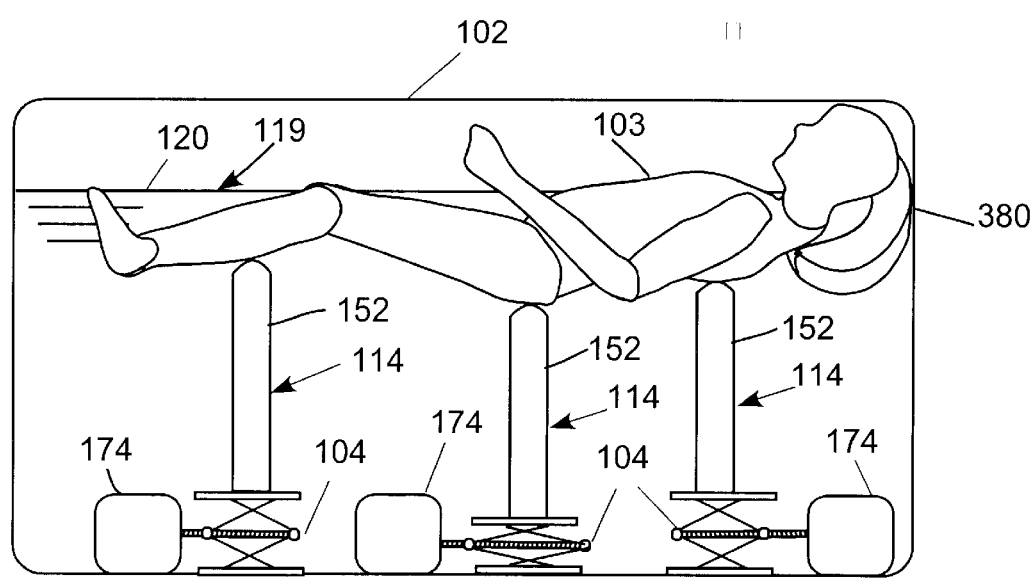
FIG. 38 is an elevational side view of a variation of the manipulation device of FIG. 3 wherein the manipulators are buoyant manipulators and the user shown lying supine on the buoyant manipulators.

FIG. 37 illustrates a manipulation device 300 according to a third embodiment of the present invention. Automatic massage or manipulation devices typically are designed to manipulate only the dorsal side of the user 103. While the bulk of muscles which can be therapeutically manipulated are on the dorsal side, there are many benefits to massaging the user's ventral side as well. There are manipulations such as abdominal massage that have been found to be useful. A device capable of manipulating both sides would require a conformable support surface. For example, when supine, a user benefits from support under the knees and neck. When prone, the user benefits from support under the ankle and around the face to allow comfortable breathing. The manipulation device 300 according to the present invention provides first and second support surfaces 392, 394 in close proximity so that the user 103 can flip over and be manipulated on the other side. The illustrated first support surface 392 is a dorsal accommodating seat and the illustrated second support surface 394 is a ventral accommodating seat.

Figure 39:
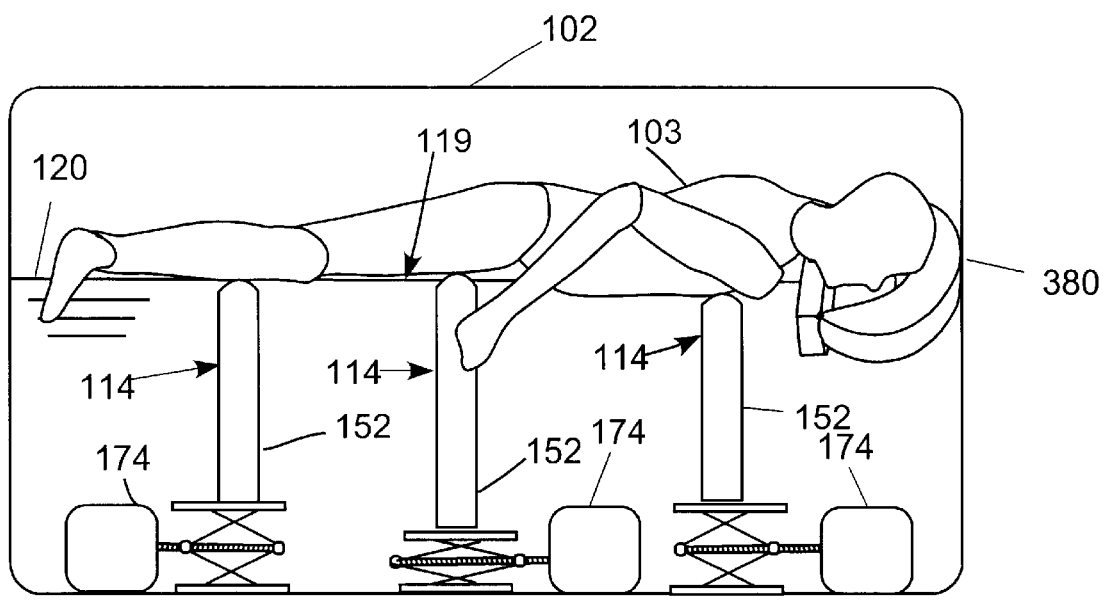
FIG. 39 is an elevational view of the device of FIG. 38 wherein the user is shown lying prone on the buoyant manipulators.
Figure 40:
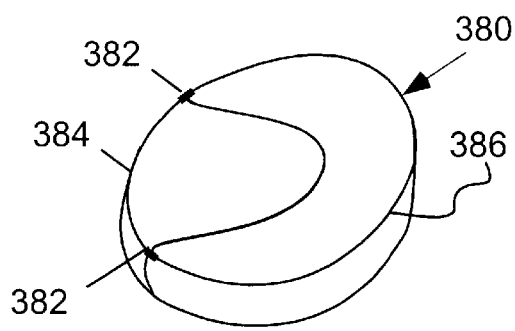
FIG. 40 is a perspective view of a headrest with a pivotable face section wherein the face section is locked in a closed position flush with an outer support and the headrest can be utilized with each of the embodiments of the present invention.
Figure 41:
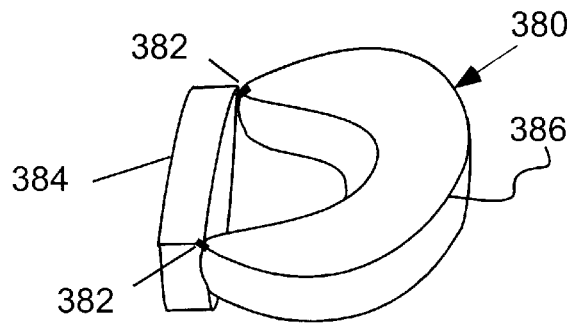
FIG. 41 is a perspective view of the headrest of FIG. 40 wherein the face section is pivoted down to an open position away from the outer support.

As best shown in FIGS. 38 to 41, the manipulators 114 are preferably reconfigurable to provide different support surfaces such as for supporting the front and back of the user 103. In the illustrated embodiment, a convertible headrest 380 is convertible between supporting the back of the head (FIGS. 38 and 40) and supporting the face (FIGS. 39 and 41). The convertible head rest 380 includes a flip down center panel 384 which is pivotably attached to the main panel 385 at hinges 382.

FIGS. 42 to 44 illustrate a manipulation device 400 according to a fourth embodiment of the present invention. An inflatable pad 354 is located between the user 103 and a massage chair 358 having a massage roller assembly 352 as a manipulator 114. The pad 354 is inflated when the user 103 first sits and slowly deflates, allowing the user 103 to relax as manipulation intensity slowly increases. Conventional massage chairs, lacking the ability to automatically control massage pressure, abruptly begin massage patterns at full intensity. This can cause users to tense up, protecting their muscles from this unexpected onslaught. In this case, the tenseness prevents the massage from penetrating to deeper muscle groups and increases bruising of the superficial muscle groups. In short, massage without an accommodation period results in more trauma to the user than therapy.

The air pressure in the air pad 354 of the illustrated embodiment is controlled by hand pump/pressure release 356 but the air pressure can be alternatively controlled by an air-compressor controlled by a hand switch and/or an air-compressor controlled by the controller 116 in order to coordinate the pad pressure with at least one of a preset pressure for a particular user, the location of the manipulator 114, the style of the massage stroke (e.g. kneading, tapping, static), user information such as height and weight, and preferences, and/or previous feedback from the user 103 (e.g. "too hard" or "too soft").

The air pad 354 may consist of two membranes with a layer of open-celled foam laminated between. The pad 354 may alternatively consist of two membranes interconnected by strips of connective material. The air pad 354 may be divided into multiple zones, supplying the user 103 with a variety of buffering actions over different portions of the user's body. The thickness or density of foam or the length of restraints may vary within a zone or vary between zones to accommodate manipulation intensity requirements for different body parts.

The air pad 354 may be slung as a hammock across an aperture bigger than user's torso. In this case, the main factors determining manipulation intensity will be the tension on the pad 354 from edge elements, the Z-axis position of the manipulators 352, and the pressure in the air pad 354. If the aperture is smaller than the user's torso as with conventional massage chairs, then the user's weight not supported by the manipulator 352 will be transferred to the passive part of the chair. The added air pressure will tend to move the user away from these passive areas and also away from the manipulators, reducing massage pressure.

The air pad 354 is typically impermeable to the working fluid but may alternatively be semipermeable, allowing the working fluid 119 to slowly leak through the air pad 354 onto the user 103. This is particularly suitable when the working fluid 119 is air being delivered by a compressed air source 356 with enough flow rate to maintain the air pad 354 at the desired pressure despite the leak. In this case, the slow leak of air through the membrane avoids the buildup of heat or perspiration in the area where the user contacts the air pad 354 which would occur with an impermeable membrane. If the air is either heated or cooled, the leak allows better thermal conduction than an impermeable air pad 354.

Figure 45:
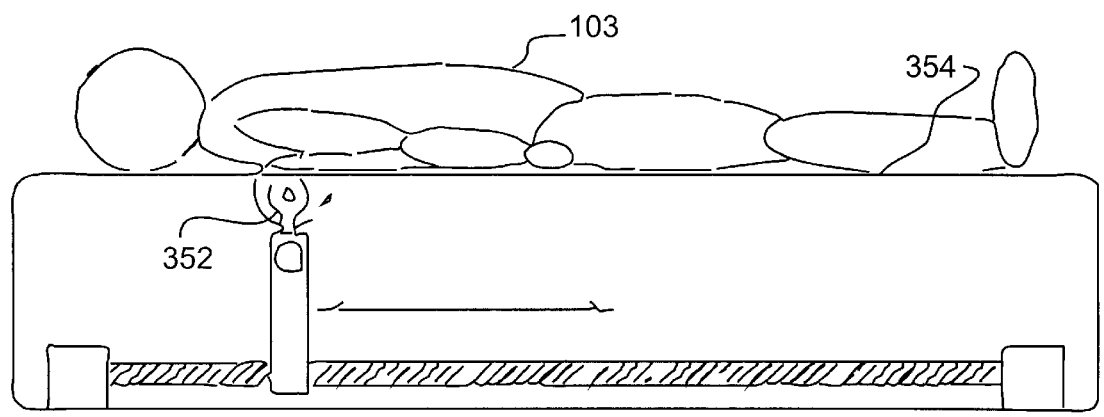
FIG. 45 is an elevational side view of a variation of the manipulation device of FIG. 42 in the form of an inflatable bed.
Figure 46:
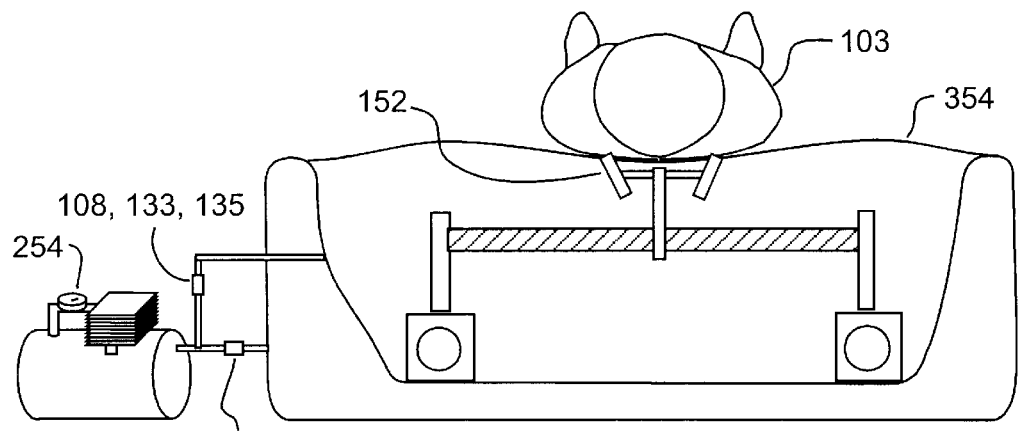
FIG. 46 is an elevational end view of the manipulation device of FIG. 45.

FIGS. 45 and 46 illustrate that the support can be configured as a table or bed instead of a chair 358 as illustrated in FIGS. 42 to 44. A table or bed configuration allows more force to be applied by the manipulators 352 for a deeper massage. In addition, a larger portion of the user 103 can be accessed by the manipulators 352 because the flexible aperture can cover a larger portion of the user 103. The bed has the air pad in the form of an inflatable mattress. The massage chair mechanism 352 is located inside the mattress 354. When the manipulators 352 are massaging the user's neck, it is useful to reduce the force applied to the user by increasing air pressure within the mattress 354. By increasing the air pressure, the supportive pressure provided by the mattress 354 will increase over each area of the user 103. Restraining any bowing-out effect of the mattress 354 by laminating foam or connective material to the underside of the upper membrane interferes with the movement of the manipulator 352 and should be used only where the manipulators 352 need not travel. Without these restraints, the upper membrane of the mattress 354 tends to bow upward when pressurized and unloaded. When loaded, the upper membrane tends to flatten. The air mattress 354 must have a flexible surface adjacent to the user but may have either flexible or rigid side walls and floor. Flexible side walls and floor would allow the device to be shipped and stored more compactly. The pressure used to control the manipulation intensity may inflate the enclosure with the same pressure or, alternatively, the side walls of the enclosure may be constructed from multiple layers of membrane with one or more contiguous volumes at pressures independent of that used to dynamically control the manipulation intensity. Accordingly, the compressor 254 is preferably connected to the side walls and the pressure volume with separate lines each controlled with independent control means such as a valve 108, a fluid flow sensor 133, and/or a pressure sensor 135.

If the air-pressurized mattress 354 is filled instead with water. The user 103 receives supportive pressure from the pressure of the water in addition to buoyancy effects. A pump can dramatically increase the water pressure within the mattress 354 with the addition of only a small volume of water, increasing system efficiency over an air pressurized bladder. As the user 103 sinks into the water, even though separated from the water by the upper membrane, the buoyancy effect will attempt to push the user 103 up and out of the water, reducing force exerted by the manipulator 352.

Figure 47:
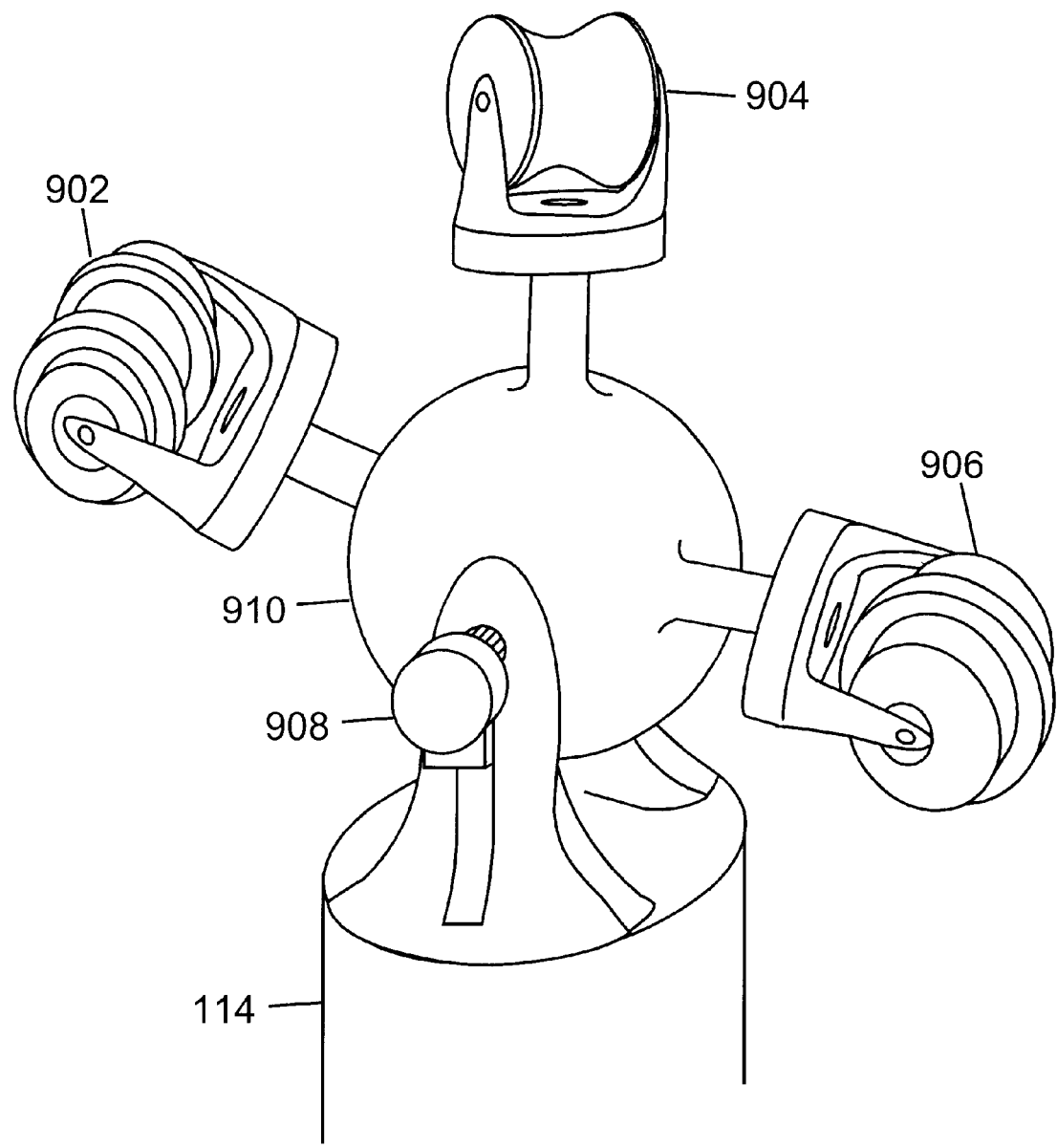
FIG. 47 is a perspective view of turret-mounted manipulators which can be utilized with each of the embodiments of the present invention.

FIG. 47 illustrates a multiple-head manipulator 114 which can be utilized with the devices of the present invention wherein a different head 902, 904, 906 is selectively used to contact the user 103. The illustrated post-type manipulator 114 includes three different heads 902, 904, 906 secured on a pivotable body 910 which can be rotated by the controller 116 with an indexing motor 908 to one of three positions depending on which head 902, 904, 906 is to be utilized. The three heads 902, 904, 906 can be of different sizes, providing different types of massages. The illustrated manipulator 114 includes a ridged massage roller 902 for outside surfaces of legs, a shallow cupped massage roller 904, and a narrow massage roller 906. In order to switch from one head 902, 904, 906 to another, the manipulator 114 can perform a "drop-catch" and change the orientation of the body 910 to bring another head 902, 904, 906 into position while the user 103 is in "free fall" and out of contact with the manipulator 114.

As shown in FIGS. 48 to 50, a kneading effect can be obtained with the use of a tracked wheel system 400 having manipulators 402 mounted on a segmented belt 404 which can be utilized with the various devices according to the present invention. A kneading action is the most pleasurable kind of massage for most users. More specifically, most users find most pleasurable a stroke passing from point A to point B followed by a second stroke originating from close to point A and finishing close to point B, where the second stroke begins slightly before the first stroke ends. The illustrated manipulators 402 include rollers 154 to reduce friction along the kneading path but other types of manipulators 114 can be utilized. The manipulators 402 may be spaced along the chain or belt 404 such that one manipulator 114 comes into contact with the user 103 before the previous manipulator 402 disengages from the user 103. This spacing may also allow an actuator such as a drive sprocket or pulley 406, a chain or belt 408, and motor 402, which progresses the chain or belt 408 to stop at a sensed position so that only one manipulator 402 is in static contact with the user 103. The assembly may then be moved in the X-axis, the Y-axis, and the Z-axes the same as a conventional single roller manipulator 114, allowing flexibility to be used either as a kneading or conventional manipulator 114. The illustrated embodiment uses a separate motor 402 to rotate the chain or belt 408 to generate (among other possibilities) a kneading pattern at computer-controlled rhythms, changing direction (either kneading in the direction from toe to head or from head to toe), or stopping the rotation to generate static pressure.

Figure 51:
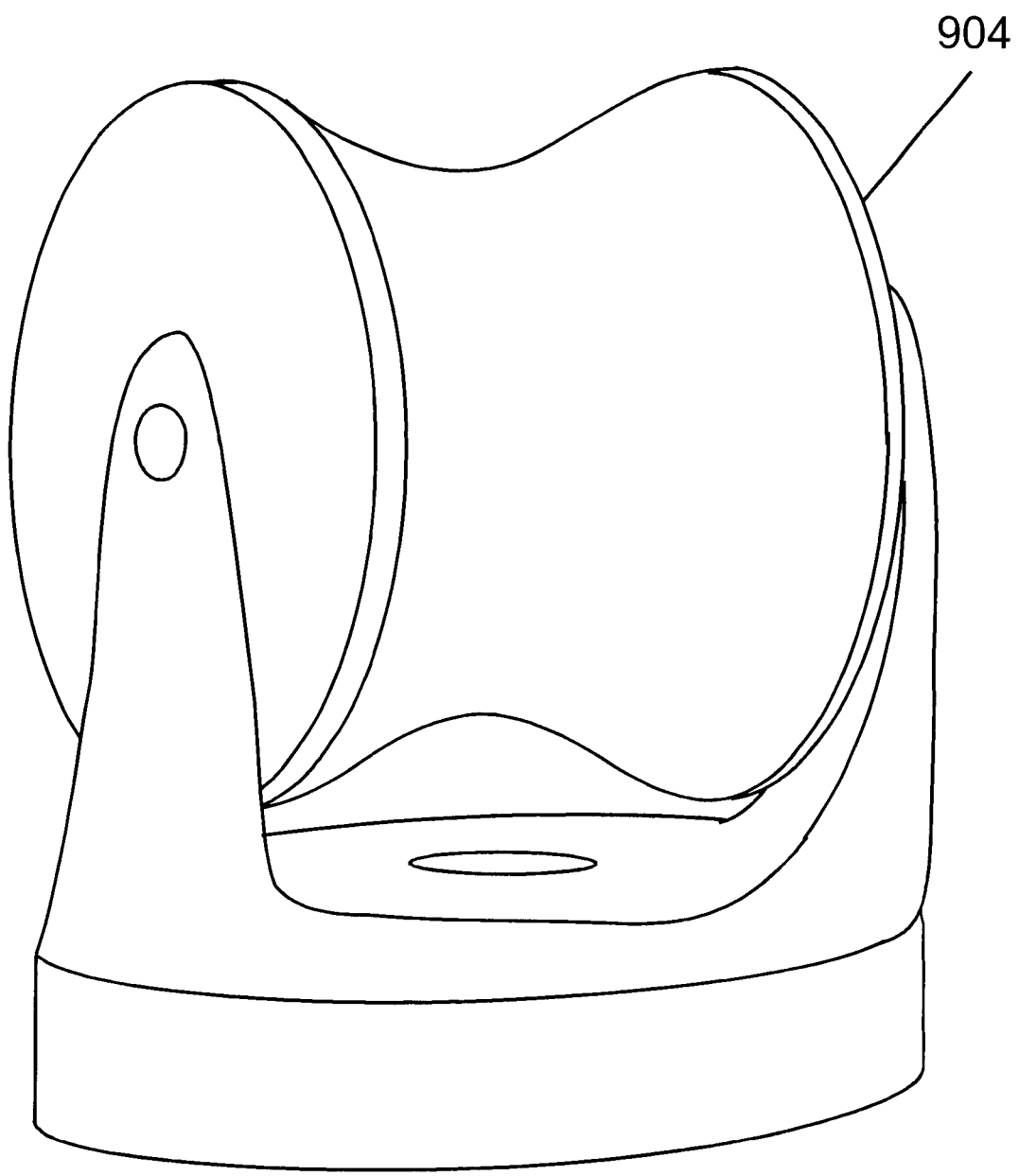
FIG. 51 is a perspective view of manipulator in the form of a concave roller which retains a limb in position and can be utilized with each of the embodiments of the present invention.

FIG. 51 illustrates a manipulator which can be utilized with the various embodiments of the present invention. The manipulator 904 is formed with a cup-shape profile to keep a leg balanced upon the manipulator 904 because the leg tends to "falls into" the center of the profile of the manipulator 904. When manipulating a buoyant user 103, without an intervening membrane 199, it is preferable to retain the user 103 on the manipulators 114, that is, ensure that the user 103 does not "fall off" the manipulators 114. This is particularly important with extremities such as the legs and even more so when lifting the user 103 filly out of the working fluid 119 to maximize manipulation intensity. This manipulator 904 applies force broadly across a wide area of contact with the user 103.

Figure 52:
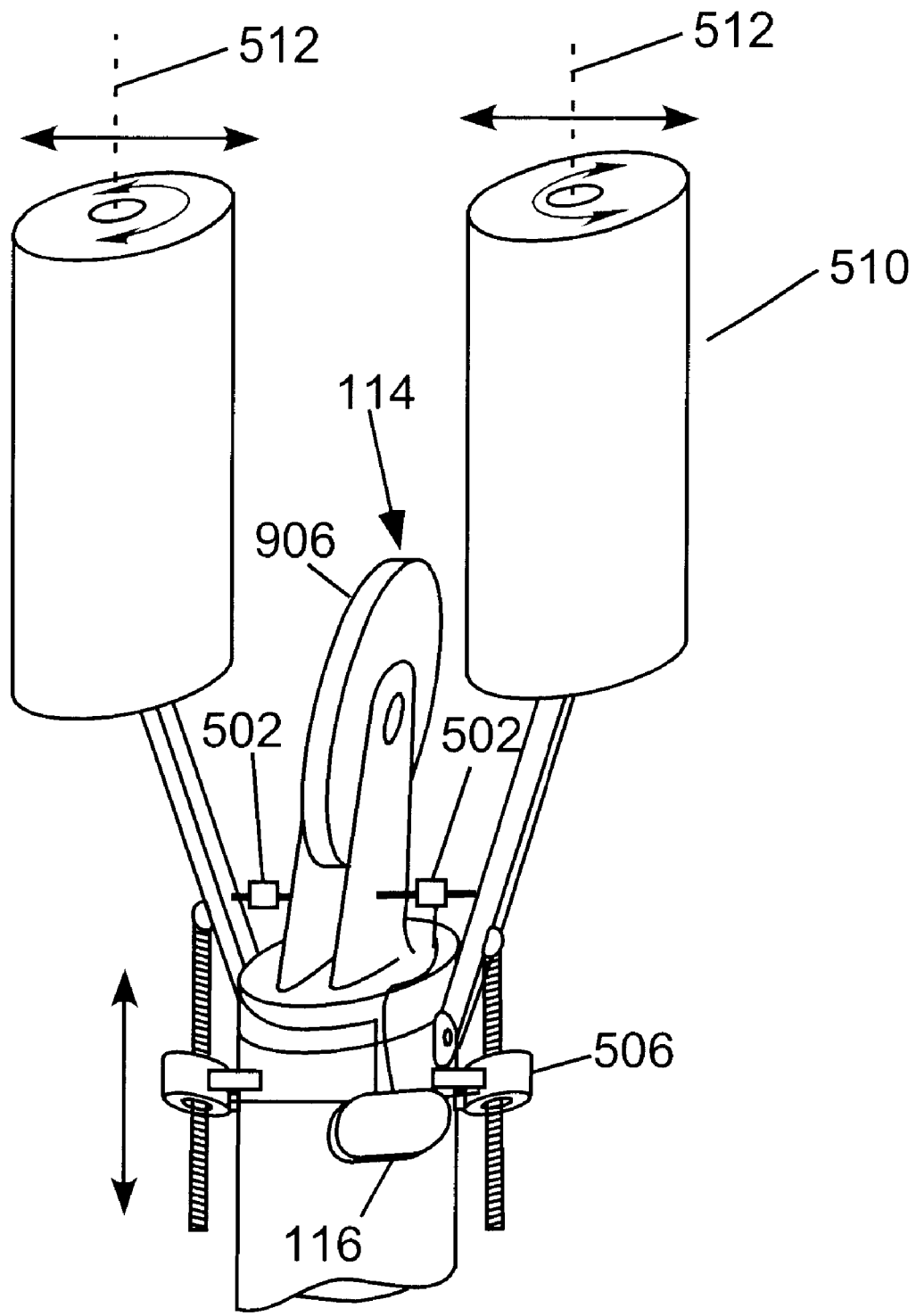
FIG. 52 is a perspective view showing guides with pressure sensors which can be utilized with each of the embodiments of the present invention.

As best shown in FIG. 52, the user 103 can also be retained atop the manipulator 114 by providing guides or guide rollers 510 to either side of the manipulator 114 such as the illustrated narrow roller 906 in a vertical orientation so that the guides 510 gently press in upon the user's legs. These guides 510 move with the manipulator 114 in the X-axis, the Y-axis, and the Z-axis and are preferably individually controlled to move in the Y-axis toward and away from the manipulator 114. The guides 510 are preferably rotatable about an axis such as the illustrated vertical axis 512 so that the guides 510 roll along the user 103 rather rub the user 103 as the manipulator 114 is moved relative to the user 103. By individually controlling the Y-axis, the manipulator 114 can contact the limb off the limb's centerline, allowing manipulation along the edges of the limbs. The illustrated guides 510 are movable in the Y-axis by linear actuators 506 having a slip clutch. The guides 510 are preferably fitted with pressure sensors 502 such that the controller 116 receives signals from these sensors 502 as the manipulator 114 moves up and down the user's leg. When both guides 510 are not pressed upon by the user's leg, the guides 510 are too far apart and are moved closer together. When both of the guides 510 are pressing against the user's leg with too much force, the guides 510 are moved farther apart. The guides 510 may alternatively be laterally located only at the outside of the user's legs, allowing the user's legs to press together and thus prevent each leg from shifting inwards off the roller 906. The guide rollers 510 may themselves provide therapeutic manipulation to the sides of the user's limbs.

Instead of changing the Y-axis location of each guide 510 individually, the guides 510 may be passively spring-loaded while still allowing the controller 116 to select whether to manipulate either the centerline of the limb or the periphery. This may be accomplished by using one of a variety of manipulator styles. For example, three rollers with different profiles may be mounted on a rotating turret controlled by the controller (as shown in FIG. 47). One roller may be a narrow roller 906 for deep manipulation along the centerline, another may be a wide roller 902 with narrow and high ridges along the edges of the roller which allow it to apply deep manipulation to the outsides of the leg, and the other roller 904 may be a soft shallowly cupped roller which strokes along the entire width of the leg.

Figure 53:
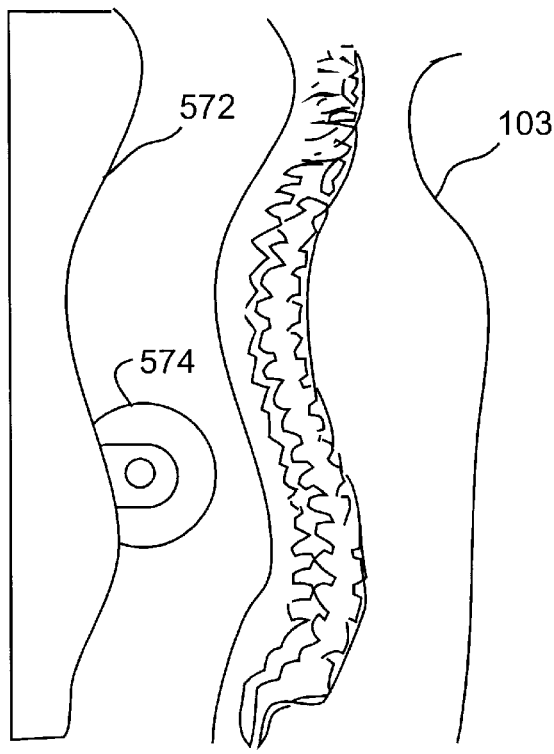
FIG. 53 is an elevational view of a massage manipulator movable along a curved track which can be utilized with each of the embodiments of the present invention.
Figure 54:
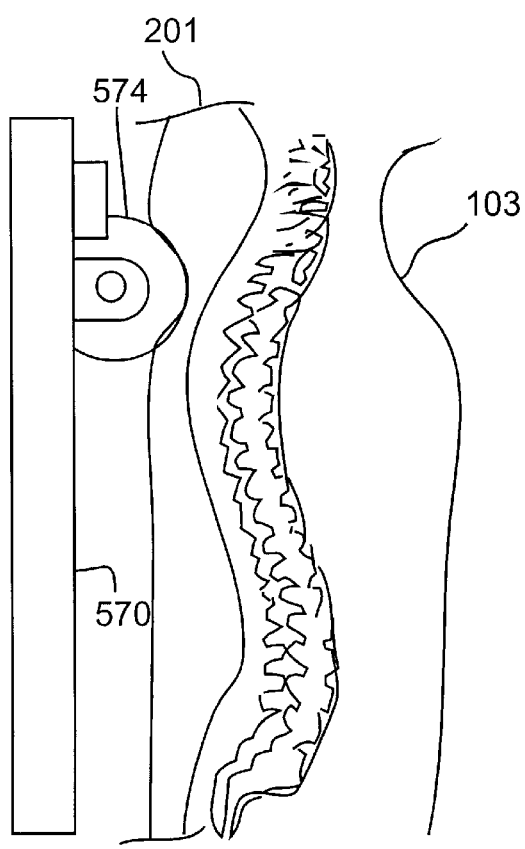
FIG. 54 is an elevational view of massage manipulator movable along on a straight track which can be utilized with each of the embodiments of the present invention.

As best shown in FIGS. 53 and 54, the various manipulation devices according to the present invention can conform to the user's back with a curved track 572 or spring-loaded seesaw mechanism. Preferably however, the problems associated with these methods are avoided by using a straight track 570 and adapting other components. For example, an air pad membrane 201 interleaved between the manipulators 114 and the user 103 can be inflated dynamically as the manipulator 114 moves along the X-axis to press into the muscles along the user's back with a constant pressure despite a curved spine. The manipulators 114, when encased in the pressurized enclosure 290, can operate similarly with the enclosure 290 inflated and deflated dynamically to provide uniform manipulation intensity as the manipulator moves along the curved spine on the X-axis. When the user 103 is buoyantly supported by the working fluid 119 with or without an interleaving membrane 199, the user 103 has approximately constant pressure exerted by the manipulators 114 as they move along the curved spine—the user's "apparent weight". The user 103 is pushed up slightly as the manipulator 114 moves under the shoulders or butt which curve down in the Z-axis. If the working fluid level 120 and manipulator height in the Z-axis remains constant, this upward motion will somewhat reduce the buoyancy support and slightly increase the manipulator pressure. If this change is undesired, working fluid level 120 can be raised or the manipulator 114 can be lowered as the manipulator 114 travels under user features which protrude in the Z-axis.

Figure 57:
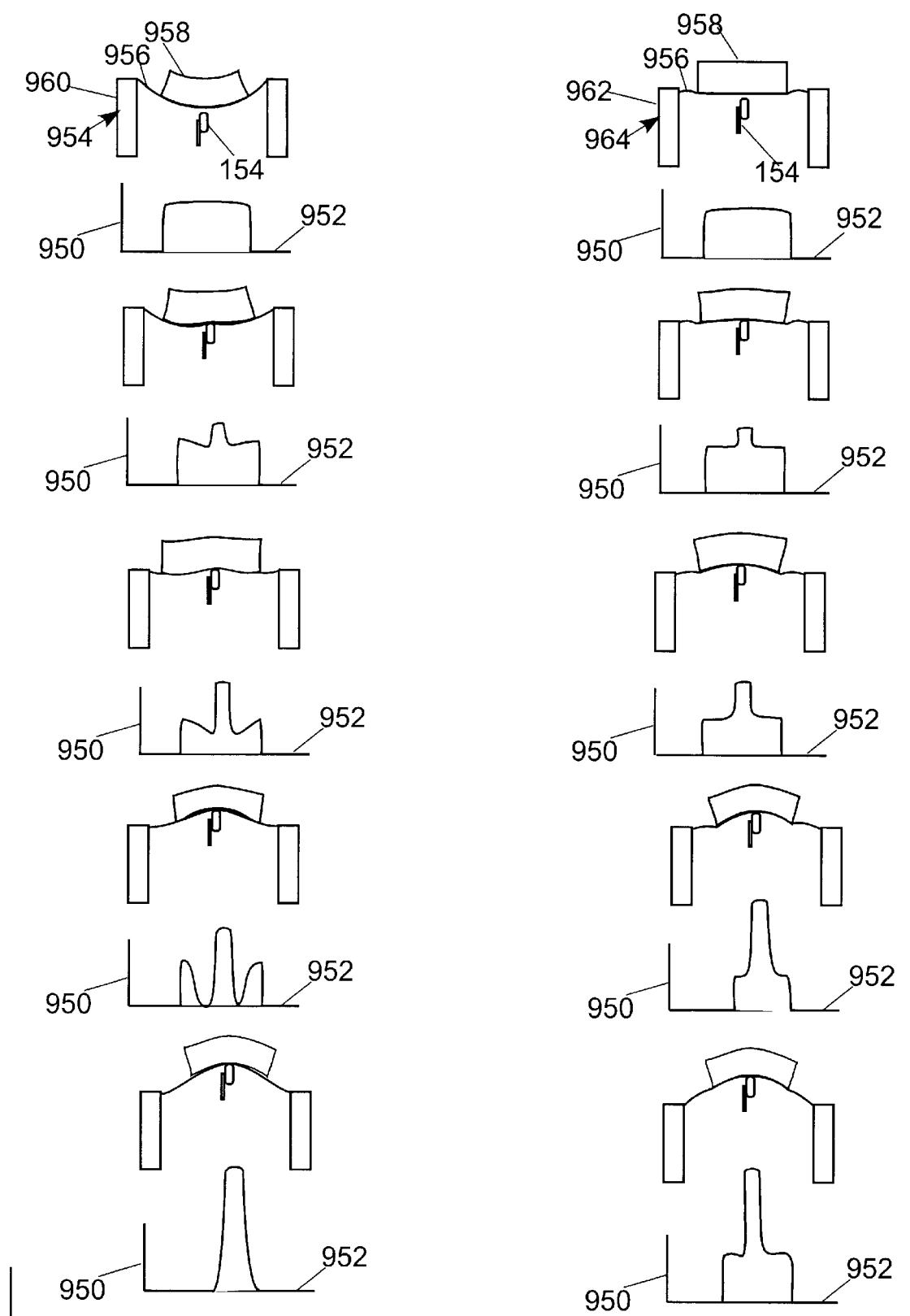
FIG. 57 diagrammatically compares forces applied to the user of a device providing no pressure support and a device providing pressure support according to the present invention It should be understood that the appended drawings are not necessarily to scale, presenting a somewhat simplified representation of various preferred features illustrative of the basic principles of the invention. The specific design features of a manipulation device as disclosed herein, including, for example, the manipulators will be determined in part by the particular intended application and use environment. Certain features of the illustrated embodiments have been enlarged or distorted relative to others to facilitate visualization and clear understanding. In particular, thin features may be thickened, for example, for clarity or illustration. All references to direction and position, unless otherwise indicated, refer to the orientation of the manipulation devices illustrated in the drawings. In general, up or upward refers to an upward direction within the plane of the paper in FIG. 3, and down or downward refers to a downward direction within the plane of the paper in FIG. 3. Also in general, vertical refers to an upward/downward direction within the plane of the paper in FIG. 3 and horizontal refers to a left/right direction within the plane of the paper in FIG. 3.

FIG. 57 diagrammatically compares forces exerted on the user by a protruding manipulator 154 of a device 954 having no pressure support with forces exerted on the user by a manipulator 154 of a device 964 having pressure support according to one of various embodiments of the present invention. The devices 954, 964 of the example have a flexible, elastic membrane 956 extending between supports 60 and walls 962, respectively. The user is abstracted as a slab 958 of material which partially conforms to the supportive surface. The slab 958 is incapable of conforming to small radii of curvature. The device 956 according to the present invention has forces 966 exerted against the membrane 956 on the side opposed to the slab 958 which result from, for example, buoyancy, air pads, and/or pressurized enclosures.

As can be seen, the unpressurized membrane provides little or no support to the user once pressure is applied by the manipulator 154. Initially under low pressure, there is some support immediately adjacent the contact zone or patch of the manipulator but the support is spatially nonuniform outside the contact patch of the manipulator and actually increases for a short distance in each direction away from the contact patch of the manipulator. As manipulator pressure increases, support immediately adjacent the contact patch of the manipulator is eliminated and support outside the contact patch of the manipulator remains spatially nonuniform and spikes of support are formed outwardly and spaced apart from the contact patch. At higher manipulator pressures, no support is provided immediately adjacent the contact patch of the manipulator and no support is provided outside the contact patch of the manipulator.

As can be seen, the pressurized membrane provides uniform support to the user once pressure is applied by the manipulator 154. Initially under low pressure, there is support immediately adjacent the contact patch of the manipulator and the support is spatially uniform outside the contact patch of the manipulator. As manipulator pressure increases, support immediately adjacent the contact patch of the manipulator remains substantially unchanged and support outside the contact patch of the manipulator remains spatially uniform. At higher manipulator pressures, support immediately adjacent the contact patch of the manipulator remains substantially unchanged and support outside the contact patch of the manipulator remains substantially spatially uniform. This example demonstrates that the devices according to the various embodiments of the present invention provide means for changing a pressure intensity of the manipulator while providing spatially uniform support to the user outside a contact patch of the manipulator. It is noted that while this example protrudes the manipulator in the Z-axis to change manipulator pressure, similar results are obtained when manipulator pressure is alternatively changed by raising and lowering the forces 966 applied to the user to apply more or less of the user's weight to the manipulator as discussed in more detail above.

It is apparent from the above disclosure that there many areas of improvement embodied by the devices of the present invention. These improvements include at least the following: (1) dynamic intensity control (DIC) which provides uniform support to the user outside the manipulator contact patch and allows the controller 116 to gradually increase manipulator intensity, permitting deeper overall massage without triggering protective muscular contractions and also allows the combination of physical therapy joint manipulation and massage chair muscle manipulation; (2) automated massage stroke technology which is above and beyond the standard kneading, tapping, and vibration strokes by disclosing novel ways to manipulate muscles and induce relaxation; (3) non-restrictive motion and biofeedback and evolving-preferencing systems which tailor manipulation to individual users; (4) multiple modalities which integrates the best features of automated massage, range of movement devices, and hydrotherapy into a single device to apply multiple tactile therapies for enjoyment in a single session; (5) human interaction facilitated by eye contact, physical proximity, multiple users, and assisted inter-user interaction; and (6) cost reduction which enables these technology be available without the burden of significantly increasing expenses or lengthening product development cycles.

It is also apparent from the above detailed disclosure that the present invention provides a system and method for supplying therapy or manipulation in the form of mechanical massage, assisted stretching, and/or cleaning to a user 103 with dynamic control over the force or intensity applied to the user. It is a further apparent that the user 103 can provide the force which resists the manipulators 114 with the user's weight and gravity (without the use of a clamping frame). This force is preferably varied dynamically within a manipulation session. The manipulation intensity is preferably independent of the user's position, orientation, or angle of inclination which is important if users are to be able to engage in other activities such as conversing, eating, or working. The method can automatically and dynamically vary the user's apparent weight as the user 103 reposes upon manipulators 114. The apparent weight of the user 103 is the user's dry weight moderated by the effect of a movable membrane and/or buoyancy. The membrane may be made to move by means of a mechanical actuator, a pressurized fluid, or other suitable means.

It is further apparent from the above disclosure, that the present invention can be embodied in at least the following forms: (a) an air pad on chair or table—adjustable air-inflatable pad atop rollers on massage chair or table to adjust massage pressure; (b) a massager with air-pressurized membrane—massage rollers encased in an adjustable air-inflatable bladder to adjust support pressure above rollers—lightening massage pressure; (c) massager with height- and/or tension-adjustable membrane—massage rollers under a membrane whose height and/or tension can be adjusted at the periphery; (d) massager with water-pressurized membrane—massage rollers encased in an adjustable water-inflatable bladder to adjust support pressure above rollers—lightening massage pressure; (e) massager with water buoyancy support—massage manipulators directly contacting the user in a hot tub such that the manipulators lift and lower the user, reducing and increasing the user's buoyancy respectively, and increasing and lowering the massage pressure respectively; (f) breath synchronized manipulation—manipulate the user in phase with respiratory cycle which is monitored by means of buoyant density measurement; (g) scrubbing washer with water buoyancy support—use sponges, brushes, and other implements of bathing as contact elements for the manipulators; (h) breath synchronized submergence—cause the mouth and nose part of the user occasionally be submerged in synchrony with the user's exhalation; and (i) breath synchronized submergence with suction restraints—use suction manipulators to actively pull the user under water in synchrony with the user's exhalation.

From the foregoing disclosure and detailed description of certain preferred embodiments, it will be apparent that various modifications, additions and other alternative embodiments are possible without departing from the true scope and spirit of the present invention. For example, it will be apparent to those skilled in the art, given the benefit of the present disclosure, that the disclosed features of the various embodiments can be utilized in combination with the other disclosed embodiments. The embodiments discussed were chosen and described to provide the best illustration of the principles of the present invention and its practical application to thereby enable one of ordinary skill in the art to utilize the invention in various embodiments and with various modifications as are suited to the particular use contemplated. All such modifications and variations are within the scope of the present invention as determined by the appended claims when interpreted in accordance with the benefit to which they are fairly, legally, and equitably entitled.

What is claimed is:

1. A device for manipulating a user, the device comprising, in combination:

a container adapted to contain a liquid for at least partially immersing the user in the liquid;

at least one manipulator adapted to engage the user;

a movement actuator operatively connected to the manipulator to move the manipulator along a path in at least one axis to apply a manipulation to the user;

means for changing a pressure intensity of the manipulator engaging the user, said pressure intensity changing means comprising means for changing buoyancy of the user in the liquid; and a controller operatively connecting the movement actuator and said pressure intensity changing means.

2. The device according to claim 1, wherein the manipulator directly contacts the user.

3. The device according to claim 1, wherein at least one membrane is located between the user and the manipulator so that the manipulator contacts the user through the at least one membrane.

4. The device according to claim 3, wherein the membrane is impermeable to a working fluid contacting the membrane.

5. The device according to claim 3, wherein the membrane is permeable to a working fluid contacting the membrane.

6. The device according to claim 3, wherein the membrane is semipermeable to a working fluid contacting the membrane.

7. The device according to claim 3, wherein the membrane is removable so that the user can be contacted directly by the manipulator.

8. The device according to claim 3, wherein the pressure intensity changing means includes a fluid tank containing a working fluid and the membrane, and further comprising means to raise the membrane above a top level of the working fluid such that the membrane becomes a lid covering the working fluid.

9. The device according to claim 3, wherein the pressure intensity changing means includes a fluid tank containing a working fluid and the membrane, and further comprising means to lower a top level of the working fluid below the membrane so that the membrane becomes a lid covering the liquid.

10. The device according to claim 3, further comprising means for tensioning and untensioning the membrane to change a level of immersion of the user in the liquid.

11. The device according to claim 3, further comprising means for adjusting a vertical position of the membrane to change of level of immersion of the user in the liquid.

12. The device according to claim 10, further comprising means for symmetrically tensioning and untensioning the membrane at sides of the user to avoid moving the user.

13. The device according to claim 10, further comprising means for asymmetrically tensioning and untensioning the membrane sides of the user to move the user.

14. The device according to claim 1, wherein the buoyancy changing means include means for raising and lowering the manipulator to change a level of immersion of the user in the liquid.

15. The device according to claim 1, wherein the buoyancy changing means include a pump operatively connected to the container for changing a level of the liquid in the container to change a level of immersion of the user in the liquid.

16. The device according to claim 1, wherein the buoyancy changing means include a valved conduit operatively connected to the container for changing a level of the liquid in the container to change a level of immersion of the user in the liquid.

17. The device according to claim 1, wherein the buoyancy changing means include means for injecting gas into the liquid to change the density of the liquid and to change a level of immersion of the user in the liquid.

18. The device according to claim 1, further comprising means for prompting the user to perform exercises.

19. The device according to claim 18, wherein a body weight of the user is part of exercise resistance and further comprising means for adjusting buoyancy of the user to change the body weight of the user.

20. The device according to claim 18, wherein the controller is adapted to selectively move the manipulator and reposition the user to multiple postures.

21. The device according to claim 18, the prompting means includes means for providing an audio signal.

22. The device according to claim 1, further comprising suction restraints engagable with the user to hold the user in place during manipulation.

23. The device according to claim 22, wherein the controller is adapted to at least partially submerge the user by the suction.

24. The device according to claim 22, further comprising means for monitoring a respiration cycle of the user and wherein the controller is adapted to at least partially submerge the user by the suction synchronously with an exhalation phase of the respiration cycle.

25. The device according to claim 22, wherein the controller is adapted to selectively apply the suction restraints to the user as a therapy.

26. The to claim 1, wherein the controller is adapted to dynamically adjust the pressure intensity changing means so that the pressure intensity begins at a low intensity at a beginning of a therapy session and is increased to a greater intensity which is applied for a majority of a duration of the massage session.

27. The device according to claim 1, wherein the controller is adapted to dynamically adjust the pressure intensity changing means so that the pressure intensity ends at a low intensity at an end of a therapy session after applying a greater intensity for a majority of a duration of the massage session.

28. The device according to claim 1, further comprising a sensor carried by the manipulator to sense force of the manipulator normal to the user a means for modifying manipulation configuration to maintain a desired intensity.

29. The device according to claim 1, further comprising a sensor carried by the manipulator to sense a presence of the user at the manipulator.

30. The device according to claim 29, wherein the controller is connected to the sensor and is adapted to begin manipulation of the user when the sensor indicates the presence of the user and to stop manipulation of the user when the sensor indicates no presence of the user.

31. The device according to claim 1, wherein the movement actuator includes a cable drive system including a first stage carrying the manipulator and movable along a first axis, a second stage carrying the first motion stage movable along a second axis perpendicular to the first axis, cables operably connected to the first and second stages to independently move the first and second stage, and at least one motor operably connected to the cables to independently drive the cable and selectively move the first and second stages.

32. The device according to claim 1, wherein the manipulator is adapted to raise and lower and the controller is adapted to raise and lower the manipulator to ease entry and egress of the user.

33. The device according to claim 1, further comprising first support surface configured to support the user in a supine position and a second support surface in close proximity to the first support surface and configured to support the user in a prone position.

34. The device according to claim 1, wherein the manipulator is reconfigurable to support the user in both supine and prone positions.

35. The device according to claim 1, further comprising means for disengaging the manipulator from a location on the user at a rate faster than a drop rate of the user and re-engaging the manipulator to the user at the location on the user to provide at least one of a tapping manipulation and a release of flesh tension in the user.

36. The device according to claim 1, further comprising means for disengaging the manipulator from a first location on the user at a rate faster than a drop rate of the user and re-engaging the manipulator to the user in a second location on the user different than the first location to allow the manipulator to move while disengaged from the user.

37. The device according to claim 1, wherein the manipulator has first and second portions adapted to engage the user and further comprising means for disengaging the first portion of the manipulator from the user at a rate faster than a drop rate of the user and re-engaging the manipulator to the user using the second portion of the manipulator.

38. The device according to claim 1, wherein there is a second manipulator adapted to engage the user and further comprising means for disengaging the second manipulator from the user at a rate faster than a drop rate of the user and re-engaging the second manipulator to the user.

39. The device according to claim 1, further comprising a restraint adapted to attach at least one extremity of the user.

40. The device according to claim 1, further comprising a curved roller adapted to cradle a limb of the user.

41. The device according to claim 1, further comprising at least one guide adapted to contact the user near the manipulator and to retain the user in engagement with the manipulator.

42. The device according to claim 41, wherein the guide is movable toward and away from the manipulator in at least one axis.

43. The device according to claim 41, wherein the guide is provided with a sensor for sensing pressure exerted on the user by the guide.

44. The device according to claim 43, wherein there are first and second guides on opposite sides of the manipulator and the controller is adapted to change a distance between the guides depending on pressure measured at the sensors.

45. The device according to claim 41, wherein the guide is also adapted to engage and manipulate the user.

46. The device according to claim 1, wherein the manipulator includes first and second portions adapted to engage the user and the controller is adapted to selectively move the first and second portions so that a desired one of the first and second portions can engage the user.

47. The device according to claim 1, wherein there is plurality of the manipulators and the plurality of the manipulators are adapted to pressure the user in succession and move along an unclosed path on the user and wherein a new one of the plurality of manipulators engages the user before a previous one of the plurality of manipulators disengages the user.

48. The device according to claim 1, wherein the controller adapted to move the manipulator under at least partially manual control of the user.

49. The device according to claim 1, wherein the controller is adapted to move the manipulator under at least partially manual control of an individual other than the user.

50. The device according to claim 1, wherein the controller is adapted to move the manipulator under at least partially manual control of an individual other than the user located at a remote location.

51. The device according to claim 1, wherein the controller is adapted to move the manipulator under pre-programmed automatic control.

52. The device according to claim 1, wherein controller adapted to move the manipulator in response to a multimedia stream.

53. The device according to claim 1, wherein the controller adapted to use a parametric pattern code based on user proportions to adapt pre-program ed patterns to users of different shape.

54. The device according to claim 1, further comprising at least one feedback device in communication with the controller and wherein the controller is adapted to generate evolving massage patterns for individual users based on incremental feedback from the individual users over time.

55. The device according to claim 1, wherein the controller is adapted for connection to a computer network.

56. The device according to claim 1, wherein the controller is adapted to provide feedback from the user to a remote location.

57. The device according to claim 1, further comprising hand-held feedback device connected to the controller.

58. The device according to claim 1, further comprising a camera connected to the controller.

59. The device according to claim 1, further comprising a microphone connected to the controller.

60. The device according to claim 1, further comprising at least one sensor in communication with the controller and capable of detecting presence of the user, and wherein the sensor is selected from the group of a motion sensor, a sound sensor, and a pressure sensor and the controller is adapted to adjust light intensities of at least one of the following to accommodate anticipated user interaction hand rail lights, step lights, feedback mechanism lights and more relevant control lights on a control panel.

61. The device according to claim 1, further comprising at least one sensor adapted to measure at least one biometric parameter of a user from the list of body shape, hand shape and fingerprint and to provide information to the controller to permit the controller to identify the user.

62. The device according to claim 1, further comprising means for monitoring the breath of a user.

63. The device according to claim 62, wherein the breath monitoring means comprise at least one weight sensor positioned to sense weight information of the user while the user is at least partially immersed in the liquid, and the controller operably connected to the weight sensor to receive the weight information and adapted to dynamically determined at least one of a respiratory phase of the user and a respiratory amplitude of the user using changes in the weight information over a period of time resulting from buoyancy changes of the user.

64. The device according to claim 63, wherein the controller is operably connected to the at least one manipulator to control movement of the manipulator synchronously with at least one of the respiratory phase of the user and the respiratory amplitude of the user.

65. The device according to claim 63, the at least one manipulator adapted to engage the user for therapeutic physical manipulation of the user, wherein the controller is operably connected to the at least one manipulator to control movement of the at least one manipulator and to the pressure intensity changing means to control pressure intensity of the at least one manipulator synchronously with the at least one of the respiratory phase of the user and the respiratory amplitude of the user.

66. The device according to claim 65, wherein the means for changing buoyancy of the user includes at least one of means for changing the immersion of the user in the container and means for aerating the liquid to change liquid density.

67. The device according to claim 62, wherein the controller is adapted to at least partially submerge the user in the liquid synchronously with the user's exhalation and ascend the user in time for inhalation.

68. The device according to claim 62, wherein the controller is adapted to detect volitional breath commands of the user.

69. The device according to claim 62, wherein the controller is adapted to detect volitional breath commands of the user and the controller is operably connected to the at least one manipulator to control movement of the at least one manipulator in accordance with the volitional breath commands.

70. The device according to claim 62, wherein the controller is adapted to detect a pain threshold of the user using at least one of a respiratory phase of the user and a respiratory amplitude of the user.

71. The device according to claim 62, wherein the controller is adapted to detect a pain threshold of the user using at least one of a respiratory phase of the user and a respiratory amplitude of the user and the controller is operably connected to the at least one manipulator to control movement of the at least one manipulator in accordance with the pain threshold of the user.

72. The device according to claim 62, wherein the controller is adapted to change the intensity of the manipulator based upon a respiration cycle indicating at least one of breath holding and sharp intake of breath.

73. The device according to claim 62, further comprising an audible signal generator adapted to generate audible signals to the user synchronous with at least one of a respiratory phase of the user and a respiratory amplitude of the user.

74. The device according to claim 1, the at least one manipulator adapted to engage the user for therapeutic physical manipulation of the user.

75. The device according to claim 1, wherein the pressure intensity changing means includes at least one of: (a) an automatic controller following a program; (b) an automatic controller following a program adapting to user feedback; (c) a user-activated switch; (d) a user controlled manual mechanism; (e) a remote user's switch; (f) a user's respiratory phase; (g) a user's respiratory frequency; and (h) a user's respiratory tidal volume.

* * * * *